United States Patent
Sprenger et al.

(10) Patent No.: US 6,723,508 B2
(45) Date of Patent: Apr. 20, 2004

(54) METHOD FOR DETERMINING THE PRESENCE OF AT LEAST ONE ALLELE OF A GSTT1 DELETION MUTANT

(75) Inventors: Raimund Sprenger, Weilheim (DE); Robert Schlagenhaufer, Starnberg (DE); Ulrich Brinkmann, Bernried (DE); Reinhold Kerb, Munich (DE)

(73) Assignee: Epidauros Biotechnologie AG, Bernried (DE)

( * ) Notice: Subject to any disclaimer, the term of this patent is extended or adjusted under 35 U.S.C. 154(b) by 75 days.

(21) Appl. No.: 09/791,105

(22) Filed: Feb. 22, 2001

(65) Prior Publication Data

US 2002/0022225 A1 Feb. 21, 2002

(30) Foreign Application Priority Data

Feb. 24, 2000 (EP) ............................. 00103844

(51) Int. Cl.$^7$ ............................. C12Q 1/68; C12P 19/34; C07H 21/04
(52) U.S. Cl. ...................... 435/6; 435/91.2; 536/23.1; 536/24.3; 536/24.31
(58) Field of Search ................... 435/6, 91.2; 536/23.1, 536/24.3, 24.31

(56) References Cited

U.S. PATENT DOCUMENTS

| | | | |
|---|---|---|---|
| 5,552,283 A | | 9/1996 | Diamandis et al. |
| 6,025,480 A | * | 2/2000 | Massague et al. ......... 536/23.1 |
| 6,150,514 A | * | 11/2000 | Swensen ..................... 536/23.5 |

OTHER PUBLICATIONS

Walker and Little, from DNA PROBES, 2$^{nd}$ ed., section 7: Amplification Systems, pp 255–269. MacMillan Publishers LTD, 1993.*
Research Genetics, "Designer PCR". from Nucleic Acids Research, vol. 22, 1994.*
Genbank Accession No. AP000351, 2$^{nd}$ version, Jul. 8, 1999.*
Keinlinen et al: Clinical Chemistry, vol. 36, pp. 900–903, 1990.*
Carter, D Human DNA sequence from clone 322B1 on chromosome 22q11–12, complete sequence. Accession No. Z84718, NCBI, Nov. 23, 1999.*
Van Sloon P P H et al:"Determination of spontaneous loss of heterozygosity mutations in Aprt heterozygous mice" Nucleic Acids Research, vol. 26, No. 21, 1998, pp. 4888–4894.

Fortina P et al:"Flourescence–based, Multiplex Allele–Specific PCR MASPCR) Detection of the DeltaF508 Deletion in the Cystic Fibrosis Transmembrane Conductance Regular (CFTR) Gene" Molecular and Cellular Probes, GB, Academic Press, London, vol. 6, Aug. 1, 1992, pp. 353–356.
Lohmann D et al: "Detection of Small RB1 Gene Deletions in Retinoblastoma By Multiplex PCT and High–Resolution Gel Electrophoresis" Human Genetics, DE, Berlin, vol. 89, No. 1, 1992, pp. 49–53.
Shi M M et al: "High–throughput genotyping method for glutathione S–transferase T1 and M1 gene deletions using TaqMan probes" Research Communications In Molecular Pathology And Pharmacology, vol. 103, No. 1, 1999, pp. 3–15.
Kelsey K T et al: "The glutathione S–transferase theta and mu deletion polymorphisms in asbestosis" American Journal of Industrial Medicine, vol. 31, 1997, pp. 274–279.
Oke B et al: "GSITI null genotype frequency in a Turkish population" Archives in Toxicology, vol. 72, 1998, pp. 454–455.
Abdel–Rahman S Z et al:"A multiplex PCR procedure for polymorphic analysis of GSTMI and GSTT1 genes in population studies" Cancer Letters, vol. 107, 1996, pp. 229–233.
Weincke J K et al: "Gene deletion of glutathione S–transferase theta: Correlation with induced genetic damage and potential role in endogenous mutagenesis" Cancer Epidemiology, Biomarkers & Prevention, vol. 4, 1995, pp. 253–259.
Pemble S et al: "Human glutathione S–transferase Thets (GSTT1): cDNA cloning and the characterization of a genetic polymorphism" Biochemical Journal, vol. 300, 1994, pp. 271–276.

* cited by examiner

Primary Examiner—Jehanne Souaya
(74) Attorney, Agent, or Firm—Domingue & Waddell, PLC

(57) ABSTRACT

Method for detecting the presence of at least one single allele of a deletion mutant, specially as PCR assay for detecting the presence of at least one GST1*0 allele wherein a PCR is performed with two primers, of which one stems from the sequence upstream of the deletion area, and the other stems from the sequence downstream of the deletion area and wherein the production of the corresponding DNA fragment in the PCR is checked. Useful for testing of patients to check whether they are susceptible to toxins or resistant or overly sensitive to certain therapeutic agents or belonging to risk groups.

1 Claim, 7 Drawing Sheets

SEQUENCE LISTING

<160> NUMBER OF SEQ ID NOS: 36

<210> SEQ ID NO 1
<211> LENGTH: 5000
<212> TYPE: DNA
<213> ORGANISM: Homo sapiens

<400> SEQUENCE: 1

| | | | | | | |
|---|---|---|---|---|---|---|
| gggtctggcg | ggcaccagtg | cgatggtgcg | ctgtacttgc | ggcacaggta | gtaaaggatg | 60 |
| gccgcgctgc | agaagggggcc | ggtcaggggc | actgcccttg | ccttcctgag | tgccactaca | 120 |
| tcaaccaccc | cggtgtggcc | tgggcccaac | tgctggggct | tccagagcaa | agaggagccc | 180 |
| aaacggcccc | gagaaagacc | ttcaccagag | ctgtctgtct | gacagtcagt | aagggctggg | 240 |
| aaggagccct | gcggggtgag | taggagttgg | gggctggtgg | tataacaaag | agtaggccag | 300 |
| caggggaac | aacacgtgtt | gaattgggat | gctgaggtgg | gaggatcact | tgatcccagg | 360 |
| aatttggggc | tactgtgagc | caagatcaca | ccactgcact | ccagcttggg | tgaaagatca | 420 |
| agatcctttt | tcaaaaacaa | aaacggggggg | gcacgatggc | tcacacctgt | aatcccggca | 480 |
| ctttgggagg | ccaatggggg | cagatccctt | gaggccagga | gttggagacc | agcctggcca | 540 |
| acatggtgaa | accctgtctc | tactaaaatg | aaaatacaaa | aattagctag | ttgtggtggc | 600 |
| acacacctgt | aatcccagct | acttgggaag | ctgaggcacg | ggagtcactt | gaacctggga | 660 |
| ggcagaggtt | gtagtgagcc | aagattgtgc | cactgtactc | cagcctgggc | cacagagcaa | 720 |
| gactctgtct | caaaaaacca | acaaagaaaa | acacatgctg | aaatacgagg | gtaaagggag | 780 |
| caaggtaaat | ctgaagaaaa | gagagtaggg | ggttgcaact | ggaagaaggg | tggggggtgat | 840 |
| tggggagtga | tgaggcagcc | agagacactg | tggagtccac | ggagggtagc | ccctggaggt | 900 |
| gcagggaggt | tatggactta | atgcttaaga | ttaggcatta | tataagccag | ggcatgaaag | 960 |
| gatccatctc | tctggtgctg | gatggagggt | gagcccgagg | gggcagaatg | gacaatgagg | 1020 |
| gggccagcaa | ctatcgggaa | ggttgtggtg | tctgggaatg | ttggaggcca | tggggacaga | 1080 |
| gggaagggga | tggagggggag | acatgcttcg | gaggggatgt | cctaggcctt | gctgattgat | 1140 |
| ggctggtgtg | ggaacctccg | cagcacaagg | gctcctttat | catcaccagc | agcaaccatg | 1200 |
| ccaaggtaaa | aaggtcaggg | catggagaga | gctatcggtt | aaaaagtggc | aggagagaca | 1260 |
| gcaactggct | gcaagactca | gaacttcttg | gctgggcacg | gtggctcacg | cctgtaatcc | 1320 |
| cagcactctg | ggaggccgag | gcgggggggat | catgggtca | ggagatcgag | accatcctgg | 1380 |
| ttaacacagt | gaaaccccgt | ctctactaaa | aatacaaaaa | aattagccag | gcatggtggc | 1440 |
| gggcacctgt | agtcccagct | actcaggagg | ctgaggcagg | agaatggcgt | gaacccggga | 1500 |
| ggcggagctt | gcagtgagcc | aagatagcgc | cactgcactc | cagcctgggc | aacagagcga | 1560 |
| gactccgtct | caaaaaaaaa | aaaaaaaaaa | aacttctttg | gatcctgatc | caaacaaact | 1620 |
| gccaagaaaa | tgtttaggag | ataatcatag | agttttgaac | aggagccaca | tattagatga | 1680 |
| aatccaggaa | ttattgttaa | ttttatgagg | tatcttaatg | gtatcgtagt | gatgctacgc | 1740 |
| tctatcctag | cccaggctgg | agtgcagtgg | cgcaatcaga | gttcactgca | gttctgaact | 1800 |
| tcctggcctc | aagcgatcct | cccgtgtcag | cctctggaag | tgctcggatt | ataggcatga | 1860 |
| gccaccacac | ccagcctgtt | gctttttttt | tgtttgtttt | aagaactctt | atctctgaaa | 1920 |
| agtatgttcc | taaacatttta | ttgatttatt | tacttattta | tttttattt | tgagatggga | 1980 |
| tctcactctg | ttgcccacgc | tgaagtgcaa | cgacgcagtc | ttggctcact | gcatcctctg | 2040 |

-continued

```
cctcctggct caagcagtct ttccgcctca gcctcccgag tagctgggac tacaggtgca    2100
gaccaccatg ctggctaatt tttgtatttt ttgtagagat ggggttttgc catgttgtct    2160
aggctaggct ggtcttgaac acgtgagctc aggccatccc ctcacttcag cctctcaaag    2220
tgctagaatt acaggcatga gctggcttct aaacatttat gaatggaatg atggggtgtc    2280
tgggaggcag gggaatagaa atgatgtaaa ctggacccca agttggcaag agtcagagct    2340
gggcgatgga tttgtggggt tcctcgtgtc cctcattagt tagtattcac tctcctttag    2400
tgcacgtgtg agattttcca tggtcaaaca gacaaatgct tgcactgaac ctcccaggag    2460
aagcagagac agatggtgca agggcccag ggaagactta cctttcactt aagataaatt    2520
tcccatcttt gaggctgggc agcttcctga ggggttgat gtcaatgtat cctttgctgt    2580
ggtggtgacc tgggaggggc agggaaggtc tgaggctgtg ggactccagg ggagagagaa    2640
ctgagactcc cagagaccca aacgcctccc tctctatttt ctcaagaaga gggaactgag    2700
gcccggaggg acattgcgtc tcaccccagg tcacagggca aggcagttgc agaaccggac    2760
tgcgatcaga actgctggct cccagcctgc tccaccctag gtttggtgac tcccgtgcct    2820
cctacctgtg tcccaggacc aggacgaccc ttttacccag aagccggagg cctccagtgc    2880 ccaccccaa agctggatct gaaaacacag cctttgaatc acctgaagcc ctgagggcct    2940
gggtcccatc cgcaatccca tcgctctcac tctgtctcca ctttaaggaa gccaggccca    3000
gcacacagct ggacatccaa agggaagctt ctcggacaca atcagggtca tcttaacagg    3060
gaacctgagg tgggggcagg aactgaaact cttcctggac cagccgcctc cagttggaaa    3120
catttctggg ggctccactc gcagcccgtt catttccaca gcttccctgt ctcttcctct    3180
gtgttctaga ggcttctgct tttgcaggct gagcttttgg agtccctctg tgctggggat    3240
ggagttggag cccacccctc tgaccctcac tcagggttag tggagccctg agcctttctg    3300
aacactgggg aggatgggtg tagacggact gtgcacttct gccccttttg ccaacctggt    3360
gggcaggtgc tgagttcaca aggtcctaga atcccacaag gaagccaggg tgcctggtgg    3420
gagcccaggg agtcccagct actgttcctt ccccttctc ctcgaaaagc ctgttcatct    3480
gtggcgtggg gactgtcatt agtgagcact gactaaggta ggctggacaa ggatgcagcc    3540
tacaagccgc gtggcatctt ttccttccct gtggacctct ggggtgattc ccttgtctct    3600
gtctctgctc ctcagaaacg cccctatcag gctgtgcgcg gtggctcacg cctgtaatcc    3660
cagcactctg gaggctgagg tgggcagatc acttgaggtc aggagtttga ccagcctg     3720 gccaacatgg tgaaacccct gttaaaaata caaaaaatta gctgggcgtg gtggcatgca    3780
cctctaatcc cagctactcg ggaggctgag gcaggagaca cacttgaacc cagcagaggt    3840
tgcagtgagc cgagatagca ccaccgtact ccatgctggg caacagagcg agactccatc    3900
aaaaaacaag aaaaaagaa aagccgcaat ctgtgtgtcc tgcctccccc caggaccagg    3960
cctgccaggc agcagtggga gttgaccttt cagcagatcc acaaactgaa agttgaactg    4020
gatgtcatgc ttcttcgaga agatgtagac ggcacggcag ggtgctgaca gcaggtccat    4080
gtagagctcc agtgccatgt tgagacacat gccaggcccc acagccgcag ttggccagcc    4140
acagacctgg gcctatgtct ggccagagtc cctggccctg tgccctctcc gatctgggcc    4200
caggatcctg tgttccccag ggaaacctct tgtttccctt tgtgttgtca taaggccagg    4260
aagcctgcaa ttctcacagc atcaaggatt ctaaggaggc ccaggagtag gctggggaga    4320
ggcccgtggc aaaggtgtgg cagccgtgac cctactctcc cccttccacg tgtgcctgtg    4380
```

-continued

```
cccagtggtg ccacctcaca gacaccagtc tgagaaggga ttatgcctgg gaattcccac      4440
ggctggattt tcattgcaga acctgacgaa aggggctttg cagggtccag aatgaagagg      4500
aggcaatgag aattatccct ggaggattct agaagtagag gctgggagta tccacaggta      4560
aatcgagcct gaactatgac tagaaaggaa ttgggagaaa gagacacagg tgaatcgagc      4620
ctgaactatg actagaaagg aactgggaga agagacaca ggaaactgtg agctttggga       4680
gcaatgggga caccaccacc aggaagtcag ggggcactca gccggtgtgt gccacacaga      4740
ggagcctaga aacttcctgg ccttggttgg ggctgcagtg gccagactgt gtacctggtg      4800
gccaaggaag gtaactagag ccccacgtag aggactgagt gccactcact ctatgctgtg      4860
atctaatagg tctaggctga gaaatgggac tgaccccact tctggtgaca gagtaagcct      4920
ggagacaagc gaagagcatg cagtgtgttt attgcagaca gcagggtgca gtggagtggg      4980
ctgcacccac tgcacctgct                                                  5000
```

<210> SEQ ID NO 2
<211> LENGTH: 5000
<212> TYPE: DNA
<213> ORGANISM: Homo sapiens

<400> SEQUENCE: 2

```
tgtggtttta attttgtttt tcatcctttta ttgcaaatgt atactattga ttttttgtgta      60
ttaatcttgt accctgcaac cttgctgaac ttatttttatt ttattgagat ggagtctcag     120
tcagtcaccc aggctggagt gcagtggctt gatcttggca cactgcaacc tccacctcct     180
gggctctggt gattctcctg cctttgcctc ctgagtagct gggactacag gcatgcgcca     240
ccacgcccgg ctaattttg tatttttagt agagacgggg tttcaccata ttggacaggc     300
tggtctcaaa cttctgacct catgatctgc ccgccttggc ctcccaaagt gctgggatta     360
caggtgtgag ccaccgtgcc cagccttgaa cttgtttatt agctctaatg gtttttaagt     420
gagttaagaa tttctgtaat gtcatctgtg aatagagatg gttttacttc tttctttctg     480
atctagattc caccttgttc cttttttcttg cctaattgcc ctaataagta gaagtagtgt     540
gaatgaacat tcttgtcctg ttcctgatct tagggggaa acgcttgatc tttcacaatg     600
gatgaagtat ggtgttagtt ataggttttt catagatgct tttgtcaag ttgaggaagt     660
tcctttctcg tcttcatctg ctgagtaatt ttatcgtaaa aggatgttag gttttgtcaa     720
atgccttctg tgcattagga tgatcatgtg actttctatt aacatggtat gctacactga     780
ttgatttttg tatgttgaac tgcatttgta ctcctgggat aaatcctacc tggtcaaggt     840
gtatgatcct tttaatatgc tgctggattt gatttgctaa tattttgctg aggattttta     900
catctatatt tataaggata ttgctttgta acttttatttt cttgtaatgt cttttttctgt     960
ctttggtatc agagtaattc tggcctcata gtatgagtta aaaatatttt cttcctgttt    1020
tatttttttg gaagagtttg tgaaggcttt gtgttagttc ttcaagcttt tggttgaatt    1080
caccagggaa gccatctggt cctgggcttt tctttgtgga attttttaaaa ataattaata    1140
ttttaatctc tttatttgtt acaggcctat taaaatttta tctttcttct taagtcagtt    1200
ttggtagatt gtgtgtttct aaaattttcc catttcatct aggttgtcta aattgtccac    1260
atatagttat tcatagtatt tctaaacttt tgaatttctc tatgaccaat gtgatgtctc    1320
cattttcttt cttctggtt tccatttcat tttttcattt tgttttttgt ttgtttttg     1380
agataaggtt cttctatgtg cccaggctgg agtgcagtgg tgcaatcata gctcggtgta    1440
accttgaact cttggactcg agtgatcctc ccacctcggc cacccagtta gctaagacta    1500
```

-continued

```
caggcttgca ccaccacacc aagctaattt ttttaaaaaa tatattttt  agaaaaagt    1560 ctcattgtgt tacccaggct gttatcaatc tcctggcctc aagtgatcct tctgcctctg   1620 cttttccaaag tgctgggatt gcaggtgtga gccattgcac ccagcctcca ctttctttct   1680
tggtgaataa tttgacccct attttttca  cttggctatt ctaagtaaag gtttgccaat    1740
tttgttgatc tttgcaaaga tccaattttt ggttttattg attttattgc ttttctattt   1800
tctatttcat ttatctccat tctaatcttt attatttcct gttttctagt ggtgttgggt   1860
tgagtttgct cttatttttc tagttcctta aggtgtaaag ttaggttatt gattcaagat   1920
cattcttctt taactatgt gtttacagct ataaattttg ctcttagaac tgcttctgct   1980
gcatcctata aatctgggca tgttgtgttt tcattttat  ttgttcagga tacttttga    2040 tgtcccttgt gatttcttct ttaacccatt tgttgtttaa gagtgtgctg tttaatttct   2100
atgtgcttgt gagttttcta gttttccttc tgttcttgat ttttaacttt attccactgt   2160
gtccagagaa catactttgt gtgatttcaa tcatcttaaa tttgagactt aggaccaaat   2220
atatgctcta tactgagaa  tattccatgt gctctttaga agaatgctta ttctgctcct   2280
gtcgggtgga acgttctgtt catgtctagt gtatgcgatt ggttaatcgt gcttttcaaa   2340
ttccctattt ccttgatggt cttctgtagt ttttctatta ctgaaagtgg ggtattgaag   2400
tcaccaacta ttattactca caatgtaacc atatttaacc ctttacttt  aaaattcttt   2460 ttggaaactg gaaggatctg taaccaccac ccactccac  atcagaccct atgcatatgc   2520
caactgtctg ctgctcagca gctgtgatgg ttgttccagt tctttattag gcaaagaaca   2580
gttgtttttt tgttttttg  ttttttttt  tttaacattt cctttaagga aggtggctca   2640
gattgctaag ccagccaggc cctgcgggac aggctgcgcc tagggtcacc tgctcttctt   2700
cagcaactca gaaatattct ccttgaccat tgaatccaat gttgaaaagt cccagtcggc   2760
caactgcatt agtcgatcat gggcctccct aaagaggcca gagccaatat tcagctccac   2820
ctgcatacgc cactcagcta gcttggagct gttgaggaag acattatagt tggctgccat   2880
gggctgtaga tagacgaaga caaagacgtg gtcagcctgg ggaccagccc cacctgggtc   2940
ctctcccaca gcctcaggcc cacgtcccta acatctacct atgcaaagaa ttaggctgct   3000
gacccccaag gcctgagcaa ggggtcacag actatgtaat agatgtaggt ggggatggag   3060
gatccagaat ccctcagagt cctcagtcac tggtcttctt gctccaagcc ttctgaacca   3120
tgctgagagg gctcctggcc caggcacttc ccacttctcc agcctgcgac ctcgcatgaa   3180
tcctgccttc ttccagggaa acccttatc  ccaggtgtgt atatgtggat gagggagaga   3240 actcaggtt  tttcctccat gtttagcctc ccactgtgat caagctcagg ggctaggatg   3300
ggagacctgg cgggcagtct accctgcagt ttcgctggct tactaagagt ttggtttgca   3360
cccaagatct ttgggaagcc caagaatggg tgtgtgtggg tgaaatgtaa ggggtgggga   3420
cgaagcatat ggctgaaccc ttggggcagg ccagaatgat ttttcctggt gctggtctgc   3480
cctgcaaaca gaccaaggag actaattttc atatcagcca gagatctctg ggataaggaa   3540
aagaatactg cattttctgg tcaatccacc aggaccccag gtccctcctc tcgggcatat   3600
ctctggctga tatgcaaatt agtctctttg gtcagtgtgc agtgccctag ctggtgtgca   3660
ggatggccag ttgagaccct ggccagtgtc ttgacaagca gaactggtca ccctcccctg   3720
catgtagagg ccacataaat gccccacact caggtgtgcc tccaaatgca cagtggatgc   3780
ccctcagacc cagccacgag agctgtcctc cagagctgtc tgtctggagc tctgggaaac   3840
```

-continued

```
aggcagggcc agaaggacac ccaggaagcc agtgaacatt tcctggagag tccagcaaga    3900
ggaggaggta tctgggatgc tggtggattg agcaggaaat gcagtgttct tctctatccc    3960
aggctcaccc tccgggtcct cccacaccga agaatctttg tcaagtgtgg agaactgtga    4020
tccttcctga ttcataacat tctgtgcttc ctgttgcccc gattgagtcc aggcccccag    4080
gcctggttcc cgcagccccc atggcagctc tgcctgcctt tcccgcctca ccagcctatc    4140
ctcaagtgat ggcccattg gtcacagagg agtcctacct ctgcccaggg tctaaccctc     4200
ctccaatcca ctccacacct gcatcatctc caccacggcc accaggtcag ccagtgagat    4260
ttggttcccg gtgatgaaca tcttatcctg cagaaaatac tcctcaaaga gctgcaggct    4320
gttcttcacc tcttccactg catgctccat cttctcagct gaaacttcct cccctgttat    4380
ctttgggatc agcaactggc cagggttggg aagaggaggg aagaggaggc tgcactccag    4440
ggccacctgc cctgccaggt ctctgtactc ttgtctgctg gatagatatt gaacacttcc    4500
caggatataa agcagtttca cctcttttag cagttctgat tggtggaagt tgctgggaac    4560
catgtgttca caaggatttg gggagctcag caggcataag tcctgtgatt gattagtgat    4620
gtctgtcaca ggcatagaat tcaaagtaga gacacatgta ctggttattt gtcatcttct    4680
aattttctat aggccatact cttttttgtt tttgttttt gagatggagt ctcactctgt      4740
cgcccaggct ggagtgcagt ggcacaatct tggctcactg ccaactccaa ctcctgggtt    4800
caagcaattg tcctgcctca gcgtcctgag tagctgggat tacaggtgcc catcaccaca    4860
cccagctaat aattttgtat ttttagtaga gatggtgttt cacaatgttg gcaaggtagg    4920
tcttgaactc ctgacctcaa gtgatctgcc cgcctcggcc tcccaaagta ctgggattac    4980
agttgtgagc caccgtaccc                                                 5000

<210> SEQ ID NO 3
<211> LENGTH: 23
<212> TYPE: DNA
<213> ORGANISM: Homo sapiens

<400> SEQUENCE: 3
ttccttactg gtcctcacat ctc                                               23

<210> SEQ ID NO 4
<211> LENGTH: 20
<212> TYPE: DNA
<213> ORGANISM: Homo sapiens

<400> SEQUENCE: 4
tcaccggatc atggccagca                                                   20

<210> SEQ ID NO 5
<211> LENGTH: 20
<212> TYPE: DNA
<213> ORGANISM: Homo sapiens

<400> SEQUENCE: 5
ccctcactca gggttagtgg                                                   20

<210> SEQ ID NO 6
<211> LENGTH: 20
<212> TYPE: DNA
<213> ORGANISM: Homo sapiens

<400> SEQUENCE: 6
gatgccacgc ggcttgtagg                                                   20
```

-continued

<210> SEQ ID NO 7
<211> LENGTH: 20
<212> TYPE: DNA
<213> ORGANISM: Homo sapiens

<400> SEQUENCE: 7
gattggtgga aggtgccggg                                              20

<210> SEQ ID NO 8
<211> LENGTH: 24
<212> TYPE: DNA
<213> ORGANISM: Homo sapiens

<400> SEQUENCE: 8
cgtgtctcta cttcaaattc catg                                         24

<210> SEQ ID NO 9
<211> LENGTH: 24
<212> TYPE: DNA
<213> ORGANISM: Homo sapiens

<400> SEQUENCE: 9
taagatacct cataaaatta acag                                         24

<210> SEQ ID NO 10
<211> LENGTH: 21
<212> TYPE: DNA
<213> ORGANISM: Homo sapiens

<400> SEQUENCE: 10
ggcagaatgg atagtgggga g                                            21

<210> SEQ ID NO 11
<211> LENGTH: 22
<212> TYPE: DNA
<213> ORGANISM: Homo sapiens

<400> SEQUENCE: 11
gcaagaagac cagtgactga gg                                           22

<210> SEQ ID NO 12
<211> LENGTH: 22
<212> TYPE: DNA
<213> ORGANISM: Homo sapiens

<400> SEQUENCE: 12
ctgctcttct tcagcaactc ag                                           22

<210> SEQ ID NO 13
<211> LENGTH: 20
<212> TYPE: DNA
<213> ORGANISM: Homo sapiens

<400> SEQUENCE: 13
gatgccacgc ggcttgtagg                                              20

<210> SEQ ID NO 14
<211> LENGTH: 23
<212> TYPE: DNA
<213> ORGANISM: Homo sapiens

<400> SEQUENCE: 14

-continued cttttctgc accaaacgca ttg          23

<210> SEQ ID NO 15
<211> LENGTH: 23
<212> TYPE: DNA
<213> ORGANISM: Homo sapiens

<400> SEQUENCE: 15
cagccaagaa gttctgagtc ttg          23

<210> SEQ ID NO 16
<211> LENGTH: 22
<212> TYPE: DNA
<213> ORGANISM: Homo sapiens

<400> SEQUENCE: 16
atatcagcca gagatctctg gg           22

<210> SEQ ID NO 17
<211> LENGTH: 23
<212> TYPE: DNA
<213> ORGANISM: Homo sapiens

<400> SEQUENCE: 17
gcatcccaat tcaacacgtg ttg          23

<210> SEQ ID NO 18
<211> LENGTH: 21
<212> TYPE: DNA
<213> ORGANISM: Homo sapiens

<400> SEQUENCE: 18
cttctcagct gaaacttcct c            21

<210> SEQ ID NO 19
<211> LENGTH: 23
<212> TYPE: DNA
<213> ORGANISM: Homo sapiens

<400> SEQUENCE: 19
ccagctcacc ggatcatggc cag          23

<210> SEQ ID NO 20
<211> LENGTH: 25
<212> TYPE: DNA
<213> ORGANISM: Homo sapiens

<400> SEQUENCE: 20
ccttccttac tggtcctcac atctc        25

<210> SEQ ID NO 21
<211> LENGTH: 21
<212> TYPE: DNA
<213> ORGANISM: Homo sapiens

<400> SEQUENCE: 21
cagttgtgag ccaccgtacc c            21

<210> SEQ ID NO 22
<211> LENGTH: 20
<212> TYPE: DNA
<213> ORGANISM: Homo sapiens

<400> SEQUENCE: 22

```
cgatagttgc tggcccctc                                              20

<210> SEQ ID NO 23
<211> LENGTH: 20
<212> TYPE: DNA
<213> ORGANISM: Homo sapiens

<400> SEQUENCE: 23
gtgcccttcc cttacccatc                                             20

<210> SEQ ID NO 24
<211> LENGTH: 24
<212> TYPE: DNA
<213> ORGANISM: Homo sapiens

<400> SEQUENCE: 24
gggtaccagt agtcagggac ctta                                        24

<210> SEQ ID NO 25
<211> LENGTH: 27
<212> TYPE: DNA
<213> ORGANISM: Homo sapiens

<400> SEQUENCE: 25
acagtgtggc catcctgctc tacctga                                     27

<210> SEQ ID NO 26
<211> LENGTH: 23
<212> TYPE: DNA
<213> ORGANISM: Homo sapiens

<400> SEQUENCE: 26
tggcctgaat aattgcagta gct                                         23

<210> SEQ ID NO 27
<211> LENGTH: 22
<212> TYPE: DNA
<213> ORGANISM: Homo sapiens

<400> SEQUENCE: 27
gtgcgtcatc ccaagagtct ct                                          22

<210> SEQ ID NO 28
<211> LENGTH: 29
<212> TYPE: DNA
<213> ORGANISM: Homo sapiens

<400> SEQUENCE: 28
taacaggttg gaccaagcta tgcaggtga                                   29

<210> SEQ ID NO 29
<211> LENGTH: 25
<212> TYPE: DNA
<213> ORGANISM: Homo sapiens
<220> FEATURE:
<221> NAME/KEY: misc_feature
<223> OTHER INFORMATION: Sequence of Figure 4: 5? region  HA3

<400> SEQUENCE: 29
tgtccgcact cgtgacgagg accgg                                       25

<210> SEQ ID NO 30
<211> LENGTH: 26
```

```
<212> TYPE: DNA
<213> ORGANISM: Homo sapiens
<220> FEATURE:
<221> NAME/KEY: misc_feature
<223> OTHER INFORMATION: Sequence of Figure 4: 5? region  HA0 and HA5

<400> SEQUENCE: 30
tgtcaacact cggtggcatg ggccgg                                         26

<210> SEQ ID NO 31
<211> LENGTH: 548
<212> TYPE: DNA
<213> ORGANISM: Homo sapiens

<400> SEQUENCE: 31
tgtcaacact cggtggcatg ggccggaaga cacccggaaa actgcgactc taagagatca    60
agtcttactt tacggagctt acgacaggac ccactcagtg tagtcgggga gggcatacgg   120 gaagggagc gggattattc tgagaaagta cgggtaacaa agtcaggtgt gaggactgcc    180
gagacattcc gcccgtcctc ttcctcgact cctttactcc gggtctctcc ctccctctga   240
acgaactcca gcggccgtca gtcgtcccgg tcttgaccgg aggtcggaag gactgaaggg   300
acacgggcac aggggttcgg ggtcttcacc gggacgagtg gaactcggtc tgatagaaga   360
agtacccgtc gactttccgg cacacaacgg ttcggtgctt gagtaggtgt gcccgtgcac   420
gcacgcccag accgcccgtg gtcacgctac cacgcgacat gaacgccgtg tccatcattt   480
cctaccggcg cgacgtcttc cccggccagt ccccgtgacg ggaacggaag gactcacggt   540
gatgtagt                                                            548

<210> SEQ ID NO 32
<211> LENGTH: 118999
<212> TYPE: DNA
<213> ORGANISM: Homo sapiens
<220> FEATURE:
<221> NAME/KEY: gene
<222> LOCATION: (1)..(118999)
<223> OTHER INFORMATION: Homo sapiens genomic DNA, chromosome 22q11.2,
      clone KB226F1, Genbank accession number AP000351.2  GI:5420485

<400> SEQUENCE: 32
aagctttaaa ccaagtgcat ggcccttctg cgttgtaggc ccacaaggcc gacactgcta    60
ttcacatcct tgtatggtcc cctaccctgg agcgtggctg gggcctgtgc tctactgctt   120
ggaagcaagg cttatcccta agccttattt tcgggaaggt ggatttgaga gctactatcc   180
cacatccttg cttggtgccc tgtgaataaa tcttttctct tttgcaaaac tcgtgtcatg   240
gtgattaatt tactgtgcaa tgccaggcac tgttggaaac ctctggatag gcctcacagg   300
gcctcagcca tctcggggag gcgttagcta gagtgtaaca aatatgaccc cagcaactgg   360
ggagggacag ctcattcctt catgaggtgt ggggctggca gccccgcagg cagtcagcca   420
cccttcctct ctggcctccg tcctgggcac tgggcccagg cactgggcaa ggaggctgct   480
gcacctcctt tctcctcttc ctttttttt attttttgag acggagtatg gctctgccgc   540
ccaggctgga gtgcagtggc gtgagctcgg ctcactgcaa gctccgcctc ccgggttcac   600
gccattctcc tgcccagcc tcccgagtag ctgggactac aggcgcccgc caccccgccc    660 ggctaattt ttgtattttt agtagagacg ggtttcaccg ttttagccag tatggtctcg    720
atctcctgac ctcgtgatcc gccccctcg gtatcccaaa gtgctgggat tacaggcgtg    780
agccaccgcg cccagcctct cctcttccct tttagtggga aatatacctg cagcctagat   840
```

```
tcccagaaag gggtggtgag agagcagaca cgccactgat tgacccgaag ttctaggagc    900
caagggatga gtgaagaggg cgtggccgga ctcggggctc ctggtgaggt gcaccgctgc    960
aggctcggtg acccagcagt tcctgcccaa ccctcaccta cccccagccg ttcctgtccg   1020
ccgcccccaa ccagccattc ctgcccgcag ttcctgttcc cgggcctgtc cccgggtttg   1080
tccccagggc ccgtcccctg ggtttaggtc tgccctccca cgcccaccc cattgccccc    1140
gccatgggtc tgctgtccca gccctgccgt tcagtctaca tcttcgccaa gaatggcatc   1200
cccttcgagc ttcgcacagt ggagctgacc aaagctgggc tgggcaggca ggcccagggg   1260
atattggccg cggatccctg cctgtccccg ctgctttgca gttgggccaa gaatgcagac   1320
taacacgaag aatcagactc tccggtgtgg aaactattac ataattatct atgttattat   1380
ttttacttt tggagacagc atctaactct gtcactcagg ctggagtgca gtggcacaat   1440
catggctcac tgcagcctcg accttccagg cttaagcgat cctcccgcct cagcccctca   1500
agtagctggg actacaggtg cccaccgaca tgcctggcca atttattatt attattatta   1560
ttgagaggag gtcttgctgt gtttccgagg ctggcctaga actcctgggc tcaagtgatc   1620
ctcttgcctt ggcctcccaa agtgttggga ttacaagcat gagccgccat gccccactgg   1680
ttgtctattt taatagaggc ttgatctttg cttgtgaata caaaacattc ttcaaaatac   1740
aggtttagag agggcacagc aggcacagaa cgagggtagg gaaatggagt ggggcaagaa   1800
tatcttcacc ccatgtgctt ggaaaaaaca atgaaactgc ctcgttgttt cctaagtaaa   1860
atagtccctg tctaccctg cctgtgtctc ttccacttt gtattatttg tttgtttatt    1920
tatttattta tttatttatt tatttattta tttatttatt acagtgtctc aatctgcagc   1980
ccaggctaga gggcagtggc atgatcccgg ctcactgcag ccttgacctc tcaggatcaa   2040
gtgatcctcc caacttactc ctcctaagta gaatagttgg gactacaggc acgtccccgt   2100
gcccagctac tttttctt ggtgtgtgta gacgcatgat tttgccatgt agaccaggct    2160
gaccttgaac tcctgagctc aagtgatcct cctgcctcct ccttctaaag tgttgagatc   2220
acagacatgc accaccatgt ctggccctgg gtctcttcca cttttatgta tttcttggca   2280
ttcttctgcc tttttccttt cctgcatctg acttgctcta tcccatgggg cttctcaccc   2340
agctgaaggg gctactccta gaggctagag gctggaggc cctgtggcag ggcagtgggg    2400
gaggccagca ccctcaccct gagctccagc gtttgctggt ctggctggca tacagagatg   2460
cagctggagc acaattcagt ggaggaggca gggctataac taagcagtag ggcagagagc   2520
agagccagag cccctgggc aggccagagg gaggaccctg ctcagctgac tcttcccaac    2580
tgctgccctt ggtacaacca gcttgagtca cctgctacag aacagggct ggacacagaa    2640
gcagtctgtg gagggagaat gggcagggt gtgtatgtcc attcagtaga agggcaaaga    2700
ggcccacatg taggcctatg atcagactgg agcctggctt gactgaggtc ctctgatcca   2760
aacaccaggc acctaatgcg gcctctagca ctggcctaga gtgctaaagt gagtcagacc   2820
tgggaacccc cactggggag ggagccttga gagtttggca taagaaagca agaagagctg   2880
agccaccgga ggctaagtag ctgaatgggg cagggattcc cagcaagaat gaggttggtc   2940
tgagggttgg gaacatgttt ggctgggact ctggggtatt gacaggtcac ccagcctggc   3000
cagtagggcc taagtcccca gctgggatag gaagctgaat cagagggggc aagcctagag   3060
cccaggagg aggctggagg ggtctgacct atggatggaa ctggctgggg gtgggtgtg    3120
aattacagct ccagggaatt gtccttgagc catgcttcaa ggagctggac acaggaaaga   3180
tggccctctg atggggtcaa ggtctgtgac ccagtgacta gcagagaggc ttcctcttcc   3240
```

```
ctgatgcctc ccagataggg gcctcagaaa gctgctgctg ggattttggg gtgggggtgg      3300
gcagagacct cagagaactc tgggttatcc ccactcacct ctctgatctt tcctgcaggc      3360
cagcagcaca gcgatgcctt tgcccaggtg aacccctga ggaaggtgcc gggccttgaa       3420
ggatggggac ttcaccttgg ctgagaggta accggtccgt gggctgctgc cgggccttgt      3480
ggggccagtc ggctgtctgt tcactgttga tggcttggat catggactgt gggccctgca      3540
ccagccccag ggtgaagaat gggtggaggc aggcagaggt gcccagtgtt gacaagggtt      3600
atagaagtcc cctcctgcat tgtacaagtg aggaaactga ggctggagga ggggagggac      3660
ttgcacaagg ccacagggcc cagtctgctt ccgggcctcc tcaccgccag ccttcccctc      3720
cgaaaaaagg agagtgctaa gtttcgagga gcggctgtac caggcatctt agtgctacca      3780
ttttgcccac aaatcctgtg gggcaagtgc tgtttccctg gagagtcgag ggaccactca      3840
gcgagcttca gtggctattt gctaaacatc caccagggcc agaccccatt taagccctgg      3900
ggcttgagca gtgaacgtgt ctgcgtcctt ctcctcatgg atctcacatt ccattaatag      3960
aagggggagc tgacagtaac ccatgtaaac atgaacatat tcggatgttg atggatgcca      4020
tggaaaaaat aaacagggta agagtggggg tgtgtgtcat tatgagtagg atgctgaggg      4080
aagactccct ggaggaggtg gcatctgagc agggagctgt aggaatgtgc aaggcatgag      4140
gagaagggtg ttctcactgg agggaagagt gagggcgaag gctccaggtg ggacaatgca      4200
tggggttcag actggagagc aacgggccag ggtgggtgca gtgagcagga agagcaggag      4260
gtcacgacag agggagcat gggacactgg gaaggctttg gctcttaccg caggtggatt       4320
gagttgttgg agagttttga gcagaggaga actgtgatct gacttacgtc gtaaaggatc      4380
cccctggcag gggtgagaaa gccactgcag tcatctggca tgcagcgctg gagccccaga      4440
ccaaggtggt ggtggtgcag ggttgcgggg gattgtggtc agttctgact tttattgaaa      4500
tctaactgca gggtttgctg aagggttgga ggtgggtggg aaaaatgaaa gccaaaacca      4560
gcctccaggt tggtggccgc atggtggcgt cctttaccga ggccacatag tgcctccttg      4620
gtggagctgg attcacattc agagcctggg atcactggat ggtccaacac ccataaaggc      4680
atgatgagct ctgagggtca gactgcacaa cccttcacca taggtgaacg ggagttggga      4740
cagggtggga agcaatgctg ccatgtcacc tggaaggctc tgtccctgct ggccttgctc      4800 ctggcccctgt ccacactttg gatatgttgg ggagatatcc aacatgctct cgttcttcag     4860
actcacactg ggtgcccctt cctcctggaa gccttccctg agccctgct gaagttcatg       4920 acattttgtt tcttccttgc tgcccttagt tgagatgaca gtctggcccc gtgtagggct      4980
gtgtgaccct gggtagttac ctaacctctc tgagcctcac atccctcctc tgcatcatgg      5040
ggatagtgaa aatgccccag aaaacggttg aagagtgttc agggcatgtc ttctgcccct      5100
gccatgtccc cccagtgtgg ctagcttgct ctatatgagc tgcatgtaca aagcacctga      5160
ccactggtac ctccaggacc tgcaggcccg cgcccatggg gatcagtacc tgtcatggca      5220
gcacatggcc ctgcagagta gctgctgctg ggccatgtgg cagacggtga gccatggagg      5280
gcagggacac ctcccgggat gcccaaggga tgctgctttc actttacaaa attctgttta      5340
gacctgagac caaatcctgg aatgccagag actgcctaat tcaccaact tgtttcatag       5400 gagggaaacc aaggaccaga gccaaggaag gattcccct atgtgcctta attccacagc       5460
taccacctgc acacttacac tcacacactg ttcgacacac agccacactc acacacacat      5520
ccacccacgt ccacccacag tcacacgatg tatcacattc acacgtatac acccacacac      5580
```

```
acaatcataa catttacaca cagtcacaca gttaactcct atacacacat atacacccac    5640
acaatcacac aactcactca tattcaacaa agtcacacaa ctcactcaca ttgacacaca    5700
tacacaccaa ccccacacac aattcacata catacacaca catatacacc cacatacaca    5760
accacaccat tcactgacat taatacaaag tcatcacaca gttcactccc acacacacac    5820
atacacctca cacacacagg cacacaattc acaccaacaa aatcacacag ttcactcatt    5880
cacacacata cacccacata cacaaattca cactgctcag tcacatttac acaccattca    5940
aattcacaca catatacacc tacatacaca cagttcactc acatcacaca catatacacc    6000
cacatacaca cagttcactc acatcacaca catatacacc cacacataaa cacagtcaca    6060
caattcactc acgttcacac acacagttca ctgacattcg cacacataca cacacaccac    6120
acacaggcaa ttcagtcaca tggccgaaag ccagtcctta ccttcctata gttcctttcc    6180
cagtgtcacc tcagcctttg gccctcagcg tccccttccc atgcctggac tgcggaagag    6240
ccctgaacac accccatctt catgcctcca gcgctagccc gagcccttcc ctctgccaag    6300
agcactaagt gcaactcaag atcacttcta gggacccttc cctgcccctg ctgccaggtg    6360
acctgaggat cctgctggtc ccgcttgaca atgatgcaca gcatggttag ttcagctgag    6420
gtcgctctcc cagacttact gccacctaca cagcactagg actgactgtt taactttatt    6480
ctttatttcg tgtactttat tggagtgtct gttgaaagca aaaccatcca ataaggaaca    6540
atcccaaggc agccagcatg gatcaagaag gcacaggctg tggccgccat ccccagtgcc    6600
tgatggggag aggggtggt aatggaaaag gcccaggaaa gcaggccaga gtgtccctca    6660
aaatatgaga aatcactgga agagagagcc agaatgggac ctaagacaga agccaccacc    6720
aggcaccctt aaggcaggac agttgcaatg gttacttgga atacttccgg ctaggagtgg    6780
tgttgcggga agtcagggac cccaaacaga gggaccggct gaagccatga cagaaaaacg    6840
tggattgtga agattttatg gacatttatt agttccccaa attaatactt ttataatttc    6900
ttatacctgt ctttactgca atctctaaac ataaattgta aagatttcat ggacacttat    6960
cacttcccca atcaataccg ttgtgatttc ctatgcctgt cttacttta atctcttaat    7020 cctgtcaacc aaggaggatg tatatggcct caggaccctg taataattgc attaactgca    7080
cacattgtac aggatgtgtg tttgagcaat atgaaatgtg ggcaccttga aaaagaaca    7140 ggataacagc aattgttcag ggaataagag agataacctt aaactctgac tgctggtgag    7200
ccaggcggaa cagagccaca tttctcttct ttcaaaagca aataggagaa atatcgctga    7260 attcttttc tcagcatgga acgtccctga gaaagagaat acgcaccagg aggtatcagc    7320
ttataaacag caccccctggg cgtggcctgt ctcttatggt cgagactgca gagatgaaat    7380
atactccagt ctcccatagc actcccaggc ttattaggaa gaggaaattc ccacctaata    7440
aattttggtc agaccagttg gtctcaaaac cctgtctcct gataagatgt tatcaatgac    7500
aatggtgccc gaaacttcat tagcaatttt aattttgcct cggtcctgtg gtcctgtgat    7560
cttgccctgc ctccacttgc cttgtgatat tctattaccc tcttaagtac ttgatgtctg    7620
tcactcacac ctgttcgcac actccctccc cttttgaaaa tccctaataa aaacttgctg    7680 gttttttgtgg cttgtggggc atcacggatc ctaccaacgt gtgacgtctc ccccggatgc    7740
ccagctttac aatttctctc ttttgtactc tctccctta tttctcaagc cggctgacgg    7800
ttaggaaaaa taggaaagaa cctacgtgat tattggggca ggtcccccga tagagtggca    7860
catgatgggc acagggcagg cttgggaaat gggggccgt aaggcacaa gacatgtggg    7920 caggtagccc agagtgtgtc tggaacatcc tgtttattgg tcggcagtga catctactgt    7980
```

```
cacatttgag aactgcatcc acagccacat gacctcctgt gaagacctca gggcaaactg    8040
gggaaacctg cccttcttgg aaggtgatac taggggggat gagcaacacc tttcttggag    8100
gtttgaattc ttcagggccc ctccagcatc ttggtcttcc taattcctcc cttgatcccc    8160
cagccctagg ggtggtagct tcttgcagtg tttacctccg tgttaatctg gattctctct    8220
gtcttcggag ttctctaatg cctggttacc aattctttat atcaagttct ctccgttaaa    8280
atcattgtgg tggggtccat cccatggata tacatggagg tctgtgtgac aatgtataat    8340
cttactattt gcagttatta caaaactgtc ctagaagaca tgaatgcttg ttaaaagaaa    8400
tcttttaagt ttcctagact tcaaagaccg ttgctatgcc ctgtgaaaca tcgcctatat    8460
cctttaacag tttgcaattc gaattggtta cttacttaac attttgttgc cctggtgata    8520
caattatgtt gactcgttat tgtgaggtta ctttgttatt aaccatgatg aggattacta    8580
gcacatactt ttactccata tgtataacac aacaatgtag taaaaccaat aactcttggt    8640
tctctattca aagtgtttgg aatctttatt ctgtttaaaa cactgatgac atttgccaat    8700
ttttgagtgt tcttcatgtt actgatttgt aggagctctt tatatattgc agatttagtc    8760
tcttactggt tatgtatgct gcacctgagg agtagcagca ctgccaagga cactgagtgt    8820
cttgtctgtg cagagcttca catgaagctg gagagaaggg actggggcaa gagggaaaga    8880
taaaaagggg caagtaagta acagaatgaa tccttgttgc taatctcctg gcccccatcc    8940
cagacccttc aggggatcct ggcgattcga agcagcatag cctgataggc ctctggtgag    9000
ggtgttggga gggttttctt ggccgcctgt tccaggatgc tcaagatgat gctgtgggcc    9060
tcctggcata gctcagcacc caggaaagcc tccactcgtc cacgccatgc tgccagtcgt    9120
ggccgtccct caaacagttc atagccgaga gccaccggct gtagggacaa ggatgaaaaa    9180
gttgtgggca tacaactttc ccagttgtca ctgccgaccc gaatgctgga accatgggca    9240
gaagtatcag agacatggtc cattccccag cccctaagtg aatggaccac aggggcccag    9300
gcagtatgtt cagccttaga gcccaagagc agccagggtg agaccccaca cccaggcagg    9360
aggcagaagt tcagggttct ggccccagat catccagaga cttgctctat gattctgggc    9420
aaagttctgg ctttctccag gcctcagtgt ttctgtctgc ctcatggggtg tgacacgaag    9480 agggacactg cccacaggct gagctcacac ctgcatcagc tcctccaggg ccatgagatc    9540
agccagtgtc acctgctggc cagcgaggaa gggcctgtcc cccaggaact tgtcctccag    9600
ccattgcagg gcctggtcca tggcagtcct gttgcgttcc accttctcct cgggcacctg    9660
gaccccaatg aggggcccca acacctgatg ggggcagaga gtgggtcagt ctatggcccc    9720
ggcctactgc caactactcc ctgatggcca atcactctcc agatgctctc ctcacctgg     9780 acccacaggg gtataccaaa ggtgccacgg atgcagtcgg catgccagcc caggtactca    9840
tgaacacggg cacgagcctg caggtcagat ggataccagt ggtccggcgt ctggtactta    9900
cagctcaggt aaatcaggat ggccgagctg ggaacaaatg ggcagtggct ataaggacac    9960
tggcaccagg catttacccc taactgctcc catctgccag tggggcccgg gggcttctct   10020
gcatttgaag gactgccctc cagcctcgcc ctccatctcc agctccccaa caccaccccc   10080
tcctcctacg agtctcctcc tgtctttgtt gccttgggca ccgactcttg gctggacctt   10140
ctgctttgca ttttgagaac ctcatctctg tgatatgcca gcagccgccc tgtgaggtag   10200
acactcctgt tagccttttta gcacaagaga aaactcaagg tcagaatggt caagtgactt   10260
gtccgaggcg gtgcagctca gaataggctc cctggacccc tggaaccctg catggggctg   10320
```

```
gcacacagtg gatgctccgt ggagtccctt gcatgtccac gcgcttgggt cagggatcac   10380 gagggga gga atgtctttgg ccccgtctg acaggcccc agccatcact tctgcagcca   10440
cctgacctct tgtccttttc ctgcccagca gctggacctc accatgagct gtgcccttgg   10500
gccatggcat tggcctctag gcccggcctg gtagattgg gtagtctgcg acaagtcact   10560
agaggctctt ttcagctagc atttgttgaa caaatgcgca acagtggaaa aatgttccct   10620
tgtcttctct tctaataccc ttcagtctgg gagtggagag gccctgcggc tcagaaaagg   10680
ctggaagatg agaggtgggg ggacatgttc tgtcagcccc tgctcatccc ggtcacaccc   10740
caagctgtac cttctcccca gatacctctc ctttctttct ttcctttttt tttgagacgg   10800
agtctccctc tgtcgcccag gctggagtgg gctccctctg tcacccaggc tggagtgcag   10860
tggtgctatc tctgctcatt gcaagctccg cctcctgggt tcacgccatt ctcctgcctc   10920
agcctcccca gtagctggga ctacaggcgg ccgccaccac gccctgctaa tgttttgtat   10980
ttttagtaga gacagggttt caccgtgtta cccaggatgg tctcgatctc ctgacctcgt   11040
gatccgccca cctcggcctc ccaaagtgct gggattacag gcgtaaacca ccgcgcccgg   11100
cctttttgag acggagtcta gctctgtcgc ccaggctgga gtgcagtggc gcgatctcag   11160
cacactgcaa gctccgcctc ctgggttcac accattctcc tgcctcagcc tccagagtag   11220
ctgggactac aggcgcccgc caccacgccc ggttaacttt ttttccattt ttagtagaga   11280
cggtgtttca cggtgttagc caggatggtc tcggtctcct gacctcgtga tccgcccgcc   11340
ttggcctccc gaagtgccgg gatgacaggc gtgagccacc gcgcccggcc agatccctcg   11400
cctttcccct ccctcgctgc cccatggggt atgggagggc cactgggcc cggggccagt   11460 ggggagagcc aaggtcacat gggctccgga tgcggtgagg ggtgagggaa ggagggcacc   11520
tttcagtcaa gatgaaatca ccatccttga gcgtcggcag tttccccagg ctgttgatct   11580
gcaagaactc cttgctcttg tgctgccctg aagaggaaga agtcagaaaa ggtcttcaga   11640
ataaaaacgc tgcacctcta caccctccct cctcctcccc aagcggagcc ccacagccct   11700
gagaaacagc aaggtctggg actagaggcc tggatcagcc tcactccctg gctgggcctc   11760
cctgccctgc cacattccgg ggcagctggg gggttttggt gggtggggcc aggtgcagca   11820
ggtggataaa gagaagtttt ctagccggac tctggtgggc caggggaggg gaggcaaact   11880
ggggtggctc atctcttccc atctcttaat tctcacaaca gtatgtcctt cttcccgagg   11940
tcttctgggc tttgtgaatt tatatgcgtg cattccacgc aagaactctg tcaactccat   12000
tcagtatttt ctttccatcc ctacagagca gaaggtaacg ttatcctcct tttcagaagg   12060
caagctaagg ttcagagagg ctgtgatccc ttcaaggcca ctcagtccac agcattctct   12120
ggtggcagac gctgcaggag gaggtgaggg ggctgtgcgg gcggcgagac gctcagggca   12180
gagcagggcg ggggcctggg ggtgcactgg gtttgtggac acgcgggaa acgggctggg   12240 cccaccttg accaaatcca cggtgcgcag ctctaagggg atgccattct tcttggcgaa   12300
gatgtagacg gcgcggctgg gctgggacac caggtcaaga aacagctcta ggcccatggc   12360 ggggcggca aggacagcgg ggatggcagt gaaggcgctg agcgcggtgt gggcagcagc   12420
tgtggcagga tccgcgcgcg ccggaaata ggggatcagg ccccacccc tggggacagc   12480 acccaattgg agcgcaccac ccccggaccc gcctcgcccc ttcggttcct gtccagtcct   12540
gccggccaag actccaccac cagatccgtg cgtccctaca gggagggcgg tcgctatgaa   12600
cgcacagctg ggaggtgga gttggagctg ggaccctcg actggcaggg aggacgcgga   12660 tgcaggggc cgactgcaag gggaagggga accggctgga cagggagaag caggtctgct   12720
```

```
tttcgggatc cggtgccag ggaccctgcc cagttccagg cgtcgccctg acccagaaac    12780
gactgggcgc cgccgtcctg gaaaggcccc agcgcacgga catctgaggg ttcgttcaga    12840
gctctgtttc tcggcgctgc atggtggcgg aagggaggga gcgaatggga tccctaaaa    12900 gggatcttag agtttcaccc agtgggatgt gacacttgca ggtgtcccaa actggtggga    12960
accttgactg gaaggctggg gttaaggatg aactttctgc cgtccagact gtccctgca    13020 gagcagctgc tgccagacag cgggagctgc cagacagcgg gagctccac ttcgtgcaca    13080 ggatggggc agggagcccg cagccgcggg aggcaggaat gactgtccgg gaacctcctt    13140
tcttctccct gaatcccagc cctggcatct caccagggg cacagtgatg gtccagggct    13200
gggcccggga ctctagctga atctttcaga gtatcccatc cctctggcca gtggcccaag    13260
cgagtgaacc agaatgcttc cttgggagtt ttgaaactgg aactggagag aggagctccc    13320
tatggggagg taaacgggag ctggggccac ctgtagtgac atttcctgag ttcgaggagt    13380
agacgagact gagagagaaa agctgactca gagaaaggga gtgataacag ggcatgctgg    13440
cccacacctg caatcccagt tactctcacg ggatctgttt ctctgatgtc tgggtatgaa    13500
aggactttct aagcctcaga acagtgggag aactcaacaa agaaaaaacc aatacatata    13560
caaggttact ttgtggagga aaaaatggat taaccttaag caaaaaactg ggaaggatct    13620
cggtaaaaga tacgtcagaa ggaagtaatg tcctttaaga tgttcttaga acccatcag    13680 acaggtgggg tgtggtggtt cacgcctgta atccctgtac tttgggaggc agagatgggc    13740
ggatcagttg aggtcaggag tttgagacca gcctgggcaa cacggtgaag ccccgtctct    13800
actaaaaata caaaaattag ctgggtgcgg tggcacactc gggaggctga cagggagaa    13860 tcacttgaac cttggaggca gaggtttcag tgagctgaga tcataccact gcactccagc    13920
cgggccactg agcgagactg tctcaaaaca aacaaacgaa caaacaaaaa gaagagaaac    13980
tcatcagacg aagacacagg aaaaaatga gcgaaggaaa tcagcagagg tttcattgaa    14040
ggacaaagag aaatggtcaa tacatggatg aaacatgtt taacttcagt aataatcaag    14100
gaagcacaca ccaacacaac atgcacatac tgttttttatt tatcaaaggc acacatattt    14160
ttgaaatgag tactcctaat taatatgtac agagcactta cccagtgccc agcacagggg    14220
tggcaccctg tgtgtgagac agcatgaaac aggtagacac gcgccctgct gaaagtaagg    14280
gaccgcctct ctggaggatc catcgggcaa taaggaggtt tccacacctt aactgtgtct    14340
gccttgacct ctggggcctg ggagcagagc cccctccagc tggtggggaa ggaagcgtgg    14400
tgtgtttgag gacagaatgg agagaagttg agtagagcaa gtgtagactc ttcctatcca    14460
aagtgtggtc aatggactgg gagtatcagc atcaccaggg agcttgttgg aaatgcagag    14520
gctcaggccc cactctgacc ttactgattg ggagcataaa ctgtaaccag attccaggga    14580
ggattcatac acacattccc gtttgataag tgggggtag taggaggtga ggtgaaaagt    14640
ggggagggga tggctaccgc actggagaag gctggctttg tgttgaggcc tttctcatga    14700
gggcagtggg gagccatgga aggctttatg caagagaggg tacgggcaga ttgagattac    14760
agaaggatcc cactggttgc cttgtgtgag gacccaggga aaggggggag gctgtccctg    14820
tttgagtagg agatgagagc tactggtggc tatgagtgga aagaagtgag cagaggtgag    14880
cagaaatccc aaggactggt gatgataagga tgatggtggg aaccaggatg ggctttgggc    14940
agaccctgac ccctctctct gcctgtcggc ccaccagata taatccctg tgttcctggg    15000 cgagtcagtg ccacccgaga tgttggcggc cactttggct gagctggacg gatgcctgca    15060
```

```
gctgctcgag gacaagttcc tgcgggacca ggccttcctt actgggcccc gtatctctgt   15120
ggctggcttg gtggcaatca cggagctgag gcatgagagt gccatggggt gcggtggccc   15180
gctgggcagt ggtgtatccg ggaagggagc tgacatccca gctcatgttg tcttttctgg   15240
ctgtgggacc ctgtgtgagt cacttctcct tctgagcctc agtgtcctca tctataaaat   15300
ggggctttac aaacccctca ccgcagctat attaagaggc ttccaagtgt ccccagggag   15360
ggggacatcc tagcccatca cacacatggt ggaggaggga aaatccaatc agagaacccc   15420
taaagcaggt catgctgcct tacacttggc tatgcccagc ccctccgctg actctgtctt   15480
cccctagccc atcagtgctg gctgctgagt ctttgaaagc ggacccacgg tggcagcatg   15540
gtgcccaaca cgtggaggct gcagtgcggg aggacctctt ccaggaggcc ctcccagctg   15600
tcctgaaggc caaggacctg cctccagtag aacctgctgt taaagagaat ctgaagacct   15660
taatgcagct tttcttgctg tgagtgcgtg tcccacactt gctgagccac tgaggggatg   15720
ctgtgttggt agaataaaga catggagctg tccgtctcct tggttgaaga aagacatat   15780
ctgcaaaggc tctggtccac agttcctcca gatatcatgc ctgcattcct tttgtctcct   15840
accccattcc attctagctt ccatgtgacc tctgaaaaga gcttgggcaa acgcttactt   15900
gaccctgacc ttctgtgtgg aactttgtat ggttcctcac tgcccagaag ctaaagtaca   15960
agtcattgaa ctttgcattc aaggccttgc tcccactcct ccaggtggcc ccttctgcct   16020
gcacactcct aaccctctc tgggctccca ccttggcctc ttggcctccg ctcatgctgt   16080
tccctcctca tcttcgcctg gtgcccttcc tggtcttttg gcatttggca ccctgtctct   16140
tctccaggga gacttccctg acctccccag ccccagtcca ggtcaggcga cctctctggg   16200
ctcctcagcc ccagtgtttc cttgcggggg ataccccgg actgagcatg tatcatcgat   16260
gaggggtgac ctggtggaaa gatgtctgaa tcaggatcag ccttggtctc ctcggtctct   16320
ctcctcactg tgggcgatg ttgtgttcca caagtggggt gcaggctgg ttcatgaacc   16380
tccttgcagg aagggaagtc cctggttatt tcctggccct ctcccatgcc tcctcataac   16440
cttgaccaca gtcttctcta caccccactc ccggaccact ggcttgtcca tgccccacac   16500
ctggtcccag acttgccacc tgtccctgcc ctctcccctt aggactgtca tatttacctg   16560
tcgtgtgtct cagaccttct gatatctgag tcatctaata aacaaactgc taataggaca   16620
agatcatgac agacagagac tctgtcggcc tttcagtgga ggctccttta agtatgcaca   16680
cttatagaga atttataca cgtagttgaa attgtacata taaacttgca aattttttct   16740
ttcttttttg tgggggaggg gggagcctgg gtctcactct gtcatctagg gtggagtgca   16800
gtggcacagt catagctccc tgcagcctag atctcctgcg ctcaagcaat cctcctgcct   16860
cagccgccca ggtagctagg actacaggca cacaccacag cacccagatt tctttctttt   16920
tttttttttt ttttgtagaa aataaagaag agaatcttgc tatgttgcct agcctgatct   16980
ttaactcctg ggctcaagca atcctccctt cttagcctcc caaagtgctg agattacagg   17040
tgtgagccac attgctcgac acaacttca gtcatatttg taatgtacaa ttcaagtgat   17100
tttgccacac tgaccacact catgtttaag ccacgccaac agagttccat gttttctgat   17160
gttttttcga gatggagtct cgctctgtca cccaggctgg agtgcaatgg cgcgatctcg   17220
gctcactgca acctccacct ccccggttca agcgattctc ctgcctcagc ctcccgagca   17280
gctgggatta caacgtctgc caccacgccc ggctaatttt tgtatcttta gtagagacgg   17340
ggtttcgtca tgttggccag gctggtctca aactcctgac ctcaggtgat ccgcccgcct   17400
ggacctcgca aagtgctggg attacaggcg tgagctaccg tgcccggcct ttccatgttt   17460
```

```
taaagaacat attttgccac ccctggtgg acagtggctc accaccggca caagaggcta    17520
cacaggcaga tgtcaatggg gaccaggcag ggacaggtat tgtcgtgagc ctagccctac    17580
ccgcgccccc gcgagtaacc acatctcctg actgcccaag cgcagatttc catactgaac    17640
atgaaattgc ctgacttcga aatggtggca aatcattcaa aaaaacttta agctcccgtt    17700
gtattggtta ttagggtcga gcctggggaa accccctata ggtgtgtgtg tgtccttgtg    17760
tgtcgggggt gtggtgttca gacctctaat agggctagga accgggcgac cacagcgcgg    17820
aagcttgaga gggaaaccca cctggcgcca ggcaggaggg tcggggggaga cagggtgggt    17880 ccactaccgg gttaaagacc tgtagtgggt ggggctacac gtagggcgga gacgatggga    17940
cttccggaaa tcagccggca cacgtgactt ttgtttgcag aagcgggagg tacccctaggc    18000 agccaatcgg ggagcgccga gtctctgtcc agccaatgag aagccaggtt gctgtggcgc    18060 ctcgccctc ctccctggtc cgcgagcctt gggtacccc agcttttctt ccgccagagc    18120
tgtttccgtt cctctgcccg ccatgccgtt cctggagctg acacgaatt tgcccgccaa    18180 ccgagtgccc gcgggctgg agaaacgact ctgccgcc gctgcctcca tcctgggcaa    18240
acctgcggac gtaagcgtgg gccgggcagc acggggcgag gggaggttgg tgggccaggg    18300 gtccggcct gtccctgctc cgcctccccg acagtgaccc cgaatctttt ccccagggac    18360
cactccccac tccttttcctc acgccaagct ctgactttcc gtgctccacg atcccgcggc    18420 tcccctccg cacgtctttc ccttgtcgcc ctccccagtc atgacccggg cgtgaccttc    18480
agggaccgcg gccccgtatcg ggatccctgc cccgcgaaca ctgcgcgttt cggctttcgc    18540
gcgctcgggt cccgtcccca gaggtagccc ggccggctcc aacttcgggc aaaactttc    18600 atgtccccct cagcgcgtga acgtgacggt acggccgggc ctggccatgg cgctgagcgg    18660
gtccaccgag ccctgcgcgc agctgtccat ctcctccatc ggcgtagtgg gcaccgccga    18720
ggacaaccgc agccacagcg cccacttctt tgagtttctc accaaggagc tagccctggg    18780
ccaggaccgg tgcgtagggg tagtagggga tccatgtggg actgccgcag actggagcca    18840
ctgatcctgc ctcaggggga aaaacccatt tcttgccctg cccagtaagg acacatcagg    18900
gtctggagct ttgggggcccc ctgacccctt aggttcctgc tgttaggacc atcttcaaag    18960
tgcgagcagg attgaatgaa tttctggctc tgctcctcag tgtgtaagtc tgtgaaccgg    19020
gaaggctctc ttttaacacc cccgggcgcag tgcaagggtc atgtgggatt gtctgtgtgc    19080
tgtacctgcc ttggcacctg acagggtagg tacacgtggc tgaagtgtga tttttctagaa    19140 cttttccagg ctggtcagaa ggaattctgg gtatgttctg aagttacgta ttttggacct    19200
gtgtcccagc caggttccag gtgaagttca cgggagactc acagagtagt gaaagaccat    19260
tggcctggat gtctagacat ctgctttctg ggtcctgcat agctggggga ccccagacaa    19320
acttggaaat gaaccatctc cagttggcaa cctcctcttc tgtgaataca ggggaaaaga    19380
cctccctccc ccacaagaag cgtctgcaac ccaaacctgg cgttctgtga ccgagttaaa    19440
gtttcctctt gggtaaaaga tattcttgag ccacatccat gtctaggagg aagtaagggc    19500
atgagaagct tgaaaggaca ctgtccaggc acggtggctc atgcctgtaa tcccagcact    19560
ttgggagacc aaggcgggag gttcatttga cccaggagtt gtagaccagt ctgggtaaca    19620
tagtgagatg ccatccccca aaacagtttt aaaaattaac cggacatggt ggtgtgcaca    19680
tgtagtctca cttagttggc aggctgaagt gggaggatgg tttcagccca ggaggttgag    19740
gctgcagtga gctatgattg cgcattgcac tccatcctgt gtgacagtga gaccttggct    19800
```

-continued

```
cacaaaaaaa gaccttctga aatggagcct ttgttagtcc atgaaggtcg atgaggaatg    19860
gctgatcctg ctgggtcctc cctcaagcta cagaggaata atacagtcag cccctgtat     19920 cactgggtta cgcatctgtt gattcaaaca accatggatt gaaatattag aggaaaaaaa    19980
attgataatt gcatctatac tgaaaatacg tatagacttt attccttgtc attattccct    20040
aaacaataca actatttaca tagtacgtac attatattag gtattataag taacccagag    20100
attatttaaa gtatatgaga ggatgtgtgt aggttacatg caaatattac accattttat    20160
gtaagggact tgagcaaatg tagattctgg tttcctctgg ggattctaga acaaatctcc    20220
cacggatact cagggaaaac tgttactcta acaacaagtg ttatacactt accatgtgct    20280
aggtcctcta caggtacttt acactcatga tcccatttga tccttacaat ccctatccac    20340
tctccctttg ctcagacaag acatgctatc cccatgaggt agataatctc cattatgcca    20400
attttatgat gagaagacta aggctcttca tactcccccg ccctcagcca ggctgtccca    20460
agctgtggcg ctcctcactg aaaactgctg tcacctctga gagggcatg ttggcttatg     20520 gcacagacat tagtggtggg ggggccaccc tgtgcccaac cttgagaaa acaggtgtct     20580 gaggtactgt gtccttaggg agtctgcaat taggaggagg cagattgccc ctcagcccac    20640
agactgacag agatgatgga gtgtgcagca cacgatga ggctactgtg ttgagtgtct      20700
gtcctaggtg ggtcatgctg atgtgcagcc accattccac acctgagtgt cccactgccc    20760
tgctgggggt tggggaatgc tcattaccgg gatgagcact tttgcaaaat gggctgaggt    20820
gggaggatca cttaagccca ggaattcaag accaccctgg gaaacaaagt gcgacccat     20880 ctctacaaag tcatacaatt agcccagcat ggtggcatga gcctgtgatc caaactacat    20940
gggaggctga ggcagaaggt ttgtttaggc ccaggaggtc gaggctgcaa taatctgagt    21000
ttccaccact gcactcactc catgctggct gcctttggat tgttcctaat tggatggttt    21060
tgctttcaac agacactcca ataaagtaca cgaaataaag aataaagtta aacagtcagt    21120
cccagtgctg tgtaggtggc agtaagtctg ggagagcgac ctcggctgaa ctaactgtgg    21180
tgtgcatcat tgttaagcag ggccagcagg atcctcatgt cacctggcag gaggagggac    21240
agggaagggt ccctagaagt gaccttgagt tgcacttagt gctcttggca gagggaaggg    21300
cttgggctag tgctggaggc atgaagatgg ggtgtgttca gggctctcca gcagtccagg    21360
catgggaagg ggacgctgag ggccaaaggc ggaggtgaca ctgggaaggg aactagcaag    21420
gtgaggactg gcttttggcc atgtgactga attgcctgtg tggtgcgtgt gtatgtgtgc    21480
gaatgtcagt gaactgtgtg tgagtgaatt gtgtgtttat gtgtgggtgt atatgtgtgt    21540
gatgtgagtg aactgtgtac atgggtgtat acgtgaattt tagtgaattg tgtgtaaatg    21600
tgagcagtgt gaatttgagt atgtgggtgg ataagtgaat tgtgattttg ttggtgtgaa    21660
ttgtgtgcct gtgtgtgacg gggagtatgt gtgtgtgtga gtgaactgtg tgatgactat    21720
gaatgtcagt gaatgctgtg attgtgtgtg tgtgtgtacg tgtgtgggga tttggtctat    21780
atgtgtgaat ttgagttgtg tgactttgtt ggatgtgagt gaattatgtg actgggtgta    21840
tatgtgtgtg tacacgagtt aactgtgtgt aaatggtatg attgtatatg tgtgtgaatg    21900
tgatgaatcg tgactagatg cgggtggatg tgtgtatgtg catggtgtgt ccatgagtgt    21960
gtaagtgtgc aggtggcaca gttgcaacag gagagaagac acaggaagcc ttacctgcca    22020
ttcatccccc cagctgtcct cccagcctgg ggacccctgg gctggaaagg ttatgaaaag    22080
tggtgctact gccaggaagg ggtgatgggg cagctggag acggtttga gtcttgccaa      22140 agggagggag tcgaagcttg caaccctggg gaggaggagg ggcagactgg ggaccctgct    22200
```

```
tctggaaaac cagcgaccaa cccccaaagg gacacaggca accccctgcct ccactctaca   22260 gtggggaaaa ggggagagtg gcgtggcagg ctgcccagcc agtcatggag ggagtagact   22320
tcaggaggag tacagaggtc tggtcccatt ttggggctga ggacaggagc ctcaggtcag   22380
cagtctgcag gaaggcccca gctggaccag ctgctcacac cttcccacag gcctgcagat   22440
gggtgtggag agcagagcct ccaggctgag tctcccagcc ccagatctga gcagtctaaa   22500
tcatccccct ccaggttccc tacggtctta tccaccagcc ctgctgccca tggtggcccc   22560
agatgcccag gagagataat agaaggtaag aagtcatgtt tgaatgagga agctctcttc   22620
atttatttca tatgaggatg aagaagagga ttatgtgatc acaggaatgt tgcatgcggg   22680
ataatccaaa gctggttatc tccaggccct cactctgcca agagatctct ctggaagaag   22740
cagccagttc acagatgccc tggatccctc cgtgcccaat cataaaaaag tcatgaccgt   22800
ccctatcttg ccaatctgcc aggactccaa ggggaaaaag cggataagta tccttcagga   22860
gacagagaaa aagatatcat cagctccttg gctaatacca catcttgcaa gaccccctgcc  22920 aggtactccc actgtgggta ctcaggacag cctgcctcag tccaccaggc attttgcaaa   22980
cctgctcatc ccaataatga ttttccccaa cccccagcag ggcagtggga cactcaggtg   23040
tgggaggtag ccgcacatca tgacccagct aggacagaca cacaatacag tagcctcggt   23100
gtgtgtgccg tacactctat catctccatc agtttgtgta ctgagggtga ccctgcctcc   23160
taattgcagg ctccctaagg gcacagtacc tcagccacct gttttctcaa aggctgagca   23220
cagggtgacc ccccacccca ccaaccccgc cactaatgtc tgggccataa gtgaacatgc   23280
ccctctcaga ggtaacagca agtttccagt gaggaaaacc agaacttggg acagcctggt   23340
tggggcgggc gggagtatga acagcctgtc ttctcatcat aaaattggca taatggagat   23400
tatctacctc atggggatag catgtcttgt ctgagcaaag ggagagtgga tagggattgt   23460
aaggatcaaa tgggatcatg agtgtaaagt acctgtagag gacctagcac atggtaagtg   23520
tataacactt gttgttagag taacagtttt ccctgagtat ccgtgggaga tttgttctag   23580
aatccccaga ggaaaccaga atctacattt gctcaagtcc cttacataaa atggtgtaat   23640
atttgcatgt aacctacaca catcctctca tatactttaa ataatctctg ggttacttat   23700
ataccctaat ataatgtacg tactatgtaa atagttgtat tgtttaggga ataatgacaa   23760
ggaataaagt ctatacgtat tttcagtata gatgcaatta tcaattttt ttcctctaat   23820 atttcaatcc atggttgttt gaatcaacag atgcgtaacc cagtgataca gggggctgac   23880
tgtattattc ctctgtagct tgagggagga cccagcagga tcagccattc ctcatcgacc   23940
ttcatggact aacaaaggct ccatttcaga aggtcttttt ttgtgagcca aggtctcact   24000
gtcacacagg atggagtgca atgcgcaatc atagctcact gcagcctcaa cctcctgggc   24060
tgaaaccatc ctcccacttc agcctgccaa ctaagtgaga ctacatgtgc acaccaccat   24120
gtccggttaa ttttaaaac tgttttgggg gatggcatct cactatgtta cccagactgg   24180
tctacaactc ctggtcaaa tgaacctccc gccttggtct cccaaagtgc tgggattaca   24240
ggcatgagcc accgtgcctg gacagtgtcc tttcaagctt ctcatgccct tacttcctcc   24300
tagacatgga tgtggctcaa gaatatcttt tacccaagag gaaactttaa ctcggtcaca   24360
gaacgccagg tttgggttgc agacgcttct tgtgggggag ggaggtcttt tccctgtat   24420 tcacagaaga ggaggttgcc aactggagat ggttcatttc caagtttgtc tggggtcccc   24480
cagctatgca ggacccagaa agcagatgtc tagacatcca ggccaatggt ctttcactac   24540
```

-continued

```
tctgtgagtc tcccgtgaac ttcacctgga acctggctgg gacacaggtc caaaatacgt    24600
aacttcagaa catacccaga attccttctg accagcctgg aaaagttcta gaaaatcaca    24660
cttcagccac gtgtacctac cctgtcaggt gccaaggcag gtacagcaca cagacaatcc    24720
cacatgaccc ttgcactgcc ccggggtgt taaaagagag ccttcccggt tcacagactt     24780
acacactgag gagcagagcc agaaattcat tcaatcctgc tcgcactttg aagatggtcc    24840
taacagcagg aacctaaggg gtcaggggc cccaaagctc cagaccctga tgtgtcctta     24900
ctgggcaggg caagaaatgg gtttttcccc ctgaggcagg atcagtggct ccagtctgcg    24960
gcagtcccac atggatcccc tactacccct acgcaccggt cctgcccag ggctagctcc     25020 ttggtgagaa actcaaagaa gtgggcgctg tggctgcggt tgtcctcggc ggtgcccact    25080
acgccgatgg aggagatgga cagctgcgcg cagggctcgg tggacccgct cagcgccatg    25140
gccaggcccg gccgtaccgt cacgttcacg cgctgagggg gacatgaaaa gttttgcccg    25200
aagttggagc cggccgggct acctctgggg acgggacccg agcgcgcgaa agccgaaacg    25260
cgcagtgttc gcggggcagg gatcccgata cgggccgcgg tccctgaagg tcacgcccgg    25320
gtcatgactg gggagggcga caagggaaag acgtgcggag ggggagccgc gggatcgtgg    25380
agcacggaaa gtcagagctt ggcgtgagga aaggagtggg gagtggtccc tggggaaaag    25440
attcggggtc actgtcgggg aggcggagca gggacagggc cggaccctg gcccaccaac     25500 ctcccctcgc cccgtgctgc ccggcccacg cttacgtccg caggtttgcc caggatggag    25560 gcagcggcg cgcagagtcg tttctccagc cccgcggca ctcggttggc gggcaaattc      25620
gtgtccagct ccaggaacgg catggcgggc agaggaacgg aaacagctct ggcggaagaa    25680
aagctggggg tacccaaggc tcgcggacca gggaggaggg gcgaggcgcc acagcaacct    25740
ggcttctcat tggctggaca gagactcggc gctccccgat tggctgccta gggtacctcc    25800
cgcttctgca aacaaaagtc acgtgtgccg gctgatttcc ggaagtccca tcgtctccgc    25860
cctacgtgta gccccaccca ctacaggtct ttaacccggt agtggaccca ccctgtctcc    25920
cccgacccct ctgcctggcg ccaggtgggt ttccctctca agcttccgcg ctgtggtcgc    25980
ccggttccta gcctattag aggtctgaac accacacccc cgacacacaa ggacacacac     26040
acacctatag gggtcttccc caggctcgac cctaataacc aatacaacgg gagcttaaag    26100 ttttttttgaa tgatttgcca ccatttcgaa gtcaggcaat ttcatgttca gtatggaaat    26160
ctgcgcttgg gcagtcagga gatgtggtta ctcgcggggg cgcgggtagg gctaggctca    26220
cgacaatacc tgtccctgcc tggtccccat tgacatctgc ctgtgtagcc tcttgtgccg    26280
gtggtgagcc actgtccacc aggggtggc aaaatatgtt cttaaaaaca tggaaaggcc     26340
gggcacggta gctcacgcct gtaatcccag cactttgcga ggtccaggcg gcggatcac     26400 ctgaggtcag gagtttgaga ccagcctggc caacatgacg aaaccccgtc tctactaaag    26460
atacaaaaat tagccgggcg tggtggcaga cgttgtaatc ccagctgctc gggaggctga    26520
ggcaggagaa tcgcttgaac cggggaggtg gaggttgcag tgagccgaga tcgcgccatt    26580
gcactccagc ctgggtgaca gagcgagact ccatctcgaa aaaacatcag aaaacatgga    26640
actctgttgg cgtggcttaa acatgagtgt ggtcagtgtg gcaaaatcac ttgaattgta    26700
cattacaaat atgactgaag ttgtggtcga gcaatgtggc tcacacctgt aatctcagca    26760
ctttgggagg ctaagaaggg aggattgctt gagcccagga gttaaagatc aggctaggca    26820
acatagcaag attctcttct ttattttcta caaaaaaaa aaaaaaaga aagaaatctg      26880 ggtgctgtgg tgtgtgcctg tagtcctagc tacctgggcg gctgaggcag gaggattgct    26940
```

```
tgagcgcagg agatctaggc tgcagggagc tatgactgtg ccactgcact ccaccctaga    27000
tgacagagtg agacccaggc tccccctcc cccacaaaaa agaaagaaaa aatttgcaag     27060
tttatatgta caatttcaac tacgtgtata aaattctcta taagtgtgca tacttaaagg    27120
agcctccact gaaaggccga cagagtctct gtctgtcatg atcttgtcct attagcagtt    27180
tgtttattag atgactcaga tatcagaagg tctgagacac acgacaggta aatatgacag    27240
tcctaagggg agagggcagg acaggtggc aagtctggga ccaggtgtgg ggcatggaca     27300
agccagtggt ccgggagtgg ggtgtagaga agactgtggt caaggttatg aggaggcatg    27360
ggagagggcc aggaaataac cagggacttc ccttcctgca aggaggttca tgaaccagcc    27420
ctgcacccca cttgtggaac acaacatcgc cccacagtga ggagagagac cgaggagacc    27480
aaggctgatc ctgattcaga catctttcca ccaggtcacc cctcatcgat gatacatgct    27540
cagtccgggg gtatccccg caaggaaaca ctggggctga ggagcccaga gaggtcgcct     27600
gacctggact ggggctgggg aggtcaggga agtctccctg gagaagagac agggtgccaa    27660
atgccaaaag accaggaagg gcaccaggcg aagatgagga gggaacagca tgagcggagg    27720
ccaagaggcc aaggtgggag cccagagagg ggttaggagt gtgcaggcag aagggccac     27780 ctggaggagt gggagcaagg ccttgaatgc aaagttcaat gacttgtact ttagcttctg    27840
ggcagtgagg aaccatacaa agttccacac agaaggtcag ggtcaagtaa gcgtttgccc    27900
aagctctttt cagaggtcac atggaagcta aatggaatg gggtaggaga caaaaggaat     27960
gcaggcatga tatctggagg aactgtggac cagagccttt gcagatatgt cttctcttca    28020
accaaggaga cggacagctc catgtctta ttctaccaac acagcatccc ctcagtggct     28080
cagcaagtgt gggacacgca ctcacagcaa gaaaagctgc attaaggtct tcagattctc    28140
tttaacagca ggttctactg gaggcaggtc cttggccttc aggacagctg ggagggcctc    28200
ctggaagagg tcctcccgca ctgcagcctc cacgtgttgg gcaccatgct gccaccgtgg    28260
gtccgctttc aaagactcag cagccagcac tgatgggcta ggggaagaca gagtcagcgg    28320
aggggctggg catagccaag tgtaaggcag catgacctgc tttaggggtt ctctgattgg    28380
attttccctc ctccaccatg tgtgtgatgg gctaggatgt ccccctccct ggggacactt    28440
ggaagcctct taatatagct gcggtgaggg gtttgtaaag ccccatttta tagatgagga    28500
cactgaggct cagaaggaga agtgactcac acagggtccc acagccagaa aagacaacat    28560
gagctgggat gtcagctccc ttcccggata caccactgcc cagcgggcca ccgcaccccca   28620 tggcactctc atgcctcagc tccgtgattg ccaccaagcc agccacagag atacggggcc    28680
cagtaaggaa ggcctggtcc cgcaggaact tgtcctcgag cagctgcagg catccgtcca    28740
gctcagccaa agtggccgcc aacatctcgg gtggcactga ctcgcccagg aacacaggga    28800
ttattatctg gtgggccgac aggcagagag aggggtcagg gtctgcccaa agcccatcct    28860
ggttcccacc atcatcctat catcaccagt ccttgggatt tctgctcacc tctgctcact    28920
tctttccact catagccacc agtagctctc atctcctact caaacaggga cagcctcccc    28980
cttctccctg ggtcctcaca caaggcaacc agtgggatcc ttctgtaatc tcaatctgcc    29040
cgtaccctct cttgcataaa gccttccatg gctcccact gccctcatga gaaaggcctc     29100
aacacaaagc cagccttctc cagtgcggta gccatcccct ccccactttt cacctcacct    29160
cctactaccc cccacttatc aaacgggaat gtgtgtatga atcctccctg gaatctggtt    29220
acagtttatg ctcccaatca gtaaggtcag agtgggggcct gagcctctgc atttccaaca   29280
```

-continued

```
agctccctgg tgatgctgat actcccagtc cattgaccac actttggata ggaagagtct     29340
acacttgctc tactcaactt ctctccattc tgtcctcaaa cacaccacgc ttccttcccc     29400
accagctgga gggggctctg ctcccaggcc ccagaggtca aggcagacac agttaaggtg     29460 tggaacctc cttattgccc gatggatcct ccagagaggc ggtcccttac tttcagcagg      29520
gcgcgtgtct acctgtttca tgctgtctca cacacagggt gccacccctg tgctgggcac    29580
tgggtaagtg ctctgtacat attaattagg agtactcatt tcaaaaatat gtgtgccttt    29640
gataaataaa aacagtatgt gcatgttgtg ttggtgtgtg cttccttgat tattactgaa    29700
gttaaacatg ttttcatcca tgtattgacc atttctcttt gtccttcaat gaaacctctg    29760
ctgatttcct tcgctcattt ttttcctgtg tcttcgtctg atgagtttct cttcttttg     29820 tttgttcgtt tgtttgtttt gagacagtct cgctcagtgg cccggctgga gtgcagtggt    29880
atgatctcag ctcactgaaa cctctgcctc caaggttcaa gtgattctcc tgtctcagcc    29940
tcccgagtgt gccaccgcac ccagctaatt tttgtatttt tagtagagac ggggcttcac    30000
cgtgttgccc aggctggtct caactcctg acctcaactg atccgcccat ctctgcctcc     30060
caaagtacag ggattacagg cgtgaaccac cacacccac ctgtctgatg ggtttctaag     30120
aacatcttaa aggacattac ttccttctga cgtatctttt accgagatcc ttcccagttt    30180
tttgcttaag gttaatccat tttttcctcc acaaagtaac cttgtatatg tattggtttt    30240
ttctttgttg agttctccca ctgttctgag gcttagaaag tcctttcata cccagacatc    30300
agagaaacag atcccgtgag agtaactggg attgcaggtg tgggccagca tgccctgtta    30360
tcactccctt tctctgagtc agcttttctc tctcagtctc gtctactcct cgaactcagg    30420
aaatgtcact acaggtggcc ccagctcccg tttacctccc catagggagc tcctctctcc    30480
agttccagtt tcaaaactcc caaggaagca ttctggttca ctcgcttggg ccactggcca    30540
gagggatggg atactctgaa agattcagct agagtcccgg gcccagccct ggaccatcac    30600 tgtgcccct ggtgagatgc cagggctggg attcagggag aagaaaggag gttcccggac     30660
agtcattcct gcctcccgcg gctgcgggct ccctgccccc atcctgtgca cgaagtggga    30720
gctcccgctg tctggcagct cccgctgtct ggcagcagct gctctgcagg ggacagtctg    30780
gacggcagaa agttcatcct taaccccagc cttccagtca aggttcccac cagtttggga    30840
cacctgcaag tgtcacatcc cactgggtga aactctaaga tcccttttag gggatcccat    30900
tcgctccctc ccttccgcca ccatgcagcg ccgagaaaca gagctctgaa cgaaccctca    30960
gatgtccgtg cgctggggcc tttccaggac ggcggcgccc agtcgtttct gggtcagggc    31020
gacgcctgga actgggcagg gtccctggca ccgggatccc gaaaagcaga cctgcttctc    31080
cctgtccagc cggttcccct tccccttgca gtcggccccc tgcatccgcg tcctccctgc    31140
cagtcgaggg tccccagctc caactccacc ctcccagctg tgcgttcata gcgaccgccc    31200
tccctgtagg gacgcacgga tctggtggtg gagtcttggc cggcaggact ggacaggaac    31260 cgaagggggcg aggcgggtcc ggggtggtg cgctccaatt gggtgctgtc cccaggggt     31320 ggggcctgat cccctatttc ccggcgcgcc gggatcctgc cacagctgct gcccacaccg    31380
cgctcagcgc cttcactgcc atcccgctc tccttgccgc cccgccatg ggcctagagc      31440 tgtttcttga cctggtgtcc cagcccagcc gcgccgtcta catcttcgcc aagaagaatg    31500
gcatcccctt agagctgcgc accgtggatt tggtcaaagg tgggcccagc ccgtttcccc    31560
gcgtgtccac aaacccagtg cacccccagg ccccgccct gctctgccct gagcgtctcg     31620
ccgcccgcac agccccctca cctcctcctg cagcgtctgc caccagagaa tgctgtggac    31680
```

-continued

```
tgagtggcct tgaagggatc acagcctctc tgaaccttag cttgccttct gaaaaggagg    31740
ataacgttac cttctgctct gtagggatgg aaagaaaata ctgaatggag ttgacagagt    31800
tcttgcgtgg aatgcacgca tataaattca caaagcccag aagacctcgg gaagaaggac    31860
atactgttgt gagaattaag agatgggaag agatgagcca ccccagtttg cctcccctcc    31920
cctggcccac cagagtccgg ctagaaaact tctctttatc cacctgctgc acctggcccc    31980
acccaccaaa accccccagc tgccccggaa tgtggcaggg cagggaggcc cagccaggga    32040
gtgaggctga tccaggcctc tagtcccaga ccttgctgtt tctcagggct gtgggctcc     32100 gcttggggag gaggagggag ggtgtagagg tgcagcgttt ttactctgaa gacctttctt    32160
gacttcttcc tcttcagggc agcacaagag caaggagttc ttgcagatca acagcctggg    32220
gaaactgccg acgctcaagg atggtgattt catcttgacc gaaaggtgcc ctccttccct    32280 caccctcac cgcatccgga gcccatgtga ccttggctct ccccactggc cccggcccc      32340 agtggccctc ccataccccca tggggcagcg agggagggga aaggcgaggg atctggccgg   32400
gcgcggtggc tcacgcctgt catcccggca cttcggagg ccaaggcggg cggatcacga     32460
ggtcaggaga ccgagaccat cctggctaac accgtgaaac accgtctcta ctaaaaatgg    32520
aaaaaaaagt taaccgggcg tggtggcggg cgcctgtagt cccagctact ctggaggctg    32580
aggcaggaga atggtgtgaa cccaggaggc ggagcttgca gtgtgctgag atcgcgccac    32640
tgcactccag cctgggcgac agagctagac tccgtctcaa aaaggccggg cgcggtggct    32700
cacgcctgta atcccagcac tttgggaggc cgaggtgggc ggatcacgag gtcaggagat    32760
cgagaccatc ctggctaaca cggtgaaacc ctgtctctac taaaaataca aaacattagc    32820
agggcgtggt ggcggccgcc tgtagtccca gctactgggg aggctgaggc aggagaatgg    32880
cgtgaactca ggaggcggag cttgcaatga gcagaggtcg cgccactgca ctccagcctg    32940
ggtgacagag ggagcccact ccagcctggg cgacagaggg agactccgtc tcaaaaaaaa    33000
aggaaagaaa gaaaggagag gtatctgggg agaaggtaca gcttgggtg tgtccgggat    33060 gagcaggggc tgacagaaca tgtccccca cctctcatct tcagccttt tctgagccgca    33120 gggcctctcc actcccagac tgaagggtat tagaagagaa gacaagggaa cattttccaa   33180
ctgttgcgca tttgttcaac aaatgctagc tgaaagagc ctctagtgac ttgtcgcaga     33240
ctacccaatc tacccaggcc gggcctagag gccaatgcca tggcccaagg gcacagctca    33300
tggtgaggtc cagctgctgg gcaggaaaag gacaagaggt caggtggctg cagaggtgat    33360
ggctgggggc ctgtcagacg ggggccaaag acattcctcc cctcgtgatc cctgacccaa    33420
gcgcgtggac atgcaaggga ctccacggag catccactgt gtgccagccc catgcaggggt   33480 tccaggggtc cagggagcct attctgagct gcaccgcctc ggacaagtca cttgaccatt    33540
ctgaccttga gttttctctt gtgctaaaag gctaacagga gtgtctacct cacagggcgg    33600
ctgctggcat atcacagaga tgaggttctc aaaatgcaaa gcagaaggtc cagccaagag    33660
tcggtgccca aggcaacaaa gacaggagga gactcgtagg aggaggggt ggtgttgggg     33720 agctggagat ggagggcgag gctggagggc agtccttcaa atgcagagaa gccccggggc    33780
cccactggca gatgggagca gttaggggta aatgcctggt gccagtgtcc ttatagccac    33840
tgcccatttg ttcccagctc ggccatcctg atttacctga gctgtaagta ccagacgccg    33900
gaccactggt atccatctga cctgcaggct cgtgcccgtg ttcatgagta cctgggctgg    33960
catgccgact gcatccgtgg cacctttggt ataccctgt gggtccaggt gaggagagcc     34020
```

```
atctggagag tgattggcca tcagggagta gttggcagta ggccggggcc atagactgac   34080
ccactctctg cccccatcag gtgttggggc cactcattgg ggtccaggtg cccaaggaga   34140
aggtggaacg caacaggact gccatggacc aggccctgca atggctggag acaagttcc    34200 tgggggacag gcccttcctc gctggccagc aggtgacact ggctgatctc atggccctgg   34260
aggagctgat gcaggtgtga gctcagcctg tgggcagtgt ccctcttcgt gtcacaccca   34320
tgaggcagac agaaacactg aggactggag aaagccagaa cttgcccag aatcatagag    34380 caagtctctg gatgatctgg ggccagaacc ctgaacttct gcctcctgcc tgggtgtggg   34440
gtctcaccct ggctgctctt gggctctaag gctgaacata ctgcctgggc cctgtggtc    34500 cattcactta ggggctgggg aatggaccat gtctctgata cttctgccca tggttccagc   34560
attcgggtcg gcagtgacaa ctgggaaagt tgtatgccca caacttttc atccttgtcc    34620 ctacagccgg tggctctcgg ctatgaactg tttgagggac ggccacgact ggcagcatgg   34680
cgtggacgag tggaggcttt cctgggtgct gagctatgcc aggaggccca cagcatcatc   34740
ttgagcatcc tggaacaggc ggccaagaaa accctcccaa caccctcacc agaggcctat   34800
caggctatgc tgcttcgaat cgccaggatc ccctgaaggg tctgggatgg gggccaggag   34860
attagcaaca aggattcatt ctgttactta cttgcccctt tttatctttc cctcttgccc   34920
cagtcccttc tctccagctt catgtgaagc tctgcacaga caagacactc agtgtccttg   34980
gcagtgctgc tactcctcag gtgcagcata cataaccagt aagagactaa atctgcaata   35040
tataaagagc tcctacaaat cagtaacatg aagaacactc aaaaattggc aaatgtcatc   35100
agtgttttaa acagaataaa gattccaaac actttgaata gagaaccaag agttattggt   35160
tttactacat tgttgtgtta tacatatgga gtaaaagtat gtgctagtaa tcctcatcat   35220
ggttaataac aaagtaaccct cacaataacg agtcaacata attgtatcac cagggcaaca    35280
aaatgttaag taagtaacca attcgaattg caaactgtta aaggatatag gcgatgtttc   35340
acagggcata gcaacggtct ttgaagtcta ggaaacttaa aagatttctt ttaacaagca   35400
ttcatgtctt ctaggacagt tttgtaataa ctgcaaatag taagattata cattgtcaca   35460
cagacctcca tgtatatcca tgggatggac cccaccacaa tgattttaac ggagagaact   35520
tgatataaag aattggtaac caggcattag agaactccga agacagagag aatccagatt   35580
aacacggagg taaacactgc aagaagctac caccccctagg gctgggggat caagggagga   35640
attaggaaga ccaagatgct ggaggggccc tgaagaattc aaacctccaa gaaaggtgtt   35700
gctcatcccc cctagcatca ccttccaaga agggcaggtt tccccagttt gccctgaggt   35760
cttcacagga ggccatgtgg ctgtggatgc agttctcaaa tgtgacagta gatgtcactg   35820
ctgaccaata aacaggatgt tccagacaca ctctgcgcta cctgcccaca tgtcttgtgg   35880 cttttggggcc tatttcccat gcctgacctg tgcccaccat gtgccactct attggggac   35940 ctgccccaat aatcacgtag attgtttcct atttttccta agtgtcggcc ggcttgagaa   36000
ataaagggac agagtacaaa agagagaaat tgtaaagctg tgcatccggg ggagacgtca   36060
cacgttagta ggatctgtga tgccccacaa gccacaaaaa ccagcaagtt tttattaggg   36120 atttttcaaaa ggggagggag tgtgcaaata ggtgtgagtg acagacatca agtacttaac   36180
agggtaatag aatatcacaa ggcaagtgga ggcagggcga gatcacagga tcacaggacc   36240
gaggcaaaat taaaattgct aatgaagttt cgggcaccat tgtcattgat aacatcttat   36300
caggagacag ggttttgaga ccaaccggtc tcaccaaaat ttattaggcg ggaatttcct   36360
cttcctaata agcctgggag cactatggga gactggagtc tatctcacct ctgcagtctc   36420
```

```
gaccataaga gagaggccac gcccgggggg ctgtttataa gccgatacct ccaggtgcgt    36480
attctctttc tcagggacat tccatgctga gaaaaagaat tcagcgtat ttctcccatt    36540 tgcttttgaa agaagagaaa tatggctgtg ttctgcccgg ctcaccggtg gtcagagttt    36600
aaggttatct ctcttattcc ctgaacaatt gctgttatcc tcttcttttt tcaaggtgct    36660
cagatttcat attgctcaaa cacacatcct gtacaatttg tgcagttaat gcaattatta    36720
aagggtcctg aggcgacata catcttcctc agctgacagg attaagagat taaagacagg    36780
tataggaaat cataagggtg ttgattgggg aagtgataag tgtccatgaa atctttacaa    36840
tttatgttta gagattgcag taaagacagg cataagaaac tataatagta ttaatttggg    36900
gaactaataa atgtccataa aatcttcaca ctccacgttc ttctgtcatg gcttcagccg    36960
gtccctctgt ttggggtcac tgacttcctg taacaccact cctagccgga agtattccaa    37020
gtaaccattg caactgtcct gccttaaggg tgcctggtga tggcttctgt cttaggtccc    37080
attctggctc tctcttccag tgatttctca tactttgggg gacactctgg cctgctttcc    37140
tgggcctttt ccattaccac cccctctccc catcaggcac tggggatggc ggccacagcc    37200
tatgccttct tgatccatgc tggctgcctt gggattgttc cttattggat ggttttgctt    37260
tcaacagaca ctccaataaa gtacacgaaa taaagaataa agttaaacag tcagtccccg    37320
tgctgtgtag gtggcagtaa gtctgggaga gcgacctcag ctgaactaac catgctgtgc    37380
atcattgtca agcgggacca gcaggatcct taggtcacct ggcaggagga ggggcaggga    37440
agggtcccta gaagtgatct tgagttgcac ttagtgctct tggcagaggg aagggcttgg    37500
gctagtgctg gaggcatgaa gatggggtgt gttcagggct ctccagcagt ccaggcatgg    37560
gaaggggacg ctgagggcca aaggctaagg tgacactggg aagggaacca tagcaaggtg    37620
aggaatggct ttcggccatg tgactgaatt gcctgtgtgt ggtgcgtgtg tacgtgtgtg    37680
aatgtcagtg aactgtgtgt gtgaacgtga gtgaattgtg taactttgtt tatgtgtggg    37740
tgtatatgtg tgtgatgtga gtgaactgtg tgtatgtggg tgtatatgtg tgtgatgtga    37800
gtgaactgtg tgtatgtggg tgtatatgtg tgtggtgtga gtgaactgtg tgtaagtagg    37860
tgtatatgtg tgtgaatttg aatggtgtgt aaatgtgact gagcagtgtg aatttgtgta    37920
tgtgggtgta tgtgtgtgag tgaactgtgt gattttgttg gtgtgaattg tgtgcctgtg    37980
tgtgtgaggt gtgtgtgtgt gtgtgactga actgtgtgat gactttgtat taatgtcagt    38040
gaatggtgtg gttgtgtatg tgggtgtata tgtgtgtgta tgtatgtgaa ttgtgtgtgg    38100
ggttggtgtg tatgtgtgtc aatgtgagtg agttgtgtga ctgttgaata tgagtgaatt    38160
atgtgattgt gtgggtgtat atgtgtgtac aggagttaac tgtgtgactg tgtgtaaatg    38220
ttatgattgt gtgtgtgggt gtatatgtgt gaatgtgata catcgtgtga ctgtgggtgg    38280
acgtgggtgg atgtgtgtgt gagtgtgcgt ggctgtgtgt cgaacagtgt gtgagtgtaa    38340
gtgtgcaggt ggtagctgtg gaattaaggc acattagggg aatccttcct tggctctggt    38400
ccttggtttc cctcctatga acaagttggg gtgaattagg cagtctctgg cattccagga    38460
tttggtctca ggtctaaaca ggatttgtgta aagtgaaagc agcatcccctt gggcatcccg    38520 ggaggtgtcc ctgccctcca tggctcacct tctgccacat ggcccagcag cagctactct    38580
gcagggccat gtgctgccat gacaggtact gatccccatg ggcgcgggcc tgcaggtcct    38640
ggaggtacca gtggtcaggt gctttgtaca tgcagctcat atagagcaag ctagccacac    38700 tgggggggaca tggcaggggc agaagacatg ccctgaacac tcttcagcca ttttctgggg    38760
```

-continued

```
cattttcact atccccatga tgcagaggag ggatgtgagg ctcagagagg ttaggtaact    38820
gcccagggtc acacagccct acacggggcc agattatcat ctcaactaat ggcagcaagg    38880
aagaaacaaa atgtcatgaa cttcagcagg ggctcaggga aggcttccag gaggaagggg    38940
cacccagtgt gagtctgaag aatgagagca agttgggtat ctccccaaca tatccaaagc    39000
atggacaggg ccaggagcaa ggccagcagg gagagagcct tccaggtgac atggcagcat    39060
tgctccccac cccgtcccat ctcctgttca cctatggtga agggttgtgc agtctgaccc    39120
ccagagctca tcatgcctct atgggtgttg gaccatccag tgatcccagg ctctgaatgt    39180
gaatccagct ccaccaagga ggcactatgt ggcctcggta aggacgccac ccatgcggcc    39240
accaacctgg aggctggttt tggctttcat ttttcccacc cacctccaac ccttcagcac    39300
accctgcagt tagagtttca agaaaagtca gaaccgacca tcaccccacc aaccctgcac    39360
caccaccacc ttggtctggg gctccagcgc tgcatgccag atgactgcag tggctttctc    39420 accccctgcca gggggatcct ttatgacgta agtcagatca cagttctcct ctgctcaaaa    39480
tactccagcg actcaatccc cctgcggtaa gagccaaagc cttcccagtg tcccatgctc    39540
ccctctgtcg tgacctcctg ctcttcctgc tcactacacc cacccctggcc cgttgctctc    39600 cagtctgaac cccatgcatt gtcccacctg gagccttcgc cctcactctt ccctccagcc    39660
agaacaccct tcttcctcatg ccttgcacat tcctacagct ctctgctcag atgccacttc    39720
ctccagggag tcttccctca acatcctact cacacacccc caatcttacc ctgtttattt    39780
tttccatggc atccatcaac atccgatatg ttccatgttt acatgggtta ctgtcagctc    39840 cccttctat taatggaatg tgagatccat gaggagaagg acgtagacac gttcactgct    39900 caagcccag ggcttaaatg gggtctggcc ctggtggatg tttagcaaat agccactgaa    39960
gctcgctgag tggtccctcg actctccagg gaaacagcac ttgccccaca ggatttgtgg    40020
gcaaaatggt agcactaaga tgcctggtac agccgctcct cgaaacttag cactctcctt    40080
ttttcggagg ggaaggctgg cggtgaggag gcccggaagc agactgggcc ctgtggcctt    40140
gtgcaagtcc ctcccctcct ccagcctcag tttcctcact tgtacaatgc aggagggggac    40200 ttctataacc cttgtcaaca ctgggcacca ctgcctgcct ccacccattc ttcaccctgg    40260
ggctggtgca gggcccacag tccatgatcc aagccatcaa cagtgaacag acagccgact    40320
ggccccacaa ggcccggcag cagcccacgg accggttacc tctcagccaa ggtgaagtcc    40380
ccatccttca aggcccggca ccttcctcag ggggttcacc tgggcaaagg catcgctgtg    40440
ctgctggcct gcaggagaga tcagagaggt gagtggggat aacccagagt tctctgaggt    40500
ctctgcccac ccccacccca aaatcccagc agcagctttc tgaggcccct atctgggagg    40560
catcagggaa gaggaagcct ctctgctagt cactgggtca cagaccttga ccccatcaga    40620
gggccatctt tcctgtgtcc agctccttga agcatggctc aaggacaatt ccctggagct    40680
gtaattcaca ccccaccccc agccagttcc atccataggt cagacccctc cagcctcctc    40740
cctgggctct aggcttgccc cctctgattc agcttcctat cccagctggg gacttaggcc    40800
ctactggcca ggctgggtga cctgtcaata ccccagagtc ccagccaaac atgttcccaa    40860
ccctcagacc aacctcattc ttgctgggaa tcctgccccc attcagccac tcagcccccg    40920
gtggctcagc tcttcttcct ttcttatgcc aaactctcaa ggctccctcc ccactggggg    40980
ttcccaggtc tgactcactt tagcattcta ggccagtgct agaggccgca ttaggtgcct    41040
ggtgtttgga tcagaggacc tcagtcaagc caggctccag tctgatcata ggcctacatg    41100
tgggcctctt tgcccttcta ctgaatggac atgcacaccc ctgcccattc tccctccaca    41160
```

-continued

```
gactgcttct gtgtccagcc cctgttctgt agcaggtgac tcaagctggt tgtaccaagg    41220
gcagcagttg ggaagagtca gctgagcagg gtcctccctc tggcctgccc aggggctct    41280 ggctctgctc tctgccctac tgcttagtta tagccctgcc tcctccactg aattgtgctc    41340
cagctgcatc tctgtatgcc agccagacca gcaaacgctg gagctcaggg tgagggtgct    41400 ggcctcccccc actgccctgc cacagggccc tccagcctct agcctctagg agtagcccct    41460
tcagctgggt gagaagcccc atgggataga gcaagtcaga tgcaggaaaa agaaaagaca    41520
gaagaatgcc aagaaataca taaaagtgga agagacccag ggccagacat ggtggtgcat    41580
gtctgtgatc tcaacacttt agaaggagga ggcaggagga tcacttgagc tcaggagctc    41640
aaggtcagcc tggtctacat ggcaaaatca cgcgtctaca cacaccaaaa aaaaaaaaaa    41700
aaaaagtagc tgggcacggg gacgtgcctg tagtcccaac tattctactt aggaggagta    41760
agttgggagg atcacttgat cctgagaggt caaggctgca gtgagccggg atcatgccac    41820
tgccctctag cctgggctgc agattgagac actgtaataa ataaataaat aaataaataa    41880
ataaataaat aaacaaacaa taaaaaagtg aagagacac aggcagggt agacagggac    41940 tattttactt aggaaacaac gaggcagttt gttttttcca agcacatggg gtgaagatat    42000
tcttgcccca ctccatttcc ctaccctcgt tctgtgcctg ctgtgccctc tctaaacctg    42060
tattttgaag aatgttttgt attcacaagc aaagatcaag cctctattaa aatagacaac    42120
cagtggggca tggcggctca tgcctgtaat cccaacactt tgggaggcca aggcaagagg    42180
atcacttgag cccaggagtt ctaggccagc ctcggaaaca cagcaagacc tcctctcaat    42240
aataataata ataataataa attggccagg catgtcggtg gcacctgta gtcccagcta    42300 cttgaggggc tgaggcggga ggatcgctta agcctggaag gtcgaggctg cagtgagcca    42360
tgattgtgcc actgcactcc agcctgagtg acagagttag atgctgtctc caaaaagtaa    42420
aaataataac atagataatt atgtaatagt ttccacaccg gagagtctga ttcttcgtgt    42480
tagtctgcat tcttggcccg actgcaaagc agcggggaca ggcagggatt cgtggccaat    42540
atcccctggg cctgcctgcc cagcccagct ttggtcagct ccactgtgcg aagctcgaag    42600
gggatgccat tcttggcgaa gatgtagact gaacggcagg gctgggacag cagacccatg    42660 gcggggcaa tggggtgggg cgtcggaggg cagacctaaa cccaggggac gggccctggg    42720
gacaaacccg gggacaggcc cgggaacagg aactgcgggc aggaatggct ggttgggggc    42780
ggcggacagg aacggctggg ggtaggtgag ggatgggcag gaactgctgg gtcaccgagc    42840
ctgcagcggt gcacctcacc aggagccccg agtccggcca cgccctcttc actcatccct    42900
tggctcctag aactttgggt caatcagtgg cgtgtctgct ctctcaccac ccctttctgg    42960
gaatctaggc tgcaggtata tttcccacta aagggaaga ggagaggctg ggcgcggtgg    43020
ctcacgcctg taatcccagc actttgggag accgaggggg gtggatcacg aggtcaggag    43080
atcgagacca tactggctaa acggtgaaa cccgtctcta ctaaaaatac aaaaaattag    43140
ccgggcgggt tggcgggcgc ctgtagtccc agctacttgg gaggctgggg caggagaatg    43200
gcgtgaaccc gggaggcgga gcttgcagtg agccgagctc acgccactgc actccagcct    43260
gggcgacaga gccatactcc gtctcaaaaa aaaaaaaaa aaaaggaag aggagaaagg    43320 aggtgcagca gcctccttgc ccagtgcctg ggcccagtgc ccaggacgga ggccagagag    43380 gaaggtggc tgactgcctg cggggctgcc agccccacac ctcatgaagg aatgagctgt    43440 ccctcccccag ttgctggggt catatttgtt acactctagc taacgcctcc ccgagatggc    43500
```

```
tgaggccctg tgaggcctat ccagaggttt ccaacagtgc ctggcattgc acagtaaatt    43560
aatcaccatg acacgagttt tgcaaaagag aaaagattta ttcacagggc accaagcaag    43620
gatgtgggat agtagctctc aaatccacct tcccgaaaat aaggcttagg gataagcctt    43680
gcttccaagc agtagagcac aggccccagc cacgctccag ggtaggggac catacaagga    43740
tgtgaatagc agtgtcggcc ttgtgggcct acaacgcaga agggccatgc acttggttta    43800
aagctttgct gttgccatct taacattctt aacaagttaa aataagggt ccccacattt     43860 tcatttatag ccagtcctgt ccaaggagtt caaagatctc atgagggtgg acagggcact    43920
gtctgctctg ggcagtgatg ggaccactaa cagttgttct ccagtctccc agcgcctacc    43980
ccagggacac accttcccct ggtctctact attcttttt tttttcgaga cagggtcttg      44040
ctgttgccca ggctggaatg agtgcagtgg tacaaactta gcttactgca gcctcgacct    44100
gggctcaaac aatccttctg cctcaccctc ccatgtagct cagaccacat gcgcatgcca    44160
ccaatctggg ctaattttt gactttgtag agacgggtc gcactttgtt tcccagggtg       44220
ctcttgaatt ccttggctca agtgatcctc ccacctcagc ctcccaaagt gctgggatta    44280
taggtgtgat ccaccacccc tggcctctct cacattcttg acatttaaag ttaccatcat    44340
tgacaaggaa catgggtaca ctccaattta ctcaagaaaa agctcttttc tccattgaag    44400
acatatgtgg cctagctgct tcatattcta gttgaggtct tcttgttgtt tccttttct     44460 tcttctctct tgttttttag agacgaggtc ctgctgcgtt gcccaggctg gtctcaaagt    44520
tctagcctca agagaccctc ctgccttgtc ctcccaaagt gttgggatta caggtgtgag    44580
ccactctgtc cagcctcaaa ctgtggtcat tagatcagca gcagtagcag ccttgcctgg    44640
gagcttgtta gaaatatact aacaggctcc cacccccaaa cccagaccta ctgaatcaga    44700
cagagtttat tttcataaga tcctcaggtg atccaaatgc accttaaact ttgaggagct    44760
ttgattcaga acctgggctg gaggcccta ggggccacct tgttcctcac agactgcaag      44820
gtatgttttt tcttgcctc ttctctctgt cccaatgtct ccttctctct gtgtctgacc      44880
ctgaggaccc tgtgacatcc tcccagggga gtttccactg ccaaaggcct gattctctag    44940
aaactgatgg gctcctctag acaccaatct ctacctgggc tcttgttgaa gaagccaatc    45000
agctcattgg ttggcgatca cgtgatatac aacatggctg ccttccaagc cttatgtgtg    45060
gacaaggaga tagggacaag taggcatatc atgttctgct acctggtcca tcgtctctcc    45120
tcaggccccc aggatacacg tttatgggga gttttcctcc cttcccccaa tatggtcact    45180
cataacttta cacccaacag tcaaacaggg gtggaagcta cagggtttca tgtaaacaat    45240
aggctaggct gtggggctga gtaaaaggca ctggactgtg gtaggtctta ctccaagatg    45300
gccaaatgga agggcttta gctttctttg tttttgtttt atattttgag atataatgtt      45360
caaatttaca cttcagaata aaaagagcc acaatttatg cttcatattt tttgtagctt      45420
cttccctatg cttttgaaca atgtaatcat attttcatta tcagatataa ttcccatacc    45480
ataatatcca ccctttcaaa gtatacttta aaattcaatt ggtttaaagc caattcagtg    45540 gttttagta tattaacaaa gttttgtcac catcacagtt atctaattct agatcatttt       45600
catcacccaa aaagaaactc tgtacccaat aaagagtcac tccccattcc cctcttcccc    45660
tagcccctgg ttaccattca tctactttct acctctgtgg ataggaagta gctgcctatt    45720
ctggagattt cattcaaatg taataatgaa atatgtggcc ttttatgact ggcttctttc    45780
atttagcata atggtgtcaa ggttcatcca tgttgtagca tataacggta cttcatccct    45840
tcttatggct gaataatatt caatttatg gactttttag caaaacattc taattttac        45900
```

```
ttctctactg tgcttattgt ttgtctttct ccacaacaat gtgagcacta aaggcagaca   45960
tttttgccta ttttgttcac tactgctttt tctgcaccaa acgcattgcc tggttgtggg   46020
tacttttcta gttttaggaa ggagaagaca agatataggt cctgactctg gttctgcctc   46080
tcattcatat gctacccttc cccttgaaga acttgtttct tcatctacaa aatgggcata   46140
atactactac tcatcagggt ggttgtgagg attaaacaag gtaagagatg taaaattgca   46200
tgttagttat cagatagatt tgtgttccca tctagctcca atgagggaga ggatttgctc   46260
tagtctgtcc ctctgggctc tgggcttcta atgggcagac agcttcctcc atgatgtttg   46320
tagctgttaa ggctggcgta gtccctcaag acaagttttt tttttgtttg tttgtttttt   46380
ttttgagtca gagtatcgct ctgtcaccag gctggagtac agtggtgcga tcttggctca   46440
ctgcaatctc tgcttcccgg attcaagcga ttctcctgcc tcagcctcct gagtagctgg   46500
gattacaggc atacgccacc acacccagct aattttaaga caagcttttg gaattgaact   46560
gctgatggtc ttccatgaac aattcaacag aaacccagta gcgtacactt ccttgtatgc   46620
acttgcaccc tctctttaca tttattacac atttaatgct acctaataat tccctatact   46680
tttactttat ccaatcgttc aacagattcc aaccgaaata catagaagag tgatattcca   46740
acttcatcag accctgagat tctatttta acatttcttc catggattgt tgaatgtttc   46800
caatgattga tccaccttcc cttggccttt tctacattac agatttggtg gcatgtccat   46860
gtctatgttg ccaaacttgc ctcatagacc cagcttgaac acaagatggg tgcttgctga   46920
agagcaggac tcattctgtt gaacctgcat gttttctcag gtcagattgc ttggtggcgc   46980
ttctttaatt tctttcaaca gcacattgta gtttgctgtg ttgaaatgtt gcttttcttt   47040
ggttaaattt attctatttt attcttttg atggtattat aaatggaagt gtggttttaa   47100
ttttgttttt catcctttat tgcaaatgta tactattgat ttttgtgtat taatcttgta   47160
ccctgcaacc ttgctgaact tattttattt tattgagatg gagtctcagt cagtcaccca   47220
ggctggagtg cagtggcttg atcttggcac actgcaacct ccacctcctg ggctctggtg   47280
attctcctgc ctttgcctcc tgagtagctg ggactacagg catgcgccac cacgcccggc   47340
taatttttgt atttttagta gagacggggt ttcaccatat tggacaggct ggtctcaaac   47400
ttctgacctc atgatctgcc cgccttggcc tcccaaagtg ctgggattac aggtgtgagc   47460
caccgtgccc agccttgaac ttgtttatta gctctaatgg ttttttaagtg agttaagaat   47520 ttctgtaatg tcatctgtga atagagatgg ttttacttct ttctttctga tctagattcc   47580
accttgttcc ttttttcttgc ctaattgccc taataagtag aagtagtgtg aatgaacatt   47640
cttgtcctgt tcctgatctt aggggggaaa cgcttgatct ttcacaatgg atgaagtatg   47700
gtgttagtta taggtttttc atagatgctt tttgtcaagt tgaggaagtt cctttctcgt   47760
cttcatctgc tgagtaattt tatcgtaaaa ggatgttagg ttttgtcaaa tgccttctgt   47820
gcattaggat gatcatgtga ctttctatta acatggtatg ctacactgat tgattttgt    47880 atgttgaact gcatttgtac tcctgggata aatcctacct ggtcaaggtg tatgatcctt   47940
ttaatatgct gctggatttg atttgctaat attttgctga ggattttttac atctatattt   48000 ataaggatat tgctttgtaa ctttattttc ttgtaatgtc tttttctgtc tttggtatca   48060
gagtaattct ggcctcatag tatgagttga aaaatatttc ttcctgtttt attttttggg   48120
aagagtttgt gaaggctttg tgttagttct tcaagctttt ggttgaattc accagggaag   48180
ccatctggtc ctgggctttt ctttgtggaa tttttaaaaa taattaatat tttaatctct   48240
```

```
ttatttgtta caggcctatt aaaattttat ctttcttctt aagtcagttt tggtagattg   48300
tgtgtttcta aaattttccc atttcatcta ggttgtctaa attgtccaca tatagttatt   48360
catagtattt ctaaacttt gaatttctct atgaccaatg tgatgtctcc attttctttc    48420
tttctggttt ccatttcatt ttttcatttt tgttttgtt tgttttttga gataaggttc    48480
ttctatgtgc ccaggctgga gtgcagtggt gcaatcatag ctcggtgtaa ccttgaactc   48540
ttggactcga gtgatcctcc cacctcggcc acccagttag ctaagactac aggcttgcac   48600
caccacacca agctaatttt tttaaaaaat atatttttta gaaaaaagtc tcattgtgtt   48660
acccaggctg ttatcaatct cctggcctca agtgatcctt ctgcctctgc tttccaaagt   48720
gctgggattg caggtgtgag ccattgcacc cagcctccac tttctttctt ggtgaataat   48780 ttgacccta ttttttttcac ttggctattc taagtaaagg tttgccaatt tgttgatct    48840 ttgcaaagat ccaattttg gttttattga ttttattgct tttctatttt ctatttcatt    48900
tatctccatt ctaatcttta ttatttcctg ttttctagtg gtgttgggtt gagtttgctc   48960 ttattttct agttccttaa ggtgtaaagt taggttattg attcaagatc attcttcttt    49020
aacttatgtg tttacagcta taaattttgc tcttagaact gcttctgctg catcctataa   49080
atctgggcat gttgtgtttt cattttatt tgttcaggat acttttgat gtcccttgtg     49140 atttcttctt taacccattt gttgtttaag agtgtgctgt ttaatttcta tgtgcttgtg   49200
agttttctag ttttccttct gttcttgatt tttaacttta ttccactgtg tccagagaac   49260
atactttgtg tgatttcaat catcttaaat ttgagactta ggaccaaata tatgctctat   49320
actggagaat attccatgtg ctctttagaa gaatgcttat tctgctcctg tcggtggaa    49380 cgttctgttc atgtctagtg tatgcgattg gttaatcgtg ctttttcaaat tccctatttc  49440 cttgatggtc ttctgtagtt tttctattac tgaaagtggg gtattgaagt caccaactat   49500
tattactcac aatgtaacca tatttaaccc tttacttta aaattctttt tggaaactgg    49560
aaggatctgt aaccaccacc cactcccaca tcagacccta tgcatatgcc aactgtctgc   49620
tgctcagcag ctgtgatggt tgttccagtt ctttattagg caaagaacag ttgttttttt   49680
gtttttttgt ttttttttt taacatttc ctttaaggaa ggtggctcag attgctaagc     49740
cagccaggcc ctgcgggaca ggctgcgcct agggtcacct gctcttcttc agcaactcag   49800
aaatattctc cttgaccatt gaatccaatg ttgaaaagtc ccagtcggcc aactgcatta   49860
gtcgatcatg ggcctcccta aagaggccag agccaatatt cagctccacc tgcatacgcc   49920
actcagctag cttggagctg ttgaggaaga cattatagtt ggctgccatg ggctgtagat   49980
agacgaagac aaagacgtgg tcagcctggg gaccagcccc acctgggtcc tctcccacag   50040
cctcaggccc acgtccctaa catctaccta tgcaaagaat taggctgctg accccaagg    50100 cctgagcaag gggtcacaga ctatgtaata gatgtaggtg gggatggagg atccagaatc   50160
cctcagagtc ctcagtcact ggtcttcttg ctccaagcct tctgaaccat gctgagaggg   50220
ctcctggccc aggcacttcc cacttctcca gcctgcgacc tcgcatgaat cctgccttct   50280
tccagggaaa ccccttatcc caggtgtgta tatgtggatg agggagagaa ctcaggtttt   50340
ttcctccatg tttagcctcc cactgtgatc aagctcaggg gctaggatgg agacctggc   50400 gggcagtcta ccctgcagtt tcgctggctt actaagagtt tggtttgcac ccaagatctt   50460
tgggaagccc aagaatgggt gtgtgtgggt gaaatgtaag gggtgggac gaagcatatg    50520 gctgaaccct tggggcaggc cagaatgatt tttcctggtg ctggtctgcc ctgcaaacag   50580
accaaggaga ctaattttca tatcagccag agatctctgg gataaggaaa agaatactgc   50640
```

-continued

```
attttctggt caatccacca ggaccccagg tccctcctct cgggcatatc tctggctgat    50700
atgcaaatta gtctctttgg tcagtgtgca gtgccctagc tggtgtgcag gatggccagt    50760
tgagaccctg gccagtgtct tgacaagcag aactggtcac cctccctgc atgtagaggc    50820
cacataaatg ccccacactc aggtgtgcct ccaaatgcac agtggatgcc cctcagaccc    50880
agccacgaga gctgtcctcc agagctgtct gtctggagct ctgggaaaca ggcagggcca    50940
gaaggacacc caggaagcca gtgaacattt cctggagagt ccagcaagag gaggaggtat    51000
ctgggatgct ggtggattga gcaggaaatg cagtgttctt ctctatccca ggctcaccct    51060
ccgggtcctc ccacaccgaa gaatctttgt caagtgtgga gaactgtgat ccttcctgat    51120
tcataacatt ctgtgcttcc tgttgccccg attgagtcca ggccccagg cctggttccc    51180
gcagcccca tggcagctct gcctgccttt cccgcctcac cagcctatcc tcaagtgatg    51240
gccccattgg tcacagagga gtcctacctc tgcccagggt ctaaccctcc tccaatccac    51300
tccacacctg catcatctcc accacggcca ccaggtcagc cagtgagatt tggttcccgg    51360
tgatgaacat cttatcctgc agaaaatact cctcaaagag ctgcaggctg ttcttcacct    51420
cttccactgc atgctccatc ttctcagctg aaacttcctc ccctgttatc tttgggatca    51480
gcaactggcc agggttggga agaggaggga agaggaggct gcactccagg gccacctgcc    51540
ctgccaggtc tctgtactct tgtctgctgg atagatattg aacacttccc aggatataaa    51600
gcagtttcac ctcttttagc agttctgatt ggtggaagtt gctgggaacc atgtgttcac    51660
aaggatttgg ggagctcagc aggcataagt cctgtgattg attagtgatg tctgtcacag    51720
gcatagaatt caaagtagag acacatgtac tggttatttg tcatcttcta attttctata    51780
ggccatactc ttttttgttt ttgtttttg agatggagtc tcactctgtc gcccaggctg    51840
gagtgcagtg gcacaatctt ggctcactgc caactccaac tcctgggttc aagcaattgt    51900
cctgcctcag cgtcctgagt agctgggatt acaggtgccc atcaccacac ccagctaata    51960
attttgtatt tttagtagag atggtgtttc acaatgttgg caaggtaggt cttgaactcc    52020
tgacctcaag tgatctgccc gcctcggcct cccaaagtac tgggattaca gttgtgagcc    52080
accgtacccg gccttctgtg ggccttttga cgctgagatt ctctagttca gaatgaaatg    52140
cctcgaatgc tgtcctgggt gagtcacatc agcccctccc gtatgccctt ccctcgccc    52200
taataagact ctttcatgcc cattgtttca gtccacactc ctgacggctc tgtaaggcgg    52260
gcaggagaag gagctgagga aatgaggccc agagagggag ggagacttgc ttgaggtcgc    52320
cggcagtcag cagggccaga actggcctcc agccttcctg acttccctgt gcccgtgtcc    52380
ccaagcccca gaagtggccc tgctcacctt gagccagact atcttcttca tgggcagctg    52440
aaaggccgtg tgttgccaag ccacgaactc atccacacgg gcacgtgcgt gcaggtctgg    52500
cgggcaccag tgcgatggtg cgctgtactt gcggcacagg tagtaaagga tggccgcgct    52560
gcagaagggg ccggtcaggg gcactgccct tgccttcctg agtgccacta cgtcaaccac    52620
cccggtgtgg cctgggccca actgctgggg cttccagagc aaagaggagc ccaaacggcc    52680
ccgagaaaga ccttcaccag agctgtctgt ctgacagtca gtaagggctg ggaaggagcc    52740
ctgcggggtg agtaggagtt gggggctggt ggtataacaa agagtaggcc agcagggga    52800
acaacacgtg ttgaattggg atgctgaggt gggaggatca cttgatccca ggaatttggg    52860
gctactgtga gccaagatca caccactgca ctccagcttg ggtgaaagat caagatcctt    52920
tttcaaaaac aaaaacgggg gggcacgatg gctcacacct gtaatcccgg cactttggga    52980
```

```
ggccaatggg ggcagatccc ttgaggccag gagttggaga ccagcctggc caacatggtg    53040
aaaccctgtc tctactaaaa tgaaaataca aaaattagct agttgtggtg gcacacacct    53100
gtaatcccag ctacttggga agctgaggca cgggagtcac ttgaacctgg gaggcagagg    53160
ttgtagtgag ccaagattgt gccactgtac tccagcctgg gccacagagc aagactctgt    53220
ctcaaaaaac caacaaagaa aaacacatgc tgaaatacga gggtaaaggg agcaaggtaa    53280
atctgaagaa aagagagtag ggggttgcaa ctggaagaag ggtgggggtg attggggagt    53340
gatgaggcag ccagagacac tgtggagtcc acgtagggta gcccctggag gtgcagggag    53400
gttatggact taatgcttaa gattaggcat tatataagcc agggcatgaa aggatccatc    53460
tctctggtgc tggatggagg gtgagcccga ggggcagaa tggacaatga ggtggcgggc     53520
cagcaactat cgggaaggtt gtggtgtctg gggatggtgg aggccatggg gacagaggga    53580
aggggacgga ggggagacat gcttcggagg ggatgtccta ggccttgctg attgatggct    53640
ggtgtgggaa cctccgcagc acaagggctc ctttatcatc accaacagca accatgccaa    53700
ggtaaaaagg tcagggcatg gagagagcta tcggttaaaa agtggcagga gagacagcaa    53760
ctggctgcaa gactcagaac ttctttggat cctgatccaa acaaactgcc aagaaaatat    53820
ttaggagata atcagagagt tttgaacagg agccacgtat tagatgaaat ccaggaatta    53880
ctgttaattt tatgaggtat cttaatggta tcgtagtgat gctacgctct atcctagccc    53940
aggctggagt gcagtggcac aatcagagtt cactgcagtc gtgaactcct ggcctcaagc    54000
gatcctcccg tgtcagcctc tcaaagtgct gggattacag gcatgagcca ccgcgcccag    54060
cctgttgctt tttttttttt tttttttttt tttttaaaga acgcttatct ctaagaggta    54120
tgttcctgaa cgtttattga tttatttact tacttatttt tattttttgag atggggtctc    54180 actctgttgc ccaggctgaa gctcaatctt tgctcactgc aacctctgcc tcccgggctc    54240
cagcaatccc tccacctcag cctcctgagt agctgggact acaggtgcgg accaccatgc    54300
tggctaactt ttgtattttt tgtagagatg ggggttttgc catgttgtct aggctaggct    54360
ggtcttgaac acgtgagctc aggccatccc ctcacttcag cctctcaaag tgctagaatt    54420
acaggcatga gctggcccct aaacatttat gaatggaatg atgggtgtc tgggaggcag     54480 gggaatagaa atgatgtaaa ctggacccca agttggcaag agtcagagct gggcgatgga    54540
tttgtggggt tcctcgtgtc cctcattagt tagtattcac tctcctttag tgcacgtgtg    54600
agattttcca tggtcaaaca gacaaatgct cgcactgaac ctcccaggag gagcagagac    54660
agatggtgca agggcccag ggaagactta ccttcactt aagataaatt tcccatcttt      54720
gaggctggga agcttcctga gggggttgat gtcaatgtat tctttgctgt ggtggtgacc    54780
tgggaggagc agggaaggtc tgaggctgtg ggactccagg ggagagagaa ctgagactcc    54840
cagagacaca aacgcctccc tctctatttt ctcaagaaga gaggactgag gcccggaggg    54900
acatggcggc tcacccagg tcacagggca aggcagttgc agaaccggac tgggatcaga     54960
actgctggct cccagcctgc tccacccag gtttggtgac tcccgtgcct cctacctgtg     55020
tcccaggacc aggacgaccc ttttacccag aagccggagg cctccagtgc ccaccccaa     55080 agctggatct gaaaacacag cctttgaatc acctgaagcc ctgagggcct gggtcccatc    55140
cgcaatccca tcgctctcac tctgtctcca ctttaaggaa gccaggccca gcacacagct    55200
ggacatccaa agggaagctt ctcggacaca atcagggtca tcttaacagg gaacctgagg    55260
tgggggcagg aactgaaact cttcctggac cagccgcctc cagttggaaa catttctggg    55320
ggctccactc gcagcccgtt catttccaca gcttccctgt ctcttcctct gtgttctaga    55380
```

-continued

| | | | | | |
|---|---|---|---|---|---|
| ggcttctgct | tttgcaggct | gagttttgga | gtccctctgt | gctcgggatg | gagttggagc | 55440 |
| ccaccectct | gaccctcact | cgggagcagt | ggagccctga | gcctttctga | acactgggga | 55500 |
| ggatgggtgt | agacggactg | tgcacttctg | ccccctttgc | caacctggtg | ggcaggtgct | 55560 |
| gagttcacaa | ggtcctagaa | tcccacaacg | aagccaggt | gcctggtggg | agcccaggga | 55620 |
| gtcccagctg | ctgttcattc | cccttctcc | tcaaaaagcc | tgttcatctg | tggcgtgggg | 55680 |
| actatcatta | gtggggagtg | gctaaggtag | gctaggcagg | gacgcagcct | acaagccccg | 55740 |
| tggcatcttt | tccttccctg | tggacctctg | gggtgattcc | cttgtctctg | tccctgcttc | 55800 |
| tcagaaatgc | ccctatcaat | ctgagcgtgg | tggctcacgc | ctgtaatccc | agcactttgg | 55860 |
| aggctgaggc | ggggcagatc | acttttggtc | aggggttcga | gaccagcctg | gccaacatgg | 55920 |
| tgaaactcca | tctcgactaa | aaatacaaaa | aatgagccgg | gcatggtggc | gtttgcctat | 55980 |
| aaacccagca | actcgggagg | ctgagctggg | agaatcactt | gaacccagtg | gagattgcag | 56040 |
| tgagccaaga | tagcaccact | gcactccagc | ctgggtgaca | agtgaggct | ctaccaaaaa | 56100 |
| gaaaagaaa | aaaaagctc | caatctgtgt | gtcctgcctc | ccccaggac | caggcctgcc | 56160 |
| aggcagcagt | gggagctgac | ctttcagcag | atccacaaac | tgaaagttga | actggatgtc | 56220 |
| atgcttcttc | gagaagatgt | agacggcacg | gcagggtgct | gacagcaggt | ccatgtagag | 56280 |
| ctccagggcc | atgttgagac | acatgccagg | ccccacagct | gcagctggcc | agccacagac | 56340 |
| ctgggcctat | gtctgccag | agtccctggc | cctgtgccct | ctccgatctg | ggcccaggac | 56400 |
| cctgcattct | ggaacctctt | gtttcccttt | gtgttgtcat | aaggccagga | agcctgcaat | 56460 |
| tctcacagca | tcaaggattc | taaggaggcc | caggagtagg | ctggcagagg | cccgtggcaa | 56520 |
| aggtgtggca | gccgtgaccc | tactctcccc | ctctcacgtg | tgtctgtgtc | ccgtggcgcc | 56580 |
| acctcacaga | caccctgtct | gagaagggat | tatgcctggg | aattcccagg | gccggacttt | 56640 |
| gattgcagaa | cctgacgaaa | ggggctttgc | agggtccaga | atgaggagga | ggcaatgaga | 56700 |
| attatccctg | gaggattcta | gaagtagagg | ctggagcat | ccacaggtga | atggagcctg | 56760 |
| aactatgact | agaaaggaat | tgggagaaag | agacacagga | acctgggagc | ttcgggagca | 56820 |
| gtggggacac | caccaccagg | aagtcagggg | gcactcggca | atgaaagtgg | cagatgcaat | 56880 |
| aaaacttta | acatattgtt | gtataatgta | caataatgta | ataaaaatac | accccctata | 56940 |
| cattattgtt | ccaactctag | ctctatctat | tgccctcctc | atatgaatcc | ctctccccat | 57000 |
| accccattct | ctagttaatc | ttaactaggc | ctcctgttta | tattagccac | atcaagccta | 57060 |
| gctgtctact | ctatcctgtg | atcaggatga | gcatctaatt | tgaaatatgc | actcatcggt | 57120 |
| gcactatgta | cagtggccca | aacagtctca | tatgaagtca | ctctagctat | tatcctccta | 57180 |
| tcagtcctat | taataagtgg | ttcatttaat | ttgtatatac | tcattggaac | agaagaattt | 57240 |
| ctctggctgc | tcctaccatc | atgacctctg | gccataaat | gacttatttc | cacactagca | 57300 |
| gaaaccagcc | gagcctcttt | agacctaaca | gaggggggat | cagaattaat | ctcgggcttt | 57360 |
| aacgtcgaat | atgctgcagg | cccatttgcc | ctgttcttta | tagcagacta | tataaatatc | 57420 |
| attataataa | atgccctgaa | ggccgcaaga | ggttcgtggg | tgcagtgcac | aggagaccat | 57480 |
| atctggggac | agcagctgca | gcagacccca | agctgggcca | tccctgccac | ttgccaggtg | 57540 |
| gtgcttggcg | aaggcaagca | gctcccaccc | gcccggggaa | tacagcgcga | ccccggcgg | 57600 |
| catgctcttc | agcaccaccc | caggaggtac | caggatcatc | taccactgga | aattcctgat | 57660 |
| ggagtgttga | aacttacccg | tgaccaaaac | actcccaagg | gatctgccca | ccattcccgg | 57720 |

```
ggtcaccagc cctgccagtg atgatccccc caacggaagc cagccagagc cacctgagca    57780
atagtccaga agataagcag ggcgggcagt gaagaagcac agttttgaga tggacattta    57840
aagcaccagc catcgcatgg agcactgcca agggacccct caggcccttc ctggaggagt    57900
cccaccagcc aggccttatg aaagtgatca tactaggcag gcattggtgt ggggccagtc    57960
accccagccc tctctccctc actcgcggca cctgccccct cctctttgtg aacaccagca    58020
ggtacctcct tgtgcctccg ctgatgcagg agcagctgcc caaggggag taaccccctgc    58080 cagcacaccc tgcagctgag ggccaggaag tggacaagaa tgaaccctt cttccaaatg    58140 atcagctctt ccagcccctg ctgggggccc cacgacccct tccttaggtt gacgtgcctg    58200
ggaaagctca cctcccccctc ttccctaaga gaggaaataa aagccacctt cgccctaggg    58260
caaaaaataa ataaataata aatcccgtaa tcactattgt cttcctagga gcactgcata    58320
acatatatat accagaactc tataccacaa atttcgtcac ccaaactctc attttaacaa    58380 gtctttttttt atgaattcga acatcatatt cctgattcca ttatgatcag ctcatatatc    58440
tccttgaaaa aattttctac cactcacact agtactttca tatgacatat cttcatgcca    58500
gtcctaacct ccagcatccc accccaaaca taagaaatat gtctcacaaa agagttactt    58560
tgatagaata aattacagag gtttaaaccc ttttgtttct agaattacag gaattgaacc    58620
tacccatgag aatccaaaat tctccgtgct acataataca ccacatccta tcacacccca    58680
cagtaaggac agctaagtaa gctattgggc ccatacctg aaaatgttgg ttataccctt    58740
cctatactaa ttaatcctcc agtgtatgcc atgcagagga gcccagaaac ttcctggcct    58800
gggttggggc tgcagtggcc agactgtgca cctggtggcc caggaaggta actagagccc    58860
cacgtagagg actgagtgcc actcactcta tgctttgtga tttaataggt ctaggctcag    58920
aaatgggact gatcccactt ccagtgacag agtaagcctg gagacaagcg aagagcatgc    58980
agtgtgttta ttgcagacag cagggtgcag tgcagtgggc tgtacccact cagtggagcc    59040
actcctgcag caactgcacc tgcttctggg ccagctgggg gtcctgccga gcctcactgt    59100
ggttcagagg ctggagtatg agcttgtggg cctccaggaa gagctcagta ccaagggcag    59160
ccttcatatg ggcctgtcac actgccagcc agggccagtc ttggaagagg tcgcagccaa    59220
cggcagtggg ctgggaagac agggcagctg gggttggggc tcagccccat gcccagagtc    59280
cccccgaggg caggtgggta ggaaagcttc acctgcatca cctccgtcag caccaagtct    59340
tccagggaga tctgctccat tgccaggaag ggcctggcca ccaggacccc cccatccagg    59400
tgctgcaggg ctggcgtcag cctccccaac agccgctcca gctgtgcagc atctgcaggc    59460
tgtctggaga agtggggcag gagagactgg gctgtgagga gaggagcaac ttaacccaga    59520
ctcttggaag cctcttgggc ctcctctcca tcccttcccg gctgccattc attagtgatg    59580
tcctctgggt ctctgtgttc agaaggtttc taaggattca ttcaggctta ggggaaggag    59640
tactgtgata gattagttat gtctgctgag gacagtggaa gtgaagctaa tatgtaatat    59700
gtaccaactg gtaccttcca tctctggggg tccaggcccc tgcccagcc tgcatgacag    59760 ggcctaggaa gctcaccttg cacaggtaga cattggtggc aggcagctgg atggtgacat    59820
gcttccacgc caagtactca tccacgcagg tgcgggcttg cagctcaggt gggtaccagt    59880
gtccccgtat ctggtacttt cgactcaggt ataaaacgat gaccatgctg tgggcagggg    59940
gtgtcagaga tcttttctcc agcctgtcag ggccaggtgg cttcattgct catactcagg    60000
gtgatttgac caggttttct ccccaccttc accttcaggg gaggacctcc cctatactgc    60060
aactccctcc aggcagtatc tccccacgac caaaccactc tgtttctcca tttccaactc    60120
```

```
tgatcctccc tgggcccatg tttccacctc ccctcccagt taccatacca tcctgccctc    60180
tgtgcccagg ccccactccc tggcatcagg gtccccactc agagtgcctg ccgtgtgggc    60240
cctgcccaaa aggtctccaa gttcccttcc tagtgcccca gaacactagg tgcccatttt    60300
ctatcctcag gtaagccctg ggaggtggat acattattcc tcccactccg ttttacagag    60360
gagaaacctg gcacacaaag ttctgtgatt tccccaaggg catggattga ggaagtggtg    60420
agctgggatt gaatgtggag tctcccctgg gtctgcccag ctcctaggac tctgaaagga    60480
tgagctgggg acatttgggg aggagccagc ctcaagcctg ggccttgccc gctggcttca    60540
ggttgtccag gtttatctgg gtgacctacg tcctttcccc atctgggcag ctccagctgg    60600
cttagactct agccaggttc cagcctccag ctttagccca aggtgcccc tgggtccagc     60660
ctctgcatcg gagctacaca ggctgaaatg aggaaggggc cacagtgatt tggaaagatc    60720
tccaacccaa ggaaagatct cccctctcgc ctctgcctcc ccctacaact ctgagcccca    60780
gaacccaggc agatcctggc tctgaccctg ggtgggcacc aggtcaccat tacctctctg    60840
ctagtaggaa gtcgccatct ctgagggcag gcaccttccc caggggggttc accttcagga   60900
actcaggctt caggtgctcc cctggtgggc agaaaggaga gaaggctcag tgcagggcct    60960
ggtccttggc acccactcca tggggcccag cccagccacc tggctcaccc caagccaact    61020
ccactgtctg cagctgaaaa gggatgtcat tctgcctggc aaaagtggat agcatggcag    61080
ggggctgagt gcatgtccag gaacagcttg ggccccattg ctgctcctcc cacctgccct    61140
ccccagaggt ctgtacctcc aggagttgct cagcccttct cggccagtgc cttcccccaa    61200
aatggggcca gaactctgta ctcctcctga agcctattcc ctccatgact ggctgggagg    61260
cctgccaagc ccctctcccc ttttctccac ctctgtagag tggaggcagg ggtggccagt    61320
gtcccttggg gggtttcaga tagaaactca atgacaattg gcttagcaaa acaaacaaa     61380
caaaaaaaaa acaacaaaaa aaaacaaag ggagtggggt gggtgggag atttctcaga      61440
aaacttctcc agtcatagga ggggagggggt gtagaagcca ctaagagaac tggaatcaga   61500
acctgtttct gtctccccac ttttcctccc ctctcctcct ctccctcct tccctcctg      61560
tccctcccc tcctctcccc tccctccct tccttttcct tccttccctt cctctttcc       61620
tcccttcttt cttgagaca ggatctctgt ctccctacac tttttctttt taattctctg     61680
tctctttctt gacatagaat cttgctctgt cacccagcct ggagttcagt ggcacgatca    61740
tggcttactg caatctccaa gtcctgtgct ccagcagtca ttccactaca gcctctggag    61800
tacctaggac tacaggtgca catgaccata ccccactagt taaaaaaaac aaaaacaaaa    61860
acaaaaaaac ccttgggcct ggcagggcgg ctcgtgccta caatcccagc cctttgggag    61920
gccaagatgg gctgatcaca tgagcccagg acatcaagac gagcctgggc aacgtgccga    61980
aacccagtct ctacaaaaaa tacaaaaatt agctgggcat ggtggcgcat gcctgtagtc    62040
ccagctactc aagagactga ggtggcagga tcacttgagc ccaggaggca gaggttgcag    62100
tgagccaaga tcacgccact gcgctccagc ctaggcaaca gagccagact ctgtctcaaa    62160
aaaaaaaaa agagagagag acagataggg tctcactatg ttgtccaagc tgatcacaaa    62220
ctcctggcct aaagtgatcc ttgggtctca gcctccgag ctgattagct gggattgcag     62280
gtgtgggcta ccacgccctg ttatcactcc cttctctga gtcagctttt ctctctcaga     62340
ctagcctact ccatgaactc aggaaatgtc actacaggtg gccccagctc ccatttacct    62400
ccccataggg agctcctctc tccagttcca atttcaaaac tcccaaggaa gcattctggt    62460
```

```
tcactcgctt gggccactgg ccagagggat gggatactct gaaagattca gctagagtcc   62520
cgggcccagc cctggaccat cactgtgcac cctggttaga tgccagggct gggattcagg   62580
gagaagaaag gaggttcccg gacagtcatt cctgcctcct gcggctgcgg gctccctgca   62640
cagtcattcc tgcctcctgc ggctgcgggc tccctgcccc catcctgtgc acgaagtggg   62700
agctcccgct gtctggcagc agctgctctg caggggacag tctggacggc agaaagttca   62760
tccttaaccc cagccttcca gtcaaggttc ccacaagtct gggacacctg caagtgtcat   62820
atcccgctgg gtgaaagtct gagatccctt ttagaggatc ccattcgctc cctcccttct   62880
gccaccttcc agctccgaga aacagagctc tgaacgaacc ctcagatgtc catgcgctgg   62940
ggcctttcca ggacggcggg cgcagtcctt tctgggttg gggtgacacc tggaaacatg    63000
taaggtccct ggcacaggga cccctcccag tttcaagcga ttctcctgcc tcagtctccc   63060
gagtagctgg gattacaggc gcccaccact gcacccagct aattttttgt gtttttagta   63120
gagatggggt ttcaccgtgt tagccaggat ggtcgcgatc tcctgacctc gtgactagcc   63180
cgcctcagcc tcccaaagtg ctgggattac aggcgtgagc caccatgcag gccaatttt    63240
tgtattttca gtagagacag ggtttttacca tattggacag gttggtctcg aactcctgac   63300
ctcaggtgat ctgcctgcat tggcctccca aagtgctggg attacaggcg tgagccacca   63360
agcctggtgg taatttataa ggggtggaca tttgttggct catggtcctg aaggctgaa    63420
agtccaagat cgaggggcca gcatctggcc agagctttct tgctgtatca tccctggtg    63480
aaaggataaa gagagggtaa gagagagcaa gaggctgaac tcacagcctc aaagtccttt   63540
tataatccac atcaatccat ctgtaacggt ggaggcctca tgagataaac acctctcatt   63600
aggccccacc tcccaacact gttgcattgg ggattacatt tccaacacat gctttgtggg   63660
ggacccattc aaaccacagc acagggacac cttctctttc cttcctgtga tatgctgaat   63720
aatgaccct aaggatatac aagtcctgat ctctggaacc tgtgaatatt accttctgtg    63780
gcaaaaggga ctttgcagaa ttgattaaga atgttgagat ggaggcattg tcttggatta   63840
tctgagtgag ccctaaatgc agtcacaagt atctgtgtaa gaggagacag acggagattt   63900
gaaacagaag acaggagaag atggaagcag agagatttga agatgctaca ttgtgggctt   63960
tgaagatgga agaaggggct acatgaccca agacaggcag ctccaaaagc tggaaaaatt   64020
gaggaaacca attcccctct cagagcctct ggagggtgtg caaccctatt ggcacctggg   64080
ttttggccca gagaaataga ttataaagtt ctggtctcca taactgtaag agaatagatt   64140
tatgttgttt taagccacca aggtggtggt aatttgttat accatccaga ggagaggaac   64200
acagattttg gtgccaggaa gcagggtgct gctataaaaa agaaaatcta ggctgggcac   64260
agtggctcat gtctgtaatt tcaacatttt cggatgccaa ggtgggtgga ttacttgagc   64320
cctggagttt gagactagcc tgggcaacat ggcaaaaccc cgtctctact aaaaatatat   64380
aaattagctg gggatgggcc gggagcagtg gctcacgcct ataatcccag cactttgggt   64440
ggcaaaggca ggcggatcac gaggtcagaa ggttgagacc atcctggcga acatggtgaa   64500
acccagtctc tactaaaaat acaaaaaatt aaccaggcgt ggtggcgggt gcctgttgtc   64560
ccagctactc aggaggctga ggtagcagaa tggcatgaac ccaggaggcg gagcttgcag   64620
agagccaaga tcgtgccact gcactccagc ctggggaaca aagcgcgact ccgtctcaaa   64680
aaaaaaaaaa attagttggg gatggtagtg catgcttgta gtcccagcta ctggggagac   64740
cgaggtggga ggattgcttg aggctgggaa gtctaggctg cagtgacctg tgactgtgac   64800
actgcactcc agcctgggca acagagtcag accctgtctc aaacaaacaa acaaacaaaa   64860
```

```
atctaaaaat gtggaagtag ctttaaattt gggtgatgtg cagaggccag aaaaattatg   64920
aggcccatga tagagaaaac ctagattgcc ttgcacagat tgttggtaga aatatggatg   64980
ttaaagacta tagggagggc tcacgagtat caactaaaca tggtcagagc aagtctacat   65040
tgccttacag catacctaag tcatcatagg cagctgtagg tagatatata gatattggct   65100
gggtgcagtg gctcacgcct gtaatgccag cactttggga ggctgaggtg ggtggatcac   65160
ctgaggtcag gagttcaaac cagcctggcc aacatagtga aacccgtct ctactaaaaa   65220 tacaaaaatt agctaggcgt ggtggcatcc cagctactag ggaggcggaa gcaggagaat   65280
tgctcgaacc tgggagacgg aggttgcagt gagccaagat tgcgccacta tactccatcc   65340
tgggcgacca agcgagaatc tgcctcaaaa aaagaaaaaa tagatattaa aaatcctgct   65400
gctgaggact ctgaagaaat gaggaacgtg tttctggaaa ctggaggaag gaggatcatt   65460
tcccagaaaa ggagcccgta gggaggtaga aagcttagtt gaattgtgtc cgatagttat   65520
atggtgggtg aacttaaagc aacgaagttg gatatttagc tgaggagact ccaagcaaa   65580 gcgttgaagg tgaagcctca tttcttcttg ctgtttatgg tgaaaagcaa gaggaaagtg   65640
ataaaatgag gaaaagctg ttaagcaaaa agaaaccaag gtttgatgat ttgggaaatt   65700
atcagcctgt gcagattgca aaagatgcta aaattagaag attcgctgtt tggaaaacac   65760
aactctatcc ctgtcctggg gatcactcaa gacttgtatc catagacaac cagatttcta   65820
tgggcttgaa ctctgtgtgt gtgtgtgtgt gtgtgtgtgt gtgtgtgtgt gtgtgtgtgt   65880
gtgtgtgtgt agcaaggttg ggggagcaca gtggaaagac cttgaattta tttgtttatt   65940
ttttagacgg agtcttgctc tgtcgcccag gctggagtgc aatggcacga tctcagctca   66000
ctgcaacctc cacctccagg gtggttcgag cgattctcct gcctcagcct cccgagtagc   66060
tgggactaca ggcgtatacc actatgccca gctaattttt gtattgttag tagagatggg   66120
gtttcaccat gttggtcagg ctggcctcaa attcctgacc tcaggtgatc aggctggtct   66180
caaactcctg acatcaggag atccaccagc ctcggcctcc caaggtgctg ggattacagg   66240
catgagccac catgcccagc cttattattt atttatttat ttttgagaca aagtctccct   66300
ctgtcaccca gactggagtg cagtggcgca atctctgctc actgcaacct ctgtctccca   66360
ggttcaagtg attctcccag ctcaacctct caagtagctg ggactacagg tgcgcaccac   66420
catgacctgc taattttgt attttattt atttatgtat tattttattt tattttcca   66480 taagttattg gggtatgggt ggtatttggt tacatgagta agttcttttg tagcaatttg   66540
tgagattttg gtgcacctgt caccccagca gtatacactg caccatattt gtagtcttt   66600 atccctcacc ctcctcccac tcttcccctc aagtccccaa agtccattct tatgcctttg   66660
cgtcctcata gcttagctcc cacatatcag tgaaaacata agatgtttgg ttttccattc   66720
ctcagttact tcacttagaa aatagtctc caaactcatc caggtcactg caaatgctgt   66780
taattaattc cttttcatga ctgagtagta ttccacatat acatattcca tatatattca   66840
ttccatatat atattccata tatgctcatt ccatatacat attccatata tgctcattcc   66900
atatacatat tccatatata ctcattccat atacgtattc catacgtatg tactccatat   66960
acgtattcca tacgtatgta ctccatatac gtattccatg tatgtattcc atacgtatgt   67020
attccatgta tgtattccat gtatattttc catatgtata tattccatgt atatattcca   67080
tatgtatata ttccatatat attccttatg tatatattct gtatgtatat actccatgta   67140
tatattccgt atatctatat tccatatatg tattccgtat gtatatattc catatgtact   67200
```

```
ccatatgtat tccatatgtt ccatatatat tccatatatt ccatataaat tccatatatt   67260
ccatatatat cccatataca ttccatatat tccacatata ttccatatac attccatata   67320
ttccacatat attccgtata ttccatatag attccataca tttattccat atatattcca   67380
tatagattcc atatatattc agatatattc catatttata ttccatatat ggaatatata   67440
tgtattccat atatatgtat tccgtatatg tatgtattcc acatatatat tccatatatg   67500
tatgtattcc acatatatat tccatatacg tatattccag atatatactc catatgtata   67560
tcccagatat atatattcca gatgtatata ttccacatat atattccaga tgtatatatt   67620
ccatgtgtgt atattccata tatgtatatt ccatgtgtgt atattccatg tgtattccat   67680
atatatattc catgtgtgta ttccatatat atagtccatg tgtgtattcc ctatatatat   67740
tccctatata tatattccct atatatattc cccatgtaca ttccatatat atattcccca   67800
tgtacattcc atatatattc cccatatata ttccatatat attccccata tatattccat   67860
atatatattc cccatatata ttccatatat atattcccca tatatattcc atatatatat   67920
tccccatata tattccatat atatattccc tatatatata ttccctatat atattcccta   67980
tatattccat atatatatat atatatatat atatatatac accctatata tatattccct   68040
atatattcca tatatatatg gagtctcgct ctgttgccca ggctggagtg cagtggcgcg   68100
atctctgctc attgcaagct ccacctccca ggttcacgcc attctcctgc ctcagcctcc   68160
tgagtagctg ggactacagg tgccagccac catgcccagc taattttgtt ttcgtatttg   68220
tagtagagac ggggtttcac catgttagat aggatggtct cgatctcccg acctcgtgat   68280
ccgcccacct cggcctccca aagtgctagg attacaggct tgagcctccg cgccggcct   68340
ctgaattctt tttcaggtaa atcagggatt tcttcttggt ttggatccgt tgctggtgaa   68400
ctagtgtgat atttgggggt gttgacgacc cttgttttgt catgttacca cagttggttt   68460
tctggttcct tctcattggg gtaggctctg tcagagggaa ggtatagggc tgaaggttgt   68520
tgttaagatt tttttttgtcc cagggctatt cccttgatgt agtctctccc cctttcctg   68580
tggatgtggc ttcctgtgag ccaaactgca gtgattgttg tttctcttct gggtctagct   68640
gcccagtgag tctagtcagc tccaggctgg tactgggggt tgtctgcaca gagtcctgtg   68700
atgtgaaccg tctatgggtc tctcagccat ggataccagc acctattctg gtggaggcgg   68760
cggacggtgc agtgcactcc gtgagctttg gtggtttaat gctctatttt tgtgctggtt   68820
ggcctcctgc caggaggtgg ctctctccag aaagcatcaa ctgtagtagt gtggagaggg   68880
gccagtggtg ggtggggccc taggactccc aagattatgc gtcctttgtc taccactact   68940
agggtgggta ggaaaggacc ctcaggtgag gacggtgcta ggcatgtctg agatcagact   69000
cttcttgggc aggtgttgct gtagctgctg tggaggatgg gggtgagatg cccaggtcat   69060
tggagttgtg tgcctaggag aattatggct gcctctgctg agtcatgcag gttgtcaggg   69120
aagtggggga aagccggaag tcacaggcct catccagctc ccatgcaaac tgaaggggcg   69180
gtctcactcc caccatgtcc tgcaaacagc cctccatctg gaaacagcaa acagtgtgtt   69240
tccagatgga gggccagacg aattgaaaac ttgcctgagg ctttccacct cccagctgcc   69300
aaagaaaagg gctttagttc ttcctccgcc tgtgaaatct gcaagccaga ttcacaccct   69360
cccctgggtt ctggcccaga ggcttctcac cccattcaaa ttgttacaaa gttcagctag   69420
agaattcctt ctccctgtgg agctgtggag ttttacccct tgcttctgg ccaccctcct    69480
gatggatccc tgtggtgcca ggcaggaatg ggctgcttgg ggatccagtg agctcccagg   69540
gcctttctgc tgcttcctct gaccctgtat tttgctcggc tgagttttgt aacttgactc   69600
```

```
agctccagga aaagtcggaa acttcttcca caaacaggcc ttcagcttct ccagtggggg   69660
tgtgtgctca ggagaagcgg gtctcccttt cccacttcca cagctggggc actcacagta   69720
tttggggtgt ctcctgggcc ctacaggagc aagtctgctt ccttcagagg gtctgtggat   69780
cctctcagga ttgctggttt gttctttcag tggatctgca gctaaaattc acaatgcaag   69840
cctccacatg ctgctctgtc cggagctgca atctggctat gcctcccgtc tgccatgatc   69900
ccgaaatccc tctccaattt ttatatttt agtagagttg gggttttgcc atgttggcca    69960
ggctggtatt gaacttctga cctcaagtta tctgcccatc tcggcctccc aaagtgttgg   70020
tgtaccagga caagctgcag acaaaacctc tgagacacca agttaaagaa ggaagggctt   70080
tattcggccg ggaacttcag caagactcac gtctccaaca accgagctcc ctgagtgagc   70140
aattcttgtc cctttaagg gcttacaatt ctaagggtc tgtgtgagag gtcatgatc      70200 aattgagcaa gcagggggta cacgactggg ggctgcatgc accagtaatt agaatggaac   70260
agaacaggac agggattttc acaatgcttt tccatacaat gtctggagtc tatagataac   70320
ataactggtt aggtcagggg tggatctttta accaagccca aggtgcagcg ccgggctgtc   70380
tgcctgtgga tttcatttct gcctttagt ttttacctct ttctttggaa gcagaaattg    70440
ggcataagac aatatgaggg gtggtctcct accttattgg ggttacaggc atgagccacc   70500
gtgcccagcc aagaccctga atttaaatcc tgactctgtc attcattagc tcctgacctc   70560
aagtatgcca ttaactactt tgaatcctgg tatccttgct gtcaaaggag atgagagttc   70620
tgacacttat aggtccactg taagacataa ttttaaaat atctgtaaaa actgggccgg    70680
gcatggtggc tcatacctgt aatcccaata ctttgggagg tcaaggaagg cagattgctt   70740
gagcccagga gtttgagacc agcctgggca acatgatgaa accccgtctt taccaaaaat   70800
tcaaaaaaat ttagctaggc attggcacgt gtctgttagt cccatctgct cgggaggctg   70860
aagtgggagg atcactggag cccaggaggc agaggttgca gtgagccgag attgtgccac   70920
tgcactccag cctggcagag tgagaccctg tctctacaaa aatgtaaaat aaacttaaaa   70980
aatgtcaaag catgataaag tacaggacat aaagaccatg attaatctaa cacccatcac   71040
tacaatcttt gcctctgttc tggcattccc ctatgtgtct tcgcatcacc ctccttctgg   71100
gtgactcctt tatgttgtat ttttttgttt ggtttggttt tttggttag tttgttctga    71160 gacagagtct tgctctgttg ctcaggctgg agtgtagtgg tgtgatcttg gctcactgct   71220
acctctgcct cccaagtttg tacctcagcc tcccgagtag ttgggattac aggcatgcgc   71280
caccatgccc tgctaatttt tgtatttta gtagagacgg ggttttgcca tgttggccag    71340
gctggtctca gactcctggc tcaagtgacc tgccacctc agcctcctaa agtgttggga    71400
ctacaggcat gagccaccac gcccggccac cccactcatt ttgaatgtaa gtagattacc   71460
aattctgaaa tgggttttga gcagtagcaa cattgacaca aatttataat attttcaaga   71520
agatacttcc ttcaatatgt aaaatgcaac agatatcatt tgcaatcata catatgtaca   71580
tatatacata cacacatata atatatatat ctcaccatgg aataagtctg agctgaaaca   71640
tgcattactt aaaaaagaaa acacttacag acaggatctt gctccgtcat ccaggctgaa   71700
gtacagtggc acgattgtgg ctcactgcag cctcgacctc ctgggctcaa gtgatcctcc   71760
cacctcagcc tcccaagtag ctgggactac aggcatgagc tacctcgcct ggcctgcatg   71820
atctttatga agaatgtcat agaaagtttt tgaaagcgat taaagttcac ctaaacaagc   71880
agggatctat gctgtatgcc atgctattat tggggaggaa aaaaattctc ctctacattc   71940
```

```
ttagggtctc tggagatctg gaactaagaa taaaactgaa ataagacaga ttaacagaag  72000
aaaatcattc aagttttgct aaattttcag tgtacatggg tactttcaca agagaatgaa  72060
ggcctaaaga agtcactaaa gtagaaaaac aatacctttt tttttttttt ttttaagaca  72120
aggacgggtg cggtggctca tgcctataat cccagcactt tgggaggcca aggcgggcag  72180
atcacaaggt caggagattg agaccatcct ggccaacatg gtgaaacccc atctctacta  72240
aaaatacaaa aaaattagcc aggtgcggtg gcgggcacct gtagtcccag ctactcagga  72300
ggctgaggca ggagaatggc atgaatcctg gaggcggagc ttgcagtgag cggagatcgc  72360
accactgcac tccagcctgg gtgacagagc aagactctgc ctcaaaaaaa aaaaatgaca  72420
agacaaagcg gcttggatta tagggagtaa attgtggaga agggactagg acatacatgc  72480
ggagcaaaat tagaagataa ggattatttt tagtcgtgtg tttatacaga tccattggaa  72540
ccttgattca cagtcacttg tgatgacaat gttcttctct tcctggtaaa gggagggtgc  72600
tttcttatgg gaaattgtgt ggcctattct tagatagaaa agggcaggtc agagagtctt  72660
tcctgcatgt gctatttctc aagtgccttc aactcaaaat aattaatact ccaaagcagc  72720
atatttgggg tgacgtgttt ttaattcctt catttcccct gctgcagact ttcctagaag  72780
tttcagatat taaaagctga gttggtggct atggagataa gagccagatt cataacgagg  72840
gatctacaaa tggggagaag aacatagata agaataggaa tgaataagct gaaaggaaca  72900
ggtctgagca catttcccct tatcctgtta aacacacatc ccattgctgg gacaaggtca  72960
gtacagcaga aggaatgcac ctcttttgtt tgatggagag tgtttagctt gttctttaac  73020
aggtgcagct taggcactat ttgtcccagt ggatttacac agaccagcct tatccaccaa  73080
tgatcacaca aactcctcct tttgaggctg tcagtgtgtc cagggtgcaa caattttgga  73140
atacagcaga agctaagcta ttaacttctt ttgttgtggt tgctgttgtt gttttgagac  73200
agaatctcac tttgttgagt gcaggctgga gtgcagtggt gcgatcatgg cttgctgcat  73260
ccccagcctc ctgggctcaa gtgatcctcc cacctcagcc cccagagtag ctggaactac  73320
tactatgccc tactaatttt taaacttttt gtagagacag tctcactatg ctgcccaggc  73380
tggcctcgaa cttctgggct caagtgatcc tccctcctca gactttcaaa gtgctgggat  73440
tagaggcctc agccaccatg cccagattgc tttgacatct tgaggcctta ctgatccagg  73500
agagactgcc cctccctggg ccagctaatt cctacagaga ataaatgatt tgcttatggt  73560
gtgccttcga tgggccaatc aaccgattcg tatctccaac ataactttac cagccacctt  73620
tcagcaggtt cctgccccaa atcactccag ggacaggtac caggtaacaa aggaccactc  73680
ctataaccca gagcccatca caattattaa aactagccag tcctaagtct gtttaccctg  73740
tcttgccttc ttgcaaaaaa cacagtaaag cctttgtcc acctttgcc ctcactcatt  73800 ctgccacctg actgaccctg gtgcttcccc atggccctgc atggtgtggc atgtcccccc  73860
tattgtcttg ggaactgtga gtaacaaact ttcttttaca tggctatcac ctctgatctg  73920
tggcctcgcc atacctgaat aaagccaaaa tcccaggtac attttaaaac aagtctacaa  73980
gtcaaggaat accaaggatt tccagcaaca ccagagaggc cggcccacgc ccggcctgac  74040
tcttactgtt aatcactagt tttgcatttc tcttgaggaa ctagtcagga ggagaaaacc  74100
tagacagcag ctctcctggt caagacccag tcattcagaa gcctaaatgg catgcctagg  74160
tgcttggctt taaactgtta gcaggtatgg agtgctctga ttgtgttttta gaataatatt  74220 ctgggctggg cacggtggct cacgcctgta atcccagcac tttgggaggc ggaggcaggc  74280
ggatcacgag gtcaggagat tgagaccatc ctggctaaga tggtgaaacc ccgtctctac  74340
```

-continued

```
taaaaataga aaaaattagc cgggcgtggt ggtgggcgcc tgtcgtccca gctactcggg    74400
aggctgaggc aggagaatgg cgtaaaccca ggagtcggag cttgcagtga gccgagattg    74460
cgccactcat tccagcctgg gcaacagagc gagactccat ctcaaaaaaa aaaaaaaaaa    74520
aaaaaagaat aatattctgg ctgctgctgg aaggcagcca gggaggaagc aaggacattg    74580
gatactgcag taatcctggc caaaggcgac ttgtgaaaag gggtgggcaa ctgaaggggc    74640
aggagaatgt ggcccctctc agtctggaga gagctgcagc actaggccag gaaggcactc    74700
ttctgcgggg ggataggtct taaatgggga ccatgggatt gggtgcagtg gctcatgcct    74760
gtaatctcaa cacttcagga gtctgaggca ggaagaccac ttgagcccag gagttggaga    74820
ccagcctggg caacatagtg agaccctgtc tcaaaaaaaa aaaaaagac aatttaaaaa    74880 ctagccagat gtgatgcctg tggtcccagc tacttgggag gctgaggtga gatgatcact    74940
tgatcacttg agccctggag gtcaaggcta cactgagcca tgatcatccc actgcactcc    75000
agcctgcgca acaaagtgag actcttatct caaaaaggc gacaggtggg aaccatgggg    75060
aaccagagaa gcaaagctat tctcaagttt tccagtaacc atcctcttgc caatggtctt    75120
tctctgaatc ttggatttgg aataggatt ttcctgcctt gggaggctcc cttgggaaat    75180
gggagtgtca cagccacagg catcaaaagc cctagagttg cacttgaata gtgggtagaa    75240
agttctgtgc aatgccaggc actgttggaa acctctgggt agggcttaca gggccttagc    75300
catctgtggg aggcattagc tggagtgtaa taaatatgac cctcaggact ggggagaaac    75360
agctcattcc ttcatgaggt gtggggctgg cagccttgca ggcagccagc cacccttccc    75420
ctctggcctc catcctgggc actgagccag gcactgggta agaaggctgc tgcacctcct    75480
ttctcctctt cccttttaga gagaaagata cccccagccg aggatcccag aaaggcgaga    75540
gcagacgcgc cattgattgg cccaaagttc tccggagcca acctttgagc aaggagggcg    75600
tggctgggct ccagtctcct agtgaggtgc accactgcag gcttggtgac ccagccgttc    75660
ctgcccgctg cccccaacca gccgttcctg cccacagttc ctgttcccgg gcctgtcccc    75720
gggtttgtcc ccagggcccg tcccctgggt ttaggtctac cctccctcgc cccacccat    75780 cgccctcgcc atgggtctgg agctgtacct ggacctgctg tcccagccct gccgttcagt    75840
ctacatcttc accaagaacg gcatcccctt cgagcttcgc aaagtggagc tgaccaaagc    75900
tgggctgggc aggcaggccc agggatatt ggctgcggat ccccacctgt ccccactgct    75960
ttgcagtcgg gccgagaatg cagactaaca tgaagaatca gactctctgg tgtggaaact    76020
attacgtaat tatctatgtt attatttta cttttggag acaggagcta actctgtcac    76080
tcaggctgga gtgcagtggc acaatcatgg ctcactgcag cctcgacctt ccaggctcaa    76140
gcgatcctcc catctcagcc cctcaagtag ctgggactac agatgcccac cgatatgccc    76200
ggccaattta ttattattat tattattatt attactattg agaggaggtc ttcctgtgtt    76260
gcccaggcag gtctcaaact cctgagctca ggcgatcctc tttccttggc ctcccaaagt    76320
gctgggatta caggcatcag ctgtcatgcc ctgctggttg tttattttaa aagaggcttc    76380
atctttgctt agtgaataca aagcattctt caaaatacag gttaagaggg ggcagagcag    76440
atgcagcagg agggcaggga aatggagtgg ggctagaata tcttcacccc atgtgcttgg    76500
aaaaaacaat gaaactacct ccttgttttcc taagtggagt agtccttgtt tacctctgcc    76560
tgggtctctt cccttcttgc ctcttctttt tttgacacgg tctcactctg cagcccaggt    76620
agagggcagt ggcatgatcc cggctcactg cagccttgac ctctcaggct caagtgatcc    76680
```

-continued

| | | | | | |
|---|---|---|---|---|---|
| tcccacttcc | tcctctcaag | tagagtagtt | gggaccacag | gcacgcaacc | acatccagca | 76740 |
| atttcttttt | tttccttttt | tttttttttt | ttggtatttg | tggagacggg | attttgccat | 76800 |
| gtagaccagg | ctgaccttga | actccagagc | tcaagtgatc | ctcctgcctc | ctccttctaa | 76860 |
| agtgttgaga | ttacagacat | gcactaccat | gtctggccct | gggtctcttc | cacttttatg | 76920 |
| tatttcttgg | cattcttctg | cctttctctt | tcctgcatct | gacttgctct | atcccatggg | 76980 |
| gcttctcacc | cagctgaagg | ggctgctcct | agaggctaga | ggctggaggg | ccctgtggca | 77040 |
| gggcagtggg | ggaggccagc | accctcaccc | tgagctccag | cgtttgctgg | tctggctggc | 77100 |
| atacagagat | gcagctggag | cacaattcag | tggaggaggc | agggctataa | ctaagcagta | 77160 |
| gggcagagag | cagagccaga | gcccctggg | caggccagaa | ggaggaacct | gctcagctga | 77220 |
| ctcttcccaa | ctgctgccct | tggtacaacc | agcttgagtc | acctgctaca | gaacaggggc | 77280 |
| tggacacaga | agcagtctgt | ggagggagaa | tgggcagggg | tgtgcatgtc | cattcagtag | 77340 |
| aaggccagag | aggcccacat | gtaggcctat | gatcagactg | gagcctggct | tgactgatgc | 77400 |
| cctctgatcc | aaacaccagg | cacctaatgc | ggcctctagc | actggcctag | agtgctaaag | 77460 |
| tgagtcagac | ctgggaaccc | ccagtgggga | gggagccttg | agagtttggc | acaagaaagg | 77520 |
| aagaagagct | gagccaccgg | gggctgagtg | gctgaatggg | gcagggattc | ccagcaagaa | 77580 |
| tgaggttggt | ctgagggttg | ggaacatgtt | tggctgggac | tctggggtat | tgacaggtca | 77640 |
| cccagcctgg | ccagtagggc | ctaaggcccc | agctgggata | ggaagctgaa | tcagaggggg | 77700 |
| caagcctaga | gcccagggag | gaggctggag | gggtctgacc | tatggatgga | actggctggg | 77760 |
| ggtggggtgt | gaattacagc | tccagggaat | tgtccttgag | ccatgcttca | aggaactgga | 77820 |
| cacaggaaag | gtggccctct | gatagggtca | gggtctgtga | cccagtgact | aacagagagg | 77880 |
| cttcctcttc | cctgatgcct | cccagatagg | ggcctcagaa | agctgctgct | gggagtttgg | 77940 |
| agtggggtg | ggcagagaca | tcagagaact | cagggttctc | cccactcacc | tctctgatct | 78000 |
| cgcctgcagg | ccagcagcac | agtgatgcct | ttgcccaggt | gaatgccctg | aggaaggtgc | 78060 |
| caggccttga | aggatgggga | cttcaccttg | gctgagaggt | aaccggtccc | tgggctgctg | 78120 |
| ccgggccttg | tggggccagt | cagtcagctg | tctgtttact | gctgatggct | tggatcatgg | 78180 |
| actgtgggcc | ctgcaccagc | cccagggtga | agaatgggtg | gaggcaggca | gaggtgccca | 78240 |
| gtgttgacaa | gggctataga | agtcccctcc | tgcattgtac | aagtgaggaa | actgaggctg | 78300 |
| gaggagggga | gggacttgca | caaggccaca | gggcccagtc | tgcttccggg | cctcctcacc | 78360 |
| gccagtcttc | ccctccgaaa | aaaagagagt | gctaagtttc | gaggagcggc | tgtaccaggc | 78420 |
| atcttagtgc | taccattttg | cccacaaatc | ctgtggggca | agtgctgttt | ccctggagag | 78480 |
| tcgagggacc | actcagcgag | cttcagtggc | tatttgctaa | acatccacca | gggccagacc | 78540 |
| ccatttaagc | cctggggctt | gagcagtgaa | cgtgtctacg | tccttctcct | catggagctc | 78600 |
| acattccatt | aatagaaggg | ggagctgaca | gtaacccatg | taaacatgga | acatatcgga | 78660 |
| tgttgatgga | tgccatggaa | aaaataaaca | gggtaagagt | ggggtgtgt | gtcattatga | 78720 |
| gtaggatgtt | gagggaagac | tccctggagg | aggtggcatc | tgagcagaga | gctgtaggaa | 78780 |
| tgtgcaaggc | atgaggggaa | gggtgttctc | actggaggga | agagtgaggg | cgaaggctcc | 78840 |
| aggtgggaca | atgcatgggg | ttcagactgg | agagcaacgg | gccagggtgg | gtgcagtgag | 78900 |
| caggaagagc | aggaggtcat | gacagagggg | agcatgggac | actgggaagg | ctttggctct | 78960 |
| taccacaggt | agattgagtc | gctggagggt | tttgagcaga | ggagaactgt | gatctgactt | 79020 |
| acgtcataaa | ggatcccccct | ggcagggtg | agaaagccac | tgcagtcatc | tggcatgcag | 79080 |

```
cgctggagcc ccagaccaag gtggtggtgg tgcaggggttg gtggggattg tggtcagttc    79140
tgacttttat tgaaatctaa ctgcagggtt tgctgaaggg ttggaggtgg gtgggaaaaa    79200
tgaaagccaa aaccagcctc taggttggtg gctgcatggt ggcgtccttt accgaggcca    79260
aatagtgcct ccttggtgga gctggattca cattcagagc ctgggatcac tggatggtcc    79320
aacacccata gaggcatgat gagctctggg ggtcagactg cacaacccct caccataggt    79380
gaacaggaga tgggacaggg tggggagcaa tgctgccatg tcacctggaa ggctctctcc    79440
ctgctggcct tgctcctggc cctgtccacg ctttggatat gttggggaga tatccaacat    79500
gctctcgttc ttcagactca cagtggatgc cccttcctcc tggaagcctt ccctgagccc    79560
ctgctgaagt tcatgacatt ttgtttctta cttgctgccc ttagttgaga tgatagtctg    79620
gccccgtgta gggctgtgtg accctgggca cttacctaac ctctctgagc ctcacatccc    79680
tcctctgcat catggggata gtgaaaatgc cccagaaaat ggctgaagag tgttcagggc    79740
atgttttctg cccctgccat gtccccccag tgtggctagc ttgctgtgta tgaactgcat    79800
gtacaaagca cctgaccact ggtacccccca ggacctgcag gcccgcgccc gtggggatga    79860
gtacctgtca tggcagcaca tggccctgca gagtagctgc tgctgggcca tgtggcagaa    79920
ggcgagccat ggagggcagg gacatctccc aagatgccaa gggatgctgc tttcacttta    79980
caaaatcctg tttagacctg agaccaaatc ctggaatgcc agagactgcc taattcaccc    80040
aacttgtttc ctaggaggga aaccaaggac cagagccaag gaaggattcc cctaatatgc    80100
cttaattcca gagctatgag cagttaatcc tatgctcttt tgcatactcc aggttgcctg    80160
ggaatcttgc ctttagggg agaaaataaa caaaccctca ctttgctaca cataattc      80220
gtagatggag aagtatgaag tgaaaaagt caaactagga agaagtgagg agacatttca    80280
ataaacgttt gtctgatgtc tcggtatgaa aggactttct aaccctcaga acagtgggag    80340
aactcaacaa agaaataacc actacatgcc agctgcggta gcatctgtaa tgagcacacc    80400
tgtaatccca gcactttggg aggccgaggc aggcagatca cctgagattg ggagtttgag    80460
accagcgtga ccaacatgga gaaacccccgt ctctaccaaa aatgcaaaat tagccgggta    80520
tggtggcgca tgcctgtaat cccagctact cgggaggctg agtcaggaga attgcttgaa    80580
tctgggaggc agagattgca gtcagctgag atcacgccat tgaactccag ccttggcaac    80640
aagagcaaaa ctctgtctca aaaaacaaac aaacaaaaaa acatatacaa ggacatgttg    80700
tgtaagaaaa aatggattaa acataaaaca agcaaaaaac cgggaaggat cttgataaaa    80760
gatatgtcag aaggaggtaa tgttctttaa gatgctctta gaaaccctta agagaggcct    80820
ggtatggtgg ctcacccctg taatcccagc attttgggag gccaaggtgg gcagatcact    80880
tgaggtcagg agtttgagac caccctgggc aacatgatga acccccatct atattaaaaa    80940
tacaaaaatt agttgggtgc ggtggcacac tcaggagact gagacaggag aatcacttga    81000
acctgggagg cggaggttgc agtgagctga catcatacca ctgcactcaa gctccactta    81060
gagcgagact gtctcaaaag caaacaaaga aaataagag aaacccatca gacaagagac    81120
aggaaaaaaa tgagtcatag ctcactgcat tctagatctc ctgggctcaa gcgatcctcc    81180
tgcctccgcc caggtagcta gaactacagg tgcacaccac aacactggga ttcttttttt    81240
ttttctttt ttttgtagaa aacaacgaag ggaatcttgc tatgttgcct agcctggtct    81300
tgaactcctg ggtcaagca atcctccctt cttggcctcc caaagagctg agattacagg    81360
tgtcagccac tttgcgtgac cacaatttca atcatattta aaatgtacaa ttcaagtgat    81420
```

-continued

```
tttgccacac taaccacaga ctcatgttta agccacacca acggatttcc atgttttaaa    81480
taacatattt tgccaccccc tagtggacag tggctcacca ccggcacaag gggctacata    81540
ggcagtcaat gggaaccagg cggggacggg aaatgtcgtg aacccaacgg tccctgccca    81600
gccccacccg cgtccgcaac gtgtaaccac atctcctgac tgcccaagag aagcgcagat    81660
ttccatactg aacatgaaat tgcctgactt cgaaatggtg gcaaatcatt aaaaaaaatt    81720
ttaaactcac tttgcattgg ttattagggt cgaacttggg gaagacccct acaggtgtgt    81780
gtgtgtctgt atgttagggg tgttcagacc tttaataggg ctagaaacca ggcaaccaca    81840
ccgcggaaag cttgaggaga gggaaatcca ccagacgcca agcaggaggg tcagggaaga    81900
gacagggtgg ggccactacc gggttaaaga cttgtagtgg gtggggctac acgtagggcc    81960
gagacgaccg gatttccgga aatcagagcc ggcacacgtg acttttgttt gcagaagtgg    82020
gaaggtaccc taggcagcca atcggggagc gctgagtctc tgtccagcca atgagaagcc    82080
aggttgtttt agcgcctcgc ccctcctctc cggtccgcga gccttgggta tctccagctt    82140
ttttccgcca gagctgtttc cgttcctctg cccgccatgc cgttcctaga gctgcacacg    82200
aatttccccg ccaaccgagt gcccgcgggg ctggagaaac ggctgtgcgc cgtcgctgcc    82260
tccatcttgg gcaaacctgc agacgtgagc gtgggccggg cagcactggg cgaggggaag    82320
ttggtgggcc agggtccgg ccttgtccct gctctgcctc cgcaacagcg accccgatcc    82380
cttcccccag ggaccacccc ccaccccatt ccgcaggcca agctctgact ttccgtgctt    82440
cacgatcccg cggctccccc tccgcacgtc tttcccttgt cgccctcccc agtcatgacc    82500
cggacgtgac cttcagggac ctcggcctgt actgggatcc ctgtccccgc gaacactgcg    82560
cgtttcggct ttcgcgcgct cgggtcggga ccccagacgt agcccgactg gctccagctt    82620
cgggtaaaac ttttcatgtt cccctcagct tgtgaacgtg acgtacggc cgggcctggc    82680
cagggcgctg agcgggtcca ccgagccctg cgcgcagctg tccatctcct ccatcggcgt    82740
agtgggcacc gccgaggaca accgcagcca cagtgcccac ttctttgagt ttctcaccaa    82800
ggagctagcc ctgggccagg accggtgcgc aggggtagta ggcccggaat attattctaa    82860
aacacaatca gagtactcca ttcctgctaa cagtttaaag ccaaacacct aggcaggcca    82920
tttaggcttc tgaatgactg ggtcttgacc aggagagctg ctgtctaggt tttctcttcc    82980
tgaccagttc ctcaagagaa atgcaaaact agtgattaac agtaagagtc aggcagggcg    83040
cggtggctca cgcctgtaat cccagcactt tgggaggccg aggcgggcgg attatgaggt    83100
caggagatcg agaccatcct gactaacacg gtgaaactcc gtctctacta aaaatacaaa    83160
aaactagccg gacgtggtgg gcgcctgtag tccccgctac tcgggaggct gaggcaggag    83220
aatggcgtga acccgggagg cggagcttgc agtgagccga aattgcgcta ctgcacacca    83280
gccggggcga caaagcgaga ctgtctcaaa aaataccaa aaaacaagca aaagaaaaca    83340
aaacaaaaac agtaagagtc gtcccaacgc agtggcttat gcctgtaatt ccagcacttt    83400
gggaggccga ggcaggcaga tcacctgtgg ttgggagttc gagaccagcc tgaccaacat    83460
ggagaaaccc tgtctctact acaaatacaa aattagctgg gcgtggtggt gcatgcctgt    83520
aatcccagct actcagaagg ctgaggcagg agaatcactt taacccggga ggcggaggtt    83580
gtggtgagct gagattttgc cactgaactc cagcctgggc aaaagagca aaactccttc    83640
tcaaaaaaac aaacaaacaa acaaaaaaaa aaacacaca cacacacaat ccaaaaacca    83700
gtaagggtca tgtcctggga ggctaactca gccgactgtt aggtcaccat gcttatagcc    83760
aagaaatgtg ggatgctgct gggccctgag cggtcagata aactactttc tctgataatt    83820
```

```
agaaggctac aggaaatgtt ttgttttgtt ttgttttggg tttctttgtg tgtttttaga   83880
gacaggatct tgttctgttg ccccaggctg gagtgctatg gctcaatcag agctcactgc   83940
agcctcgaac tcctgggctc aagcaatcct cccacctcag cctcccaagt agctagaact   84000
acaggtatgc atcaccacgc ctgactaatt aaaaaaaaaa tttctttttgg ttgcgtgtgg   84060 tgtcttggca cccgtaatcc cagcactttg ggaggtagag gtgggagcat ctcttgagca   84120
caggagtgca gggctagcct gggcaacatg gcaagaccct gtctctacaa aaataaaaaa   84180
gaaatgagct gggcgtggtg gggtgcacct gttgtcccag cttcttagga ggctgaggtg   84240
ggaatattgc ttgagcctgg gatgtcaagg ctgcagtgag ccatgactgt gccactgcac   84300
tccaggctgg gcaacagagt gagacccat ctctgaaaaa atatttttt ggggagccaa    84360 gcacagtggc tcatggtaat cccagcactt tcagaggtgg aggtgcacag atcatttgag   84420
gtacagagtt tgacaccagc ctggacaaca cggtgaaacc ctgtttctac taaaaacaca   84480
aaaattagcc aggtgtgata gtgcgtgcct ataatcccag cttctgggga gactgaggca   84540
agagaatcgc ttgaacctgg gaggtggagg ttgcagtgag ctgtgatcat gccattgcac   84600
tccagcctgg gcaacagagc aagacactat ctcaaaaaaa aaaaaaaaa agtttgtttt    84660 gaaatcctgg actcaagcaa tccccccaac ctggacctcc caaagtacta ggattataag   84720
tatgagctac cacactcagc cacttttttt tttttttgaga tggagtctcg ctcggttgcc   84780
caggctggag tgcagtggcg cgatctcggc tcattgcaag gtccgcctcc tgggttcatg   84840
ccattctcct gcctcagcct cccgagtagc tgggactaca ggcacccacc accacgcccg   84900
gctaattttt tgtatttta gtagagacgg ggtttcaccg tgttagccag gatggtctcg    84960
atctcctgac ctcgtgatcc ccctgccccg gcctcccaaa gtgctgggat tacaagcgtg   85020
agccaccgca cgcggcctca gccacattta ttaatttcac tcttggcaaa catcaggggg   85080
aagctgaccc acacggcctg ggaagggggt tgtcttttgc atagagacca tgaccaggtc   85140
tgggacagag gaaagtcaaa taaatcacac attagagtta gaagcagagg ctcaggctga   85200
gcccaggttt attatccaaa atcaaaatga aatgcagtga ttaaaggaca caaggcctca   85260
gtgtgcatca ttctcattgt ggctttcagg cggctgtgga agacagggtg gggatggtgg   85320
cttcgggagg tgaggtgctc tgggacttgg gcaagtctta ggcaagccat tcctgctttc   85380
tgggcctggc tcccatgggc cattagaaat gaaaatgctt tgtggactgc tgaggacggt   85440
gcaagggtga ggtttcccag ctcaccggat catggccagc acccagggca tcagcttctg   85500
ctttatggtg gggtctgcag gtgggaagtc cttggccttc agaatgacct catgggcctc   85560
ctggaagagg tcctccccca ctgctgcctc cacgcgctgc cgccatgtgg ccagcttggg   85620
tcggccttcg aagacttggc agccagcacc cacgggctgt ggggaaaagg gtacagactg   85680
gggatggatg gttgtgaggg cagggatggg cagcatctga tttggggacc acagatctcc   85740
aggaggtgtt tgcacacaca cttaagcaca gtgccatagc ccggtgtggc agcataagca   85800
ggacttcagc aactagccag gccccctgc ctagtgggtt cacctgccca cagcactcac    85860
atgcatcagc tccgtgatgg ctacgaggtc agctaaggag atgtgaggac cagtaaggaa   85920
ggccttgttc tggaggaact tgtcctcgag caactgcagg gtcacatcca actctgccag   85980
ggtggctgcc agtgtctggg gagatactgg ctcacccagg aaaacaggga acatcacctg   86040
gggattgggc aggcaaagtc gggagttact ggagtaggga gttagttttg atttgcattt   86100
ccctaatgat tagtgatgct gagcatcttt tctttttttt ttttttttga gactgagtct   86160
```

-continued

```
tgctctctcg cccaggctgg agtgcagtgg ggtgatctcg gctcactgca agctccgcct    86220
cctgggttca cgccattctc ctgcctcagc ctcccgagta gctgggacta caggtgcccg    86280
ccaccacgcc cagctaattt ttttttttatt tttagtagag acagggtttc actgtgttag    86340
ccaggatggt ctcaatctcc tgaccttgtg atctgcctgc ctccgcctcc caaagtgctg    86400
ggattacagg cgtgagccac cgcgcccggc caagcatctt tcttgtact tgttggccaa     86460 aatgataata ttctcaacac attgggttaa gtaaaatata tcaatttcct tttacttttt    86520
tttttctttt tgagacagtg ttcagctctg tcacccaggc tggagtgaag tggcaccatc    86580
tcggcacact gccaactttg cccctgggt tcaagcaatt ctcctgcctc agcatcctga     86640
gtagctggga ttataggcac aggccaccaa gcctggctaa tttttgtggt tttagtagag    86700
acaaggtttc cccatgttga ccaggctggt ctcgaactcc tgacctcagg tgatccactg    86760
ccttggcctc ccaaagtgct aggattattg catgagcca ctgtgcctgg actcttttta     86820 cttttaaat gtgcctacta gaaaatttaa aattacgtat gtggctcact ttatacttct     86880
atcggacagc acttgactaa atgaactaaa ttccagagag gcataagccg ttcctagatg    86940
agctactttc attccaattt catttccttg ggcccaagca ggctgggaga aagactgtca    87000
caggcatggg cttttctgac tgagcagcag tttgggaact gggggcaggg atgaaaagca    87060
gagagatctt acaggcaaca tcgtagttgg tgattagatt ccaaagccat gctagactga    87120
gctagtgacc tgatctcaca ttcaagatat ttgaaaccaa agataaactg aaaccaacta    87180
aacctgcaac ccagcccacc tcctgattag cttagaagag aacagcctca catcctggct    87240
acctgacaca gggaagtgca agccctttct tggggtgtt tattatgcaa ttcaatctct     87300
gctcttcttt tatcataatg tctggcacac aaggatacat catgaggccg gcatggtgg     87360 ctcatgccta caatcccagc actttgggag gccgagatgg gaggatcacc tgaggtcagg    87420
agttcaagac cagcctggcc aacatggtga accctgtct ctacaaaat acaaaaatta      87480 gccaggcatg atggcaggtg cctgtaattc tagctacttg ggaggctgag gtgggagaat    87540
cgcttgaacc caggaggcgg aggttgcagt gagccaagat cgtgccattg cacgccagcc    87600
tgggcaatgg agtgagagtc cgtctcaaaa aaataaaaaa taatgataat acatcatgag    87660
acatgcaaag aagcaggcaa atgtgaccca taatcaagag ggagaaaaca acaatcaata    87720
gaaatagacc cgtaggctgg gtatggtggc tcatgcctgt aatcccaaca ctttgggaag    87780
ccaaggagga cgaatcactt caggtggaga gttcgaaacc agcctggcca acatggtgaa    87840
acccggtctc cactacaaat aacaaaagtt agccaggtgt gctggtgggt gcctgtaatc    87900
ccagctacgc aggaggctga ggcaggagaa tcgcttgagc ctgggaggtg gaggttgcag    87960
tgagctgaga tcgcaccatt gcactcagcc tgggtgacag agtgagaccc catctcaaaa    88020
acaaaacaaa acaaaaaaac cagacccaca gaacacctac gtgttgaaat tagttgcaaa    88080 agattttag gtaacagtga taaatatgtt aaagaattta caagaaaaga cagataaaat    88140
ggatgaacag atggtgaatt tcatcagaga agtggaaatt ctaaaaaaca accaaatgga    88200
atttccagag ctgaaaaata catatctcaa acaaagaatg tattggatgg gcttaatagc    88260
aatttggcac aacagaggaa agaatctgtg aaggcaaaga caggtcagta gaaataatcc    88320
aaaactgaaa agaagagact ggtgcctgaa cacctttggg gaatgctctc gctgccgccc    88380
cccacattcc cagcctcacc ttatgccaca aggcccggag gcagcttctc cgcagagtcg    88440
tgtgctgcca tgccaggtac tcatccacac gggcacgggc ctgcaggtcc tgagggtacc    88500
agtagtcagg gaccttatat ttgcgcgtca ggtagagcag gatggccaca ctgtgggtgt    88560
```

```
gggggtcatg atgggtaagg gaagggcact gtgctgggta tttcatacat agtcgctttt   88620 ttttttttt gatacggagt ctcgctctgt cgctcaggct ggagtgcagt ggtgcgatct    88680
tggctcactg caacctccac ctcccgggtt caagtgattc tcctgcctca gcctcccaag   88740
tagctggaac tacaggtgcg tgccaccatg cctggctaat tttttgtagt tttagtagag   88800
atggggtttc accatattag ccaggatggt ctcgaactcc tgaccttgtg atctgcctgc   88860
ctcggcctcc caaagtgctg tgattacacg tataagcaac cgcacctggc ctttttttt    88920 ttttttttt ttttttttt tggagacaag gtcttcctca gtcacccagg ctggagtgca    88980
gtggtgcagt ctcagctcac tgcagcttca atttttatag gagtgcacca ccatgcctgg   89040 ctacctttt tctttttgt agagatggga tctcactgta ttgccaggct ggtcttaaac    89100
tcctatcctc aagcaatcct ccagccttgg catcccaaag cgctggcatt ataggcatga   89160
accactgtgc ccagcacact tctttaacct ttctgacaat ttgccaaagt attagcctca   89220
ttttccagag aagaaaacca ggcttagaaa ggcagagact tgccctaggg cacacagctc   89280
ttaatggcag agctgagaat ctttctgagg ctaatacccca agcttttcct accaccaggc   89340
aaaatcccac aacagaatgt cttgccaaat gtttagagac agtttctgat cagagaacca   89400
gagagagctt ccaggagaac ggggcatcaa agctgagctt taaagaagct cagttctttc   89460
cattcggtat ccactctcat ctgctgggat tccgaccagc ctctgatggc ctgactgttc   89520
aaaaaggctt ccgtgtccct ttgttctttc tgtcattctt tctgccaaga atcagctcct   89580
atctaagctg actggggtag tttggcttcc taaagtacca ctcaggaagc actcctgcag   89640
ctgcaggatc ctagaacaac agaacagaca aggcccctg gcactctcct ccttccctgg    89700
gttttgaggg ccgccatggt gatgagatga gcatggacct ggaaggacac aggatgtgtc   89760
catttggaga cacagaaaag ctttcaggaa cttggggttt cccaaaggtt gggcatgcag   89820
gccaaaaggg cagaaaacct ctgtatctgc cacgggccta tattctcttt taagctgggg   89880
ctacacacgt gtcccagctt aacgactccg ttgtctgtgc agggtgccca ggagctcctt   89940
ttgctcccag ccaattgttc aagccacctc tgaggagggc tgcaggtctc tgtgagccac   90000
agacctgaag gtgagagtag tgacagaggc agagattgca cattgactct ggctggtacc   90060
tgggggtcac aacgctgagt gacacaagga ctcaggacac ctggggcacc agggaggaag   90120
acgggccctg gcagaatgtc agaggaattc atcggaggtg cgtccatcct gagatttcag   90180
agatgagctt taaagcacaa actccaggtt cttgttaggg gaagggtgac tctggtgaca   90240 aaagggggcag aactggggaa agattggctt ttcctgaaga ggattcaact tcttgggacc   90300
agctgtgatg taagacgtcc atatctggtg gctcttccat ggggaagacc catcctggga   90360
agctgcagcc cagagatgga gccaccgggc agcccagatg ccactgagcc atcgccacac   90420
aagcttggcc agaggcctgc cccacggtgg gcaaagctgc catcgtcctc tggcctaccc   90480
tgtctcaagg atactctcac cactcaccag caaccaaagc actggtgtgg aagtaaagta   90540
gatatttgct tttctaatca tcagggtgaa ctggaataga aggaaggcaa gggcctgggg   90600
tccagtactg actctctgca ggatgcgggg cacagagact ctctgcctct gaagacttta   90660
gtttccttgt ctatgaaata gagggttaga acaggatggt tccagcaggc ctggcagcag   90720
tcctagggtc ccagttacct ctccgtcaag gtgaagtccc cgtccttcaa ggctggcacc   90780
ttcttgaggg ggttcacctg gcaaaggca tcgcttaagt gctgacctgg gaagagtcca    90840
gcatggtggg tggtgggagg agaacgctga gcccgccatg gcctgtgccc ctccctgcaa   90900
```

-continued

```
tgctctggcc ccagtttcac agttcttctt cccaccagtc tgcactcctg gttggcaaag   90960
actggaaggg cccctgcggg aggaggagga gaccactcca ccggctggta caaaatagac   91020
aacacccctt gctaagtcct gtaggcacag cctcctccca caggctgccc ctctgcaaca   91080
gagctcactg tgcagggtgt ggttcctgga cctttgcatg caccctaccc atctcctctt   91140
tccactattg ccagcttcat gaactcacaa tcagagcacc ccaagctgca cgataggtca   91200
cctgagggga ctgactacct tgtcccttcc accattaatt ctaaggcagg gtcatgaaac   91260
acagagaagt ggtctttttc tggtatctac ctacttagaa gcaacttcta ctggccccac   91320
catgtccctt tgttcaccct gccctgggca ctgtggagct gtgtgtagca tacctgctac   91380
caccccctgt gccccaaact tttattcccc ttacagttgg ggtctcacta tgttgcccag   91440
gctggtcttg aactactggc tcaagtaatc cttcctactt cggcctccca agtgctggg    91500 attacaggtg tgagccacca tgcccagcct gctaccctct cttcaccctc ccttcagact   91560
gttccttcac caggaaaacc ctcctctgtc tcctgggaaa acacacttcc ctctgcacca   91620
ctacatttga caaccagctt ggacgtcctc ttgtccccca ttccctttcc tctactccac   91680
actctgcaga ggaagtcctt gcgcaggaca gtgggcagtt tgcagaagag attatgtgga   91740
gaagtttcag gcagagggcc agccatggag tgggagccct gggcagaagg cttagccaag   91800
tagagtcgcc ttacttgccc caccagccat acctggattc tgcttccaac ccctcctact   91860
accccaccct gcactgggcc tgggcctggg cctgccagct gagtcctcaa gggccttgga   91920
ggcatgctag agaaacaaaa cagggtgtag ggctcatcaa gccccagggt cccctgctg    91980 cttccagcat cagcagcctg gggcaaccta cctccccagc aggaacaaga ggcagaggac   92040
aaggtttcgg gcggcagagg ttgcagtgag ctgtgatcct gccactgcac tccagcctgg   92100
gcgacagagc gagactccgt ctcaaaaaca aacaaacaaa taaacaaaat gccttgggcc   92160
aggcacagtg gctcatgcct gtaatcccag cactttggga ggctaagccg gcagatcatt   92220
tgatgtcagg agttcgagaa cagcctgacc aaaattgtga aatcccatct ctgttaaaaa   92280
tacaaaaaaa ttagccagac atagtggcac acatttgtaa tctagctact caggaggctg   92340
aagcaggaga attgcttgaa cccgggaggt ggtggttgca gtgattcgag atccgtgcca   92400
ctgcactgca acaaagcaaa agcaagactc tgtctcaaaa aaaaaaggac aaggacaagg   92460
tcagaggcaa aacaggagga acagaggaag gaagggacaa agagggaccc caatgcagac   92520
tggacgagtg cagagggcag ggatggaaag tcacgtcctg agctgtttgc tgttgcagaa   92580
tctcagcagc tgggccataa agaagggact tgacgctgtc ccagtctcta cacttggcac   92640
ccttgacctc tctcatccca cctttcccta ggccgaggtc acacctgctt tcatttgtt    92700 ttttttgtt tttttttttt aagacgggt ctcgctagat tgccctgacg ggagtgcagt     92760
ggctattcaa gggcaccatg atagtgcact gcggcctgga attcctgggc tcaagcgatc   92820
ctcccacccc agcctctcga gttgctggga ctacaggcgt gtgcccctgc acccagctgc   92880
gcccgttttt gtcctcctgt ctggcttctc ttcatgatcc ccacccctt attcggcctc    92940 agggggaaccc cgtggtctat tccgtgagac cgagcagagt tttgggggagc cccgactctt  93000 ggatctccct gctggctcac cttctctgt tcggtctcca aaccagacca gcaatggccc    93060
caggaagaag gtggcgctgg gagaagttcc ctaagctatg tatgcctacc tgtccccttc   93120 ctgactttt ggttccccaa acccgaggct ggacctacct ttaatcagat ccacgatgcg    93180
cagctcgaag ggaatgtcgt tcttcttggc aaagatgtaa acagcgcggc agggctggga   93240
cagcaggtcc aggtacagct ccaggcccat agtggggacc gaccgacctg accggaaacc   93300
```

```
agagggagtc agcaaactcc agtgccagga ctcgggtctc ggacctcaga ccacgcccct   93360
gcggctacgc accccgaccg ctgtgcccca ttgggcggca cggacgcctg ggacactctt   93420
tagtccaatt gcgggcggcg gcggcctgt ctcagggctg ggcccgcctg gctcctgtgg    93480 gatcaggtg ggtggccaag agaccgttgt ctctcagggg gacgcacaga gaggccccag    93540
tcccatccct ttcgtgcctg gctcgctcat ttcacttagc ataatgtctt caaggtgcat   93600
ctgtgttgaa gcgtgtgtca gaatttccca ccgtccgcat tttagaggag gagacagaca   93660
ctgaatgatt atagacccag aaagtctggc tccaaagtcc atcctcttgg ctcaacactg   93720
cagagtcctt ggtgccagca agtggcaaag cctcagggct tacgttcagt gttttgtggt   93780
cactcgcttc actgcagtcg cactccctgg aatgtcacag ccttggtctt cctgcccctg   93840
ccagcacagt gccatctatc gcattccctg ggtttatttc ttcctttctc caggcctgtg   93900
tttctccatc tttaaaatga cagggaagct agagccctcc agagtccttg caagtccacc   93960
cccctggatt catctgctga gccgtaagcc caggcctgcc ccttgctgcc atggagcctg   94020
tcaaatagta tcagggtcac atgtcatttt ctaaaacgaa tcccactgaa agtgtgtcag   94080
ccaacgcata atgttttcta gagaataagg aacatttctg caaataaagt ggaagtaaca   94140
actgttttat tttatttaga tagagtctca ctctcttgcc cagggtagaa tgcagtggca   94200
tgatcacagc tcactacaga ctccaactcc tgggctcaag ccatcctccc atctcagcct   94260
ccccaagtag ctgggactac aggtgcgcac aaagacgccc agctagttaa aaaaaatttt   94320
tttctgtaga ggcagggtct cactatgttg cctaggctga tcctcccacc tctgccacct   94380
gctgggatta cagatgtgag ccactacaac tggccagtaa taatgatttt taactggaaa   94440
aaaaattaag gaaagatgag aaattcagat ttccatgtta aagttttgaa aggaggtaga   94500
cactcagaga aggcaatggc tgccttatcc tcacctctgg ataactccag tcagaggccc   94560
aaggaggagc tgtcaggatt ctggttcaag gctcagcctg tcttttaagt tcaaaaccta   94620
atttggggcg ggagtggtgg ctcattccta taaccccagc accttgggag gctgaggccg   94680
gcggatcacc tgagttcagg agtttgagac cagcctggcc aacttggtga accccatct    94740 ctgctaaaaa tataaaaatt atctgggcgt ggtggcatgc acctgtaatt ccagctactc   94800
aggaggctga ggcaggagaa tcgttgaact ctagaggcag aggttgccgt gtgccaagac   94860
tgcgccattg cactccaggc tgggcgacaa gagagtaact ccaactaaaa aacaaaacaa   94920
ctaatttggt ccacgtttca ggattgatca ttttctttgg gtctgactca cataaaccaa   94980
ctcacaaagg ctgtatttat taatttatag aaacaagata aaagtgagag tgtgtgggtt   95040
ggttcgtttg tttgttttt gactttgccc ctctctgtca ctcaggctga agtgcagtgg    95100
tgcaatctct gctcactgca acctctgcct cctgggttca agcgattctc gtgcctcagc   95160
cacccgggta gctgggattt caggcatgtg ccaccatgct cagctaattg tatttttagt   95220
agagacaggg tttcaccatg ttggccaggc tggtcttgaa ctcctggcct caagtgacct   95280
gccagcctcg gcctctcaaa gtgctgggat tacaggcgtg agccaccgtg cccggcctag   95340
aaagaagaga aaagtcattt agacagaatg ctcccaacca ttgctcagtg ctctcttggc   95400
agtgtagtct cctaggaagc ctcgtgggtg ttactggcca ggaccaggtc cgttctgccc   95460
atgcacagta aattaatcac tgtgacatga gttttgcaaa agactaaaga tttattcaca   95520
agggtgccaa gcaaggaggt aggataatag ctctcaaatc cacctccccg aaaataaggc   95580
ttagggataa gccttgcttc caagcaataa agcacagacc ccagtcacac tcaaggggag   95640
```

```
ggggctatac aaggatgtga ataccagtct gcctgcctcg tgggcctaca acgcagaagg    95700
gccatgcact tggtttaaaa ctttgttgtt gctgtcttga cattcttaac aatttaaaaa    95760
taagggtccc cacattttca tgtgtagcca gtcctgtcca aggagtccaa agaggtcatg    95820
agggtggaca ggtcactgtc tcctctgggc agtgatgggg ccactagcag ttgttctgta    95880
gtctcctagc ccctacccca gggccacacc ttccccatgg tctctcacat tcttttttt     95940 tttttttttt ttttttttga cagggtcc tgctgttgcc caggctggag tgagtgcagt     96000
gctgcaaact cagcttacta tagcctcgac ctcctgggct caaacaatcc ttctgcctca    96060
ccctcctgtg tagttcggat cacaggcaca tgccaccatg cttggctaat tttttgactt    96120
tgtagagagg gcatcacact ttgtttccca gggtggtctt gaattcctgg gctcaagtga    96180
tcctcccacc tcagcctccc aaagtgctag gattataaag atgtgatccg ccgccccggc    96240
ctctctcaca ttcttggcat ttaaagttac cgtcattgac aaggaacatg ggtacactcc    96300
aatttactca agaaaaaaac tcttttctcc attgaagaga tatgtggcct ggctgcttcc    96360
tactctagtt gaggtcttct ttttgtttcc tttttcttct tctctcttgt tttttagaga    96420
cgaggtcctg ctgcgttgcc caggctggtc tcaaagttct agcctcaaga gaccctcctg    96480
ccttgtcctc ccaaagtgtt gggattacag gtgtgagcca ctctgtccag cctcaaactg    96540
tggtcattag atcagcagca gcagcagcct tgcctggagg cttgttagaa atatactaac    96600
aggctcccac ccccaaaccc agacctactg aatcagacag agtctgtatt ttcataagat    96660
cctcagatga tccaaatgcg ccttaaactt tgaggagctt tgatccagaa cctgggctgg    96720
aggcccctgg gggccactct gttcctcaca gactgcaagg tatgtttttt tcttgcctct    96780
tctctctgtc ctaatgtctc cttctctctg tgtctgaccc tgaggaccct atgacatctt    96840
cccaggggag tttccactgt caaagagctg attctctctc tcttttttt tttttgaga    96900 cggagtttcg ctcttgttgc ccaggctgga gggcaatggc gtgatctcgg cttaccgcga    96960
cctctgcctc ccaggttgaa gcgattctcc tgcctcagcc tcccgagtag ctgggattac    97020
aggcatgcat caccacgccc agctaatttt ttgtagtttt agtagagaca gggtttctcc    97080
atgttggtca ggctggtctc gaactcctga actcaggtga tctgcccacc tcagcctccc    97140
aaaggcatga gccaccatgc cctactgcca gaggcctgat tctctagaat ctgatgggct    97200
cttctagaca gcaatctcta cctgggctct tgttgaagaa gccaatcagc tcattggttg    97260
gaggtcacat gatataaaac atggccatct tccaagccct atgtgtggac aacgagatag    97320
ggacaagtag gcatatcacg ttctgatacc tggacccaca tctgtcgctg gcccacgtc     97380 tgtcctcagg ccccaggat atacttttat ggggagtttt cctcccttcc cccaatgtgg     97440
tcactcataa ctttacaccc aacagtcaaa caggagtgga agctacagag tttcacgcaa    97500
acaataggct aggctgtggg actgagtaaa aggcactgga ctgtggtagg tcttactcca    97560
agatggccaa atggaagggc ttttagcttt ctttgttttt gttttatatc ctgagacaaa    97620
atgttcaatt tctacacttt agaataaaaa gagccatatt ttatgtttca tatttttgt     97680 atgcttcctt tcatactctt tgaacaatg caatcatatt ttcattatga ggtataattc     97740
acataccata atatccgctc tttcaaaata tactttaaaa ttcaattggt ttaaagccaa    97800
ttcattggtt tttagtatat taacaaagtt ttgtcaccat cacaattatc taattctaga    97860
tcattttcat caccctaaa agaaactctg tacccattaa acagtcactc cccatttccc     97920
tcttctccta gccctggta accattcatc tactttctac ctctgtggac agtaagtatc     97980
tgcctattct ggacatttca ttcaaattta ataatgaaat atgtgagctt ttatgactgg    98040
```

-continued

```
cttctttcat ttaacataat ggtgtcaagg ttcattcatg gtgtagcata taacagtact   98100
tcatcccttc ctgtggctga attatattcc attttatgta tacaccacat tctgtttatc   98160
cattcaccag ttgatggact tttgcattga ttctacttt cagctattgt gaatccccat    98220
gctgtgatga acattcacgt acaagttttt gtctggacat atgtcttcag ttgtcttggg   98280
tatacaccta ggaatggaat tgctggataa tataattcta tgttggccgg gcacggtggc   98340
acatgcctgt aatcccagca ctttggaagg ctgaggtggg tggatcacct gaggtcagga   98400
gttcgagacc agcctggcca acatggcgaa accccgtctc tactaaaaat acaaaaacta   98460
gctgggcatg gtggtgcctg cctgtaattc cagcctgtaa ttccagttac tcaggaggct   98520
gaggcaggag aattgcttga aaccaggaga cggaggttgc agtgagccga gatggcacca   98580
ctgcactcta gcgtgggtga cagagcaaga atctgtctcc aaaaaaaaaa aaaacaaaaa   98640
aaacaaaaca aaactaaccc atatatat aatatgttat atacataa taatatattt      98700 tatatatatg tgtatatatg tttaacttt ggaggaactg caagctgttt tccaaagcgg    98760
ttatacattt tacattctca gcagcagcac acaagggttt caatttcttc acacatcctc   98820
aacaatactt ttaatctgtc ttttctgtta taccctcat agagtgtgtg aagtgatatc    98880
tcattgtggt ttgattggca atgtcttgat tatagtatct ttgtactaag ttttgaaatt   98940
gggaagcatg agtcctacag ctttttcttt ttcaaaatta ttttgaagat tctgagtcac   99000
tttaatttcc aaatgaattt tagggccaat ttgtcagttt gtgcaaacag gccaagtgga   99060
attttaatgc agactgtgtt gaatttgaca tcttaacatt actacacctt ccaatcatga   99120
acatgggatg tctttccatt tattaaggtc ttctttaagt tttcccccaa cttttaaatt   99180
atgaaaacat ttaaaatcca gaaatgaaa ggactagtac aacagcacta atatatgcaa    99240
ccccagtttc aacttactgt ttttgaaca taagatacca acatcatgac accccaccta    99300
aggacttttt agcaaaacat tctaatttct ctactgggat tattgtttgt tgtcttcctc   99360
cacaataatg tgagcactaa aggtagagac ttttgcgtac tttgttcact actgcttcct   99420
ctgcaccaaa aacactgcct ggttgtgggt acttttctag ttttaggaag gagaagacaa   99480
gatataggtc ctgactctgg ttctgcctct cattcatatg ctactccgag gatcccttcc   99540
ccttgaagaa cttgtttctt catctacgaa atggggataa tactactact catcagggtg   99600
gttgtgagga ttaaacaagg taagagatgt aaaattgcat gttagttatc agatagtttt   99660
gttttcccat ctagctccat gagggagagg atttgctcta gtccgtccgt ctgggctctg   99720
ggcttctaat gggcagacac cttcctccat gatgtttgta gctgcaaagc ctggcacagt   99780
ccctcaagac aagctttttg acttgaactg ctgatggtct tccatgcaca attcaacaga   99840
aacccagtag catacacttc cttgtatgca cttcccctc ttttacatt tattacacat    99900 tcattgctac ctaataatcc ccgatactta tcttttactt tatccaatta ttcaacagtt   99960
ttcaacagaa atacctagaa gagagctatt ccgacttcat tagaccctga gattctattt  100020
ttaacatttc ttccatggat tgttgaatgt ttccaatgat tgatccacct tcccttggcc  100080
ttatctgcat tccagatttg gttgtgtgtc catctctgtg ttgccagact tacctcacag  100140
acccagcttg aacacaagat gggtgcttgc tgaagagcag gactcattct gttgaacctg  100200
catgctttct caggtcagat tgcttggtgg tgcttcttta atttctttca acagcacatt  100260
gtagtttgct gtgtttaagt gttgcttttc tttggttaaa gttattctaa gtattttatt  100320
ctttttgatg ctattgtaaa tgaaagtgtt gttttaattt tgttttgat cctttactgc   100380
```

-continued

```
aaatgtatac tattgattttt tgtgtattaa tcttgtatcc tgcaaccttg ctgaacttgc    100440
ttatgagctc taatggtttt taagtgagtt ccttaggagt tcctataatg tcatctgtga    100500
ctaaagatag ttttacttct ttctttccga tctggattcc accttgttcc tttttcttgc    100560
ctaattgccc taataaatag aagtagtatg aatgaacatt cttgtcctgc tcttgatctt    100620 gagggggaaac actcaatctt tcacaaggaa tgaagtatgg tgtttatagg tttttcatag    100680
atgctctttg tcaggctgag gaagttcctt tctagtcttc atctgttgag taattttatc    100740
ataaaaggat gttagatttt gtcaaatgcc ttctctgcat taggatgatc atgtgacttt    100800
ctattaatat gaagtgctat atggattggt ttttgtacat tgaaccacat ttgtactcct    100860
gggataaatc ctacctggtc aatgtgtata atcctcttaa tatgctgctg aatttgattt    100920
gctaatattt tgctgaggat atttacatct atatttataa ggatattgct ttgtaacttt    100980
attttcttat aatgtgtttt tctgtctttg gtatcagggt aatgctggcc tcatagaatg    101040
agttgaaaaa tatttcttcc tgttctattt tttagaagag ttttgaagg gttggtgtca    101100 attcttcaag cttttggttg aattcaccag tgaagctatc tggtcctgga cttttctttg    101160
tagggatttc atttattgat ttattgatttt atttttttgag acggagtctc gctctgtcac    101220
ccaggctgga gtgcagtggt gcgatctcgg ctcactgcaa gctccgcctt cctggttcac    101280
accattctcc tgcctcagcc tcccgagtag ctgggactac aggtgcccac caccacgccc    101340
catctaattt ttttgtattt ttagtagaga tggggtttca ctgcattagc caggatggtc    101400
ttgatctcct gacctcgtga tccgcccacc tcagcctccc aaagtgctgg gattacaggc    101460
atgagccacc gcgcccggct ttttggtagg atttttaaaaa aattaatatt ttaatatctt    101520
tacttttaca ggtctattca aattttatct tccttcttaa gtccgttttg gtagattgca    101580
tgtttctaaa attttctcat ttcatcgagg ttatctcatt tgttcacata caattattca    101640
tagtatttct ttataaaacct ttgtacttct ctaataccag tagtgatgtg tccattttct    101700
ttctttctgg tgtctggttt tttggttttt gtttttttg ttttttttt tgatataagg    101760 ttttcctatg ttacccagac tagagtgcag tggtgcaatc acagctcaat gtaaccttga    101820
attcctgggc taaagtgatc ctcccacctt agccacccaa tttgctagga ctacaggcgc    101880
gcaccaacac actcagctaa tttttttcttt cttttttttt tttgagacga aattttgctc    101940
ttgtcaccca gggtggagtg cagcagtgtg atcttggctc actgcaactc tgcttcttgg    102000
gttcaagcga ttctcctgcc tcagcctccc gagtagctgg gattacaggc gcctgccacc    102060
atgcccagct agttttttat ttttactaga gatggtgttt caccatgttg gccaggctgg    102120
tctgaaactc ctgatatcag gtgatccgcc cgtctcagcc tcccaaagtg ctgggattac    102180
aggcatgaac cactgggcct tgcctcctag ctaattaaaa aaaataaata actcttttg    102240 tagaaacaag tctcactatg ttgcccaggc tggtctcaat ctcttggcct caaatgatcc    102300
tcctgcctcg gcctcccaaa gtcctgggat tacaggtgtg agccattgca cccatcctcc    102360
actttcttgg tgaataattt gagtcttatt ttttcacttg gccattctaa ctaaaggttt    102420
gccaagtttt gttgatcttt tcaaagatcc aattttggt ttctttgatt ttctctattg    102480 ttttttctgtt ttccatttca ttttatctcca ttctaatctt tattatttcc tgtcttctat    102540
tggtgttggg tttatttgc tcttattttt ctagttcctt aaggtgtaaa gttaggttat    102600
tgattgaaga ttgttcttct ttaacttagg tgtttacagc tataaatttt gctcttagca    102660
ctgcttctgc tgcatcctat aaatttgggc atgttgtgtt tcattttta ttcattcaag    102720 atacttttta atttcccttg tggttttgtc tttgacccat tggttgttta agagtgtgcc    102780
```

```
gtttaatttc tatgtgcttg tgagtttct agttttcctt ttgttcttga ttttaaactt    102840
tattccactg tgtccagaga acacccttg tatgatttca atcttcttaa atttgagact    102900
taggaccaaa tatatgctct atactggaga atattccatg tgctctttag aagaatgctt   102960
attctgctcc tgtcgggtag aacgttctgt tcatgtctag tgtgtgcaat tggtttacag   103020
tgcttttcaa gtcctctatt tccttgatgg tcttctgcag ttttctatt actgaaagt     103080
ggggccaggt gtggtggctc acgccccgaa tccctttggg gattcagggt ggctcagcac   103140
tttgggaggc tgaggcgggc gatttgcctg agctcaggag ttcgagacca gcctgggcaa   103200
tacaatgaaa ccctgtctct actaaaatac agaaaaaaat tagctgggca tggcggcatg   103260
tgcctgtaat cccagctact caggaggctg aggcaggagg attgcttgaa cctgggaggt   103320
ggatgttgca gtgagctgag atcgcaccac tgcactccag cctgagtgac agagtgagac   103380
tccatctcaa aaaaaaaaa aaaaaaaaa aaaagtcagg tattgaagtc accaactatt     103440
attactgaca acgtaatcat atttaaccct ttacttttaa aattcttttt ggaaactgga   103500
aggatctgta accaccaccc acttccacat cagaccctat gcatacgcca actgtctgtt   103560
gctcagcagc tgtgatgttg ttccagttct ttattaggca aagaacagtt gtttttttag   103620
catttccttt aaggaaggtg gctcagatca ttgagccagc caggccctgc aggatgggct   103680
gcgattaggg tcacaagtac ttctcccgaa actcacagat tttcctcgtg accattggat   103740
ccaatgttga aaagtcccag tcggccaact gcattagtcg atcatgggcc tcctaaaga    103800
ggccacagcc aatattcagc tccacccgca tacgccactc agctagcttg gagctgttga   103860
ggaagacatt atagttggct gccatgggct gtggatagac aaagacgaag atgtggtcag   103920
cctggggacc agccccacct gggtcctctc ccacagcctc tggcccacgt ccctaacatc   103980
tacctatgga aagaattagg ctgctgaccc ccaaggcctg agcaagggt cacagactat     104040
gtaatagatg taggtgggga tggaggatcc agaatccctc agagtcctca gtcactggtc   104100
ttcttgctcc aagccttctg aaccacactg agagggctcc tggcccaggc agctcccact   104160
tctccagcct gcgacctcgc atgaatcctg ccttcttcca gggaaacccc ttatcccagg   104220
tgtgtatatg cggatgaggg agagaactca ggttttttcc tccatgttta gactcccact   104280
atgatcaagc tcagggcta agatgggaga cctggcgggc agtctaccct gcagtttcgc    104340
tggctcacta agacagtcta ccctgtagtt ccgtttgcac ccaagatctt tgggaagcca   104400
aagaagggt gggtcgttgg tgaaatgtaa ggggtgggga cgaagtatat ggctgaaccc     104460
ttggggcagg ccagaatgat ttttcctggt gctggtctgc cctgcaaaca gaccaaagag   104520
actaatttc gtatcaacca gagatctctg caataggaa aagaacactg tatttcctgg     104580
tcaatccacc aggatcccag gtgcctcctc ctggcatatc tctggctgat atgcaaatta   104640
gtctctttgg tcagtgtgca gtgccctagc tggtgtgcag gatggccagt tgagaccctg   104700
gccagtgtct tgacaagcag aactggtcac cctcccctgc atgtagaggc cacataaatg   104760
ccccacactc aggtgtgcct ccaaatgcac agtggatgcc cctcagaccc agccacgaga   104820
gctgtcctcc agagctgtct gtctggagct ctgggaaaca ggcagggcca gaaggacacc   104880
caggaagcca gtgaacattt cctggagagt ccagcaagag gaggagtat ctgggatgct    104940
ggtggattga gcaggaaatg cagtgttctt ctctatccca ggctcaccct ccgggtcctc   105000
ccacaccgaa gaatctttgt caagtgtgga gaactgtgat ccttcctgat tcataacatt   105060
ctgtgcttcc tgttgccccg attgagtcca ggccccagg cctggttccc gcagcccca    105120
```

```
tggcagctct gcctgccttt cccgcctcac cagcctatcc tcaagtgatg gccccattgg   105180
tcacagagga gtcctacctc tgcccagggt ctaaccctcc tccaatccac tccacacctg   105240
catcatctcc accacggcca ccaggtcagc cagtgagatt tggttcccgg tgatgaacat   105300
cttatcctgc agaaaatact cctcaaagag ctgcaggctg ttcttcacct cttccactgc   105360
atgctccatc ttctcagctg aaacttcctt ccctgttatc tttgggatca gcaactggcc   105420
agggttggga agaggaggga agaggaggct gtactccagg gccacctgcc ctgccaggtc   105480
tctgtactct tgtctgctgg atagatattg aacacttccc aggatataaa gcagtttcac   105540 ctctttttagc agttctgatt ggtggaaggt gccgggaacc atgcgttcac aaggatttgg   105600
ggagctcagc aggcataagt cctgtgattg attagtgatg ccggtcacag gcatggaatt   105660
tgaagtagag acacgtgtac tggttatttg tcatcttcca attttctttt ttcttctttt   105720
tttttttttt tttttttttt tgagacggag tctcactctg ttgcccatgc tggagtgcag   105780
tggcgggatc ttacctcact gcaacctccg cctgctgggt tcaagaaatt ctcctgcctc   105840
agcctttgga gtagcgtgga ttacaggcac atgccagcat gcctgggtaa ctttttatatt   105900 tttagtagag atggggtttc accctgttgg ccaggctgtt attgaagtcc tgaccttgtg   105960
atccgcccac ctcggcctcc caaagtgctg ggattacagg catgagccac tgtgcccggc   106020
catcttcaaa ttttctatga gccatttttt tttttttttt tgagatggaa tctcactttg   106080
tcacccaggc tggagtgcag tggcatgatc tcggctcact gcaacatcca cttcctggt   106140 ttaagcgatt ctcctgcctc agcctcctga gcagctggga ttacaggtgc ccaccaccac   106200
accagctaat ttttttttgta tttttagtac agacagtgtt tcacaatgtt ggacaggtag   106260
gtcttgaact cctgacctca agtgatccac ctgcctcggc ctcccaaagt attgggatta   106320
caggcgtgag cactgctcct ggccttctgt gggccttttg acgctgagat tctctagttc   106380
agaatgaaat gcctcgaatg ctgtcctggg tgagtcacat cagcccctcc cgtatgccct   106440
tcccctcgcc ctaataagac tctttcatgc ccattgtttc agtccacact cctgacggct   106500
ctgtaaggcg gcaggagaa ggagctgagg aaatgaggcc cagagaggga gggagacttg   106560
cttgaggtcg ccggcagtca gcagggccag aactggcctc cagccttcct gacttccctg   106620
tgcccgtgtc cccaagcccc agaagtggcc ctgctcacct tgagccagac tatcttcttc   106680
atgggcagct gaaaggccgt gtgttgccaa gccacgaact catccacacg ggcacgtgcg   106740
tgcgggtctg gcgggcacca gtgcgatggt gcgctgtact gcggcacag gtagtaaagg   106800 atggccgcgc tgcagaaggg gccggtcagg ggcactgccc ttgccttcct gagtgccact   106860
acatcaacca ccccggtgtg gcctgggccc aactgctggg gcttcagag caaagaggag   106920 cccaaacggc cccgagaaag accttcacca gagctgtctg tctgacagtc agtaagggct   106980
gggaaggagc cctgcggggt gagtaggagt tggggctgg tggtataaca aagagtaggc   107040 cagcagggg aacaacacgt gttgaattgg gatgctgagg tgggaggatc acttgatccc   107100
aggaatttgg ggctactgtg agccaagatc acaccactgc actccagctt gggtgaaaga   107160
tcaagatcct ttttcaaaaa caaaaacggg ggggcacgat ggctcacacc tgtaatcccg   107220
gcactttggg aggccaatgg gggcagatcc cttgaggcca ggagttggag accagcctgg   107280
ccaacatggt gaaaccctgt ctctactaaa atgaaaatac aaaaattagc tagttgtggt   107340
ggcacacacc tgtaatccca gctacttggg aagctgaggc acgggagtca cttgaacctg   107400
ggaggcagag gttgtagtga gccaagattg tgccactgta ctccagcctg gccacagag   107460 caagactctg tctcaaaaaa ccaacaaaga aaacacatg ctgaaatacg agggtaaagg   107520
```

```
gagcaaggta aatctgaaga aaagagagta gggggttgca actggaagaa gggtgggggt    107580
gattggggag tgatgaggca gccagagaca ctgtggagtc cacggagggt agcccctgga    107640
ggtgcaggga ggttatggac ttaatgctta agattaggca ttatataagc cagggcatga    107700
aaggatccat ctctctggtg ctggatggag ggtgagcccg aggggcaga atggacaatg    107760 aggggggccag caactatcgg gaaggttgtg gtgtctggga atgttggagg ccatggggac    107820
agagggaagg ggatggaggg gagacatgct tcggagggga tgtcctaggc cttgctgatt    107880
gatggctggt gtgggaacct ccgcagcaca agggctcctt tatcatcacc agcagcaacc    107940
atgccaaggt aaaaggtca gggcatggag agagctatcg gttaaaaagt ggcaggagag    108000
acagcaactg gctgcaagac tcagaacttc ttggctgggc acggtggctc acgcctgtaa    108060
tcccagcact ctgggaggcc gaggcggggg gatcatgggg tcaggagatc gagaccatcc    108120
tggttaacac agtgaaaccc cgtctctact aaaaatacaa aaaattagc caggcatggt    108180 ggcgggcacc tgtagtccca gctactcagg aggctgaggc aggagaatgg cgtgaacccg    108240
ggaggcggag cttgcagtga gccaagatag cgccactgca ctccagcctg gcaacagag    108300 cgagactccg tctcaaaaaa aaaaaaaaa aaaaacttct ttggatcctg atccaaacaa    108360
actgccaaga aaatgtttag gagataatca tagagttttg aacaggagcc acatattaga    108420
tgaaatccag gaattattgt taattttatg aggtatctta atggtatcgt agtgatgcta    108480
cgctctatcc tagcccaggc tggagtgcag tggcgcaatc agagttcact gcagttctga    108540
acttcctggc ctcaagcgat cctcccgtgt cagcctctgg aagtgctcgg attataggca    108600
tgagccacca cacccagcct gttgctttt ttttgtttgt tttaagaact cttatctctg    108660
aaaagtatgt tcctaaacat ttattgattt atttacttat ttatttttat ttttgagatg    108720
ggatctcact ctgttgccca cgctgaagtg caacgacgca gtcttggctc actgcatcct    108780
ctgcctcctg gctcaagcag tctttccgcc tcagcctccc gagtagctgg gactacaggt    108840
gcagaccacc atgctggcta atttttgtat tttttgtaga gatggggttt tgccatgttg    108900
tctaggctag gctggtcttg aacacgtgag ctcaggccat cccctcactt cagcctctca    108960
aagtgctaga attacaggca tgagctggct tctaaacatt tatgaatgga atgatggggt    109020
gtctgggagg caggggaata gaaatgatgt aaactggacc ccaagttggc aagagtcaga    109080
gctgggcgat ggatttgtgg ggttcctcgt gtccctcatt agttagtatt cactctcctt    109140
tagtgcacgt gtgagatttt ccatggtcaa acagacaaat gcttgcactg aacctcccag    109200
gagaagcaga gacagatggt gcaagggccc cagggaagac ttacctttca cttaagataa    109260
atttcccatc tttgaggctg ggcagcttcc tgagggggtt gatgtcaatg tatcctttgc    109320
tgtggtggtg acctgggagg ggcagggaag gtctgaggct gtgggactcc aggggagaga    109380
gaactgagac tcccagagac ccaaacgcct ccctctctat tttctcaaga agagggaact    109440
gaggcccgga gggacattgc gtctcacccc aggtcacagg gcaaggcagt tgcagaaccg    109500
gactgcgatc agaactgctg gctcccagcc tgctccaccc taggtttggt gactcccgtg    109560
cctcctacct gtgtcccagg accaggacga cccttttacc cagaagccgg aggcctccag    109620
tgcccacccc caaagctgga tctgaaaaca cagcctttga atcacctgaa gcctgaggg    109680 cctgggtccc atccgcaatc ccatcgctct cactctgtct ccactttaag gaagccaggc    109740
ccagcacaca gctggacatc caaagggaag cttctcggac acaatcaggg tcatcttaac    109800
agggaacctg aggtgggggc aggaactgaa actcttcctg gaccagccgc ctccagttgg    109860
```

```
aaacatttct gggggctcca ctcgcagccc gttcatttcc acagcttccc tgtctcttcc    109920
tctgtgttct agaggcttct gcttttgcag gctgagcttt tggagtccct ctgtgctggg    109980
gatggagttg gagcccaccc ctctgaccct cactcaggt tagtggagcc ctgagccttt    110040
ctgaacactg gggaggatgg gtgtagacgg actgtgcact tctgcccct ttgccaacct    110100 ggtgggcagg tgctgagttc acaaggtcct agaatcccac aaggaagcca gggtgcctgg    110160
tgggagccca gggagtccca gctactgttc cttccccctt ctcctcgaaa agcctgttca    110220
tctgtggcgt ggggactgtc attagtgagc actgactaag gtaggctgga caaggatgca    110280
gcctacaagc cgcgtggcat cttttccttc cctgtggacc tctgggtga ttcccttgtc    110340 tctgtctctg ctcctcagaa acgcccctat caggctgtgc gcggtggctc acgcctgtaa    110400
tcccagcact ctggaggctg aggtgggcag atcacttgag gtcaggagtt tgagaccagc    110460
ctggccaaca tggtgaaacc cctgttaaaa atacaaaaaa ttagctgggc gtggtggcat    110520
gcacctctaa tcccagctac tcgggaggct gaggcaggag acgcacttga acccagcaga    110580
ggttgcagtg agccgagata gcaccaccgt actccatgct gggcaacaga gcgagactcc    110640 atcaaaaac aagaaaaaaa gaaaagccgc aatctgtgtg tcctgcctcc ccccaggacc    110700
aggcctgcca ggcagcagtg gggagttgacc tttcagcaga tccacaaaact gaaagttgaa    110760 ctggatgtca tgcttcttcg agaagatgta gacggcacgg cagggtgctg acagcaggtc    110820
catgtagagc tccagtgcca tgttgagaca catgccaggc cccacagccg cagttggcca    110880
gccacagacc tgggcctatg tctggccaga gtccctggcc ctgtgccctc tccgatctgg    110940
gcccaggatc ctgtgttccc cagggaaacc tcttgtttcc ctttgtgttg tcataaggcc    111000
aggaagcctg caattctcac agcatcaagg attctaagga ggcccaggag taggctgggg    111060
agaggcccgt ggcaaaggtg tggcagccgt gaccctactc tcccccttcc acgtgtgcct    111120
gtgccccgtg gtgccacctc acagacacca gtctgagaag ggattatgcc tgggaattcc    111180
cacggctgga ttttcattgc agaacctgac gaaagggct ttgcagggtc cagaatgaag    111240
aggaggcaat gagaattatc cctgaggat tctagaagta gaggctggga gtatccacag    111300
gtaaatcgag cctgaactat gactagaaag gaattgggag aaagagacac aggtgaatcg    111360
agcctgaact atgactagaa aggaactggg agaaagagac acaggaaact gtgagctttg    111420
ggagcaatgg ggacaccacc accaggaagt caggggggcac tcagccggtg tgtgccacac    111480
agaggagcct agaaacttcc tggccttggt tggggctgca gtggcagac tgtgtacctg    111540 gtggccaagg aagtaactga gagccccacg tagaggactg agtgccactc actctatgct    111600
gtgatctaat aggtctaggc tgagaaatgg gactgacccc acttctggtg acagagtaag    111660
cctggagaca agcgaagagc atgcagtgtg tttattgcag acagcagggt gcagtggagt    111720
gggctgcacc cactgcacct gcttctgggc cagctggggg tccgccaag cctcactgtg    111780 gttcagaggc tggagtatga gcttgtgggc ctccagcaag agctcagtac caagggcagc    111840
cgccacacgg gcctgccaca ctgccagccg gggcagtctt ggaagaggtc gcagccaacg    111900
gcagtgggct gggaagacag ggcagctggg gttgggctc agcccatgc ccagagtccc    111960 cccagagggc aggtgggtag gaaagcttca cctgcatcac ctccgtcagc accagtcttt    112020
ccagggagat ctgctccatt gccaggaagg gcctggccac cagcacccc caatccaggt    112080 gctgcagggc tggcatcagc ctccccaaca gccgctccag ctgtgcagca tctgcaggct    112140
gtccggagaa gtggggcagg agagactggg ctggaggag aggagcaact aacccagac    112200 tcttggaagc ctcttgggcc tcctctccat cccttcccgg ctgccactca ttagtgatgt    112260
```

```
cctctggggc tctgtgttca gaaggtttct aaggattcat tcaggcttag gggaaggagt 112320
actgtgatag attagttatg tctgctgagg acagtggaag tgaagctaat atgtaatatg 112380
taccaactgg tgccttccat ctctggggt ccaggcccct gccccagcct gcatgacagg 112440
gcctaggaag ctcaccttgc acaggtagac attggtggca ggcagctgga tggtgacatg 112500
cttccacgcc aagtactcat ccacgcaggt gcgggcttgc agctcaggtg ggtaccagtg 112560
tccccgtatc tggtactttc gactcaggta taaaacgatg accatgctgt gggcagggg 112620 tgtcagagat cttttctcca gcctgtcagg gccaggtggc ttcattgctc atactcaggg 112680
tgatttgacc aggttttctc cccaccttca ccttcagggg aggacctccc ctatactgca 112740
actccctcca ggcagtatct ccccacgacc aaaccactct gtttctccat ttccaactct 112800
gatcctccct gggcccatgt ttccacctcc ctcccagtt accataccat cctgccctct 112860
gtgcccaggc cccactccct ggcatcaggg tccccactca gagtgcctgc cgtgtgggcc 112920
ctgcccaaaa ggtctccaag ttcccttcct agtgcccag aacactaggt gcccattttc 112980
tatcctcagg taagccctgg gaggtggata cattattcct cccactccgt tttacagagg 113040
agaaacctgg cacacaaagt tctgtgattt ccccaagggc atggattgag gaagtggtga 113100
gctgggattg aatgtggagt ctcccctggg tctgcccagc tcctaggact ctgaaaggat 113160
gagctgggga catttgggga ggagccagcc tcaagcctgg gccttgcccg ctggcttcag 113220
gttgtccagg tttatccggg tgacctacgt cctttcccca cctgggcagc tccagctggc 113280
tcagactcta gccaggttcc agcctccagc tttagcccaa aggtgcccct gggtccagcc 113340
tctgcatcgg agctacacag gctgaaatga ggaaggggcc tcagtgattt ggaaagatct 113400
ccaagccaag gaaagatctc ccctctcgcc tctgcctccc cctacaactc tgagcccag 113460 aacccaggca gatcctggct ctgaccctgg gtgggcacca ggtcaccatt acctctttgc 113520
tagtaggaag tcgccatctc tgagggcagg caccttcccc aggggttca ccttcaggaa 113580 ctcaggcttc aggtgctccc ttggtgggca gaaaggcgag aaggctcagt gtagggcctg 113640
gtccttggca cccactccat ggggcccagc ccagccacct ggctcacccc aagccaactc 113700
caccatccac agctcaaaag ggatgtcatt ctgtcttgca aaagtggata gtgtgtcagg 113760
tccaggaaga gctcaagccc cattgctgct cctctcacct gccctcccca gaattctgga 113820
cctccaggag ttgctcagcc cttctccact agttctgagc tgttcctgt ccatagtctg 113880 ctgtagtggg ccagagcaca gggcagattt gtcttcagg actttctctg ggcattcctg 113940
ggcagagaac ttcatcttct ctgttaactc ttgctgataa ttctctgtag ctaggcacct 114000
tgtaaaaccc atgtcccaga atgccaaacc tggaaatgca atgtcagcgc cgaaactgca 114060
ttgaaactga atgaatgagg tccccaccct cttatctaaa tatcctatca gtctgttgaa 114120
tgtcaaagta tgtaggggtg gtgtggggga gcctataggg agtctccatt tctgtagctt 114180
tccacatgtt ccatgcagaa ttttcctcta atgacccttg gacaccgtgg tggtcactgt 114240
ttccctgcat aaacctttga tgatccttat ctttagcgta ccagtgaaac accaaaattca 114300 gattttcagt ctgtgcagtc tatgtagtta ataaaatcaa tttctaatgg aatatgcctg 114360
tgcctggtgt gtttgtacct aaccactgct aaggactttc attgatagct agaccttgga 114420
gttccttccc ctggaccct gacccaagta ttttgcactc attcctctgc cagtgtgttt 114480
catggtgtcc tgcttcccag agtgcctcag ggaatgcttg cattggatat aaatgaatcg 114540
ttgcggtcac catggatggg attcaggcct aactctcacc aagaccataa ggccacagtc 114600
```

-continued

```
tttgatatag attccccatg ttaaatctgc catcctcagt gtagtgagag tgatattgag 114660
agagaaaagt taggtaatta aggtgggtcc ttggtaaaac tcctttaaac agaggaacag 114720
cctgaaaaat caggcttcag gcacagataa ggaaacttgc acaaacctct ggctcactca 114780
gataaaggaa caatgcccaa cacagaaaca cctttgatct ttgtgcctaa ggcatgccca 114840
cagctacttt gataagggaa caagaccag catagaaatg cctttgtcct ttgtataacc 114900
agtgggcttc caggaaatag tctcttctcc ttttgtggac atgtacacgg tgggctacag 114960
tgggttccag tgggcacttt cctttcttgg acgtgcttta gaatgtgagc ctctgattgg 115020
tcctgggcca ggctatcact tcagctcctg attggtccct caaggtccag gggccaagct 115080
gagtagtgct ttctccaaga ccagtcagta cattccttcc tttcccagtc cataaaaccc 115140
cctgacccag cctcataatg ggcaacctgc ttgggccccc cgccagctgc aatgagcttt 115200
cttcatttgc ttattaaact tttgcttcaa ccttacccct tgtgtccaca ctccctaatt 115260
ttcttggtcg tgagacaaag aattctgggt gatacccac aatgagagac tggtacattg 115320
tggtgcacgg gcaagactgc aacaatatgt tttctgcttg cttgtttgga ctggcctctt 115380
cctaactctc cagagtgctc tctccccact gtggccctga gctttgcctc acggtaacac 115440
tgtgctgcat gacactccag catgatctgc atgtttctca cctccggacc ttccccacac 115500
aactttcttg ctgcttggac cacccttccc acctattttc aactgtttct ctccagcgca 115560
tctttcatga taaggcttga gtggaagctg tatccgaggc tgaaggttat ccatgcagct 115620
ttgaaaccat ctgtttatgc ttctgtttac cccccaaata ctgtttaccc caatactcaa 115680
agtcaaggtt ggtgactcaa caattttcag aacttctagc ttatcagtat agctttattg 115740
tactgaactg agttttcac catgctgtta ctgtctttga ggttaaaaag ccccaacat 115800 tcactcctat ttgaatcatc tgtgcaagac tcaagcagct atgaattcaa ccacagtgta 115860
aagttcttcc ctacaatgct ttattgttat tctagctccc aagagagtac catctttcag 115920
cccaagaccc ttgacagaac cccttcaact ctgtcgcctt ttttcatctc tggaattctg 115980
acaccaccca tgaccctct tcttgttcat ttactaggtt ttgttccttt ttttcctttt 116040
gtttcaatat cctattgtat ctgttccttt tgggcttcac atccttttg gaaagagagg 116100 cacaggtaat ataatgaatg aggatgctcc tcctccctgg ttccctctaa gtcaagtttc 116160
tccaacgcgc tggtctgctt ggctttgaat gcggctcaac acaaattcat aaactttctt 116220
acaacatttt gagattttt ggtgatttt attttatta tttatttatt tattaactta 116280
tcagctatcc ttagtgttag tgtatttat gtgtggccca aaacaattct tccaacgtgg 116340
cccagggaaa ccaaaagatt ggacaccccg ctctaagtgt tccccaagtt tccactgttt 116400
tcagagcaca tgtcccaggt aataacacac agcccatcat ttagtgactg ctcagggtgc 116460
aagctgtgga gaagagagtc cgactacgag ctggtgctct aagcctccag cacgctagga 116520
ctgacgacgg ggatccggaa acaacaagct ccactcccgc aacacacaca cacacacaca 116580
cacacacaca cacacacaca cacacgcaca cgcacacgca cacgcgcacg cgcgcacaca 116640
cgcgcacaca cgcgcgcacg cgcgcgcgcg ccgcccaagg gtagccgtct gcagggcccc 116700
agctaagcag cccgcggaga gcgagcggcg cgtgcgcccc cgctgattgg ctggcacaac 116760
cggcaccgga gccaatggga gcacgccttg ttgtcaggcg cgcagccgga cggcgcggtg 116820
gtcgggacag actggccgtt gctgtggaga cgcctggtga gttcctggaa ggctggtttg 116880
aaggcggtgc cgggtgggg gtgaggctca gcagagcccg gggcacaggc cggagggct 116940 gcaggcgcga ggctgggtta cgtgaggaag ctgggggttt cgcgggcagc tttagagccc 117000
```

```
cagtcaggga aaccgaggcc gggcttcctg gctgcctcgc gagcctcttc atggctctcg   117060
ccgccgccct gaggtgccta gaatgggttc cggcctccgg ggaggttccc agtaaccgca   117120
ggagccacca ttgatttggc gtctgctggg tgcaaagccc agcgcgctaa cccttttactc  117180
gcgacctttc gcttcacctt cacagcagcc ctgcgaggtg agtgttgtta ttggtgccat   117240
ttacagggt  ggaaactgag gccgcgggta ggtgaaatga tttgctccaa gtcacccagt   117300
gggtgagcgc gactccagac tgaaaatttt gaccgttctg cttcactgcc tcccgcaag    117360
aggcgggccc tggccagatg gaactcacct ggcattccca aggtatctgc acaagtggct   117420
ttgggagtca cttaactctt caggacctgg gttattacag gttataagtg tgggaccgtc   117480
ggattccatg tggctaagat tctttctatg tgattattgt ggttagaaat agaatatgct   117540
tagaacagtc tcgttcagcg gtcggcaaac ttttgttgta aatatatcag tgtttacatt   117600
gttatattgt aagtataatg agtataatag tattcataat agtagtttag gcttgggggg   117660
tccatactct gtctacttaa ctgtagcgat gtagtgtgga tacagccaaa gacaatacat   117720
aacagactag ctgcgtcgca ataaaatttt aattataggg accgaagttt taattttata   117780
tattgttaat ataattttca cgtgtcatga ttttttttcc caaatatgaa aaaatgtaaa   117840
aaccattctt tgctcgtggg ctgtacaaaa agggtgggct ggttagcttg cagaaccctc   117900
atctagtaca aagcctcata catgagggga aacagactga gagactgaca tctatgtcaa   117960
gtcagtcaca cagccagggc actgccacca ctgagcttaa gacataggct tcccaccttc    118020
caggccagga aacatcccca gttatcactc tggatcaggg tgctgaggtc tgaaggtgtg   118080
ctactcttta tcgtgttctg aggccatgga aactatattc taagggggttt ggaaacttat  118140
tagcttagac taataagcct ggtgaatgtg ctgctatctg aggaaatgca gctgctgggc   118200
tgggagtcag aaatgaatag atatttttct ttttcatgat tattcaatag ctttttttgtg 118260
tgtgtgtgtg acggagcctt ggtctgtcgc ccaggctgga gtgcagtggc atgatctcgg   118320
ctcactgcaa tctccgcctc ccgggttcaa gcagttctcc tgtctcggcc tcccgagtag   118380
ctgggactac agacacccgc caccatgctt ggctaatttt tgtatttta gtagagacgg    118440
ggtttcaccg tattggtcag gctgctctca aactcctgac ctcaggtgat ccacccgcct   118500
cggcctctga aagtgttggg attacaggcg tcagacaccg cgcccggcct caatagcttt   118560
tttttttttta aaagctccct ttagtgagtt tcttggattt atggtgaaca atacataaat  118620
ggttaccatc ctcacattgc ttacagatga taaatatata atcaaaatgg ttatttcttt   118680
ttaagctttt tttttttttt tttttgagat ggagtctcgc ctgtggccca ggctggagtg   118740
cagtggtgcg atctcgcctc actgcaagct ccgccgcctg ggttcacgcc attctcctgc   118800
ctcagcctcc ctagtagctg ggactacagg cgcctctcac catccctgc tagtttttg    118860
tatttttttag tagagacgga gtttcaccgt gttagccagg atggtcttga tctcctgacc  118920
tcatgatccg cccgcctcgg cctccaaaag tgctgggatt ataggcgtga gccaccatgc   118980
ccggcctctt tttaagctt                                                118999
```

<210> SEQ ID NO 33
<211> LENGTH: 7
<212> TYPE: DNA
<213> ORGANISM: Homo sapiens
<220> FEATURE:
<221> NAME/KEY: misc_feature
<223> OTHER INFORMATION: Sequence of Figure 4: HA5

<400> SEQUENCE: 33

```
acgtcca                                                                    7

<210> SEQ ID NO 34
<211> LENGTH: 7
<212> TYPE: DNA
<213> ORGANISM: Homo sapiens
<220> FEATURE:
<221> NAME/KEY: misc_feature
<223> OTHER INFORMATION: Sequence of Figure 4: H0 and HA3

<400> SEQUENCE: 34 acgccca                                                                    7

<210> SEQ ID NO 35
<211> LENGTH: 7
<212> TYPE: DNA
<213> ORGANISM: Homo sapiens
<220> FEATURE:
<221> NAME/KEY: misc_feature
<223> OTHER INFORMATION: Sequence of Figure 4: 3?sequence  HA5

<400> SEQUENCE: 35 atgcagt                                                                    7

<210> SEQ ID NO 36
<211> LENGTH: 7
<212> TYPE: DNA
<213> ORGANISM: Homo sapiens
<220> FEATURE:
<221> NAME/KEY: misc_feature
<223> OTHER INFORMATION: Sequence of Figure 4: H0 and HA3

<400> SEQUENCE: 36 atgtagt                                                                    7
```

METHOD FOR DETERMINING THE PRESENCE OF AT LEAST ONE ALLELE OF A GSTT1 DELETION MUTANT

This invention relates to a method for detecting the presence of at least one single allele of a deletion mutant, a PCR assay for detecting the presence of at least one GSTT1* allele and a procedure for diagnostic testing of patients to check whether they are susceptible to toxins or resistant to certain therapeutic agents or belonging to risk groups.

Human glutathione S-transferase theta (GSTT1) is an important detoxification enzyme comprising a deletion polymorphism. Approximately 20% of Caucasians are homozygous GSTT1*0/0 failing to express any GSTT1 activity. Non conjugators may have an impaired ability to metabolically eliminate toxic compounds and may therefore be at increased risk for cancer, inflammatory diseases or chemical poisoning.

Any conclusion drawn from current genotyping was limited because heterozygous (*A/0) and homozygous (*A/A) samples could yet not be discriminated. Phenotypically suggested high- and intermediate conjugators remained genotypically unexplained. The classification of all three genotypes has so far been hampered by the elucidation of the correct molecular mechanism of the GSTT1 deletion.

Thus, it is the object of this invention to provide a method for detecting the presence of at least one single allele of this deletion mutant.

This problem is solved by a method for detecting the presence of at least one single allele of a deletion mutant, wherein a PCR is performed with two primers, of which one stems from the sequence upstream of the deletion area, and the other stems from the sequence downstream of deletion area, wherein the production of the corresponding DNA fragment in a PCR is checked.

It is preferred to use this invention for detecting the presence of at least one GSTT1*0 allele, wherein a combination of one primer from the enclosed sequence 1 and one primer from the enclosed sequence 2 is used and specific DNA fragments for the GSTT1*0 allele are obtained by PCR.

Thereby, using the following primers showed very good results:

```
CAG TTG TGA GCC ACC GTA CCC    (SEQ ID NO: 21)

CGA TAG TTG CTG GCC CCC TC     (SEQ ID NO: 22)
```

A special purpose of this invention is to use the invention in a procedure for diagnostic testing of patients to check whether they are susceptible to toxins or resistant to certain therapeutic agents or belonging to risk groups, wherein blood samples from the patients are obtained and genomic DNA is prepared from these blood samples a PCR-Mapping of the obtained DNA is performed using a combination of one primer from the enclosed sequence 1 and one primer from the enclosed sequence 2 and it is analysed whether corresponding DNA-fragments have been produced by the PCR.

In a preferred embodiment, there is an additional PCR mapping of the obtained DNA using a primer pair from within the GSTT1 gene and it is analysed whether PCR fragments of the primers according to claim 3 and/or PCR fragments of the primers from within the GSTT1 gene have been produced. In this way, all possible allele combinations (GSTT1*0/0, GSTT1*A/0 and GSTT1*A/A) can be detected.

It is preferred to use this GSTT1-genotyping assay to predict the risk for UV mediated skin damage and/or the genetic risk for skin cancer and/or the genetic risk for cancers that are associated with oxidative stress and/or damage.

According to this invention, it is further possible to obatin a quantitative PCR assay for detecting the number of active GSTT1 alleles using the ABI TaqMan® technology.

With the method according to this invention, it is preferrably possible to use the knowledge of the exact GSTT1 copy number to develop quantitative PCR based assays for detecting the number of active GSTT1 alleles using the ABI TaqMan® technology.

It is further possible according to the invention to use the knowledge of the exact numbers of GSTT1 copoies obtained according to the invention to calibrate quantitative PCR based assays for detecting the number of active GSTT1 alleles using the ABI TaqMan® technology.

The knowledge of the exact GSTT1 copy numbers obtained according to the invention can also be used to calibtrate assays for detecting the number of active GSTT1 alleles.

In the following, the invention is explained in detail with reference to the enclosed figures and tables, wherein FIG. 1 shows the structure of the GSTT1 gene region and mapping of the deletion and the genomic organisation of GSTT1 (*A allele)

FIG. 2 shows the mapping of the deletion and primer localization as well as selective primer combinations and corresponding PCR fragments for mapping of the deletion:

| Primer Combinations: | lane 1 and 2: GST-TF13/TRF13, |
| --- | --- |
| | lane 3 and 4: GST-TF12/TRF12, |
| | lane 5 and 6: GST-TR11/TFR11, |
| | lane 7 and 8: GST-TR13/GST-TRF13; |

FIG. 3 shows the differentiation of GSTT1 genotypes by PCR assays:

a) Method according to the invention: a 1,5 kb fragment defines the *0/0 genotype, a 1,5 kb and 466 bp fragment indicate *A/O and a 466 bp fragment *A/A.

b) Method according to the state of the art: no fragment defines the *0/0 genotype, a 459 bp fragment indicates *A/0 or *A/A;

wherein lanes 1–3 represent samples from completely deleted (*0/0) individuals, lanes 4–6 from heterozygous (*A/0) and lanes 7–9 from homozygous *A individuals (*A/A), a 100 bp ladder (M) was used; identical samples were investigated;

FIG. 4 shows the sequence and the mechanism of the GSTT1 deletion:

The schematic representation of the recombination event above and the sequence of the recombinant fragment; the positions for sequences for HA5 and HA3 correspond to the positions on the complement of SEQ ID NO: 32 these sequence of H0 is SEQ ID NO 31;

Figure 1:
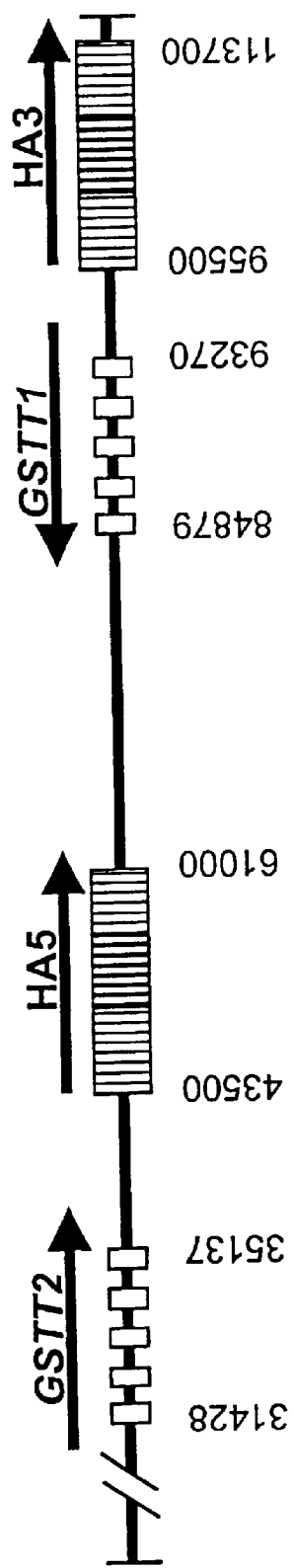

Table 1 shows the primers for the characterization of the GSTT1 deletion locus and diagnostic PCR;

Table 2 shows the GSTT1 allele distribution and phenotype correlation;

Table 3 shows the PCR fragments for GSTT1 genotyping;

Table 4 shows the skin sensitivity to UV irradiation dependent on GSTT1 genotype; and Table 5 shows the cluster analysis and statistical significance of the genotype correlation.

The invention characterizes the structure and mechanism of the GSTT1 deletion by PCR mapping and sequencing: a 54251 bp fragment carrying the GSTT1 gene was deleted from the functional allele by a homologous recombination event. The deletion breakpoints are concealed within a 403bp region on the null allele.

Based on this date a PCR assay using primer pairs (CAGTTGTGAGCCACCGTACCC (SEQ ID NO: 21), CGATAGTTGCTGGCCCCCTC (SEQ ID NO: 22)) and (CCAGCTCACCGGATCATGGCCAG (SEQ ID NO: 19), CCTTCCTTACTGGTCCTCACATCTC (SEQ ID NO: 20)) for GSTT1*0 and GSTT1*A, respectively, has been established according to the invention, that revealed all three GSTT1 genotypes (GSTT1*0/0, GSTT1*A/A, and GSTT1*A/0).

Furthermore, a Mendelian intermediary inheritance was proved by correlating the GSTT1 genotype with the enzyme activity using the substrate dichloromethane. Samples with two active alleles (GSTT1*A/A) expressed a statistically significant higher enzymatic activity compared to those with one null allele (p<0.0001, ANOVA)

This improved method can be introduced into routine genotyping as a new diagnostic tool and will help to elucidate the clinical relevance of this gene.

Glutathione S-transferase theta enzyme activity involved in the metabolism of toxic compounds is absent in approximately 20% of Caucasians due to a homozygous deletion of GSTT1(*0/0). Because the exact manner of the GSTT1 deletion was unknown, current genotyping of GSTT1 was limited to detect the presence vs complete absence of the gene by a GSTT1-specific PCR. Thus, heterozygous (*A/0) and homozygous (*A/A) samples could not be discriminated. The invention characterizes the boundaries of the deletion of the human glutathione S-transferase theta (GSTT1) gene: PCR mapping and sequencing revealed a 54251 bp fragment including GSTT1 to be deleted from chromosome 22, most likely by a homologous recombination event between two highly homologous sequence stretches that flank GSTT1. Based on the knowledge of the GSTT1*0 region, a PCR assay was devised for unambiguous discrimination of homozygously deleted (*0/0), heterozygously (*A/0) and homozygously GSTT1 carrying (*A/A) individuals. Genotyping of 180 samples of a Caucasian population revealed that the deletion consists of one defined allele, whose distribution in the population fits the Hardy-Weinberg equilibrium with observed 20% *0/0, 46% *A/0 and 34% *A/A individuals. The number of GSTT1*A alleles detected by this procedure correlated highly significant with the enzyme activity in erythrocytes. Genotype-phenotype comparisons proved a codominant type of inheritance by a gene-dose effect: samples with two active alleles expressed a statistically significant higher enzymatic activity compared to those with one null allele (p<0.0001, ANOVA).

Glutathione S-transferases (GSTs), a multi gene family of enzymes comprising several classes (class alpha, mu, pi, theta, and zeta), are expressed in many tissues, including liver, lung, heart, intestine, erythrocytes, and lymphocytes (Hayes et al., 1995). GSTs regulate the conjugation of toxic compounds to excretable hydrophilic metabolites. Because of that, their activity may affect individual susceptibility to environmental toxins, carcinogens, cancer, and other diseases (Strange 1999). The glutathione S-transferase theta (GSTT1) gene, and its corresponding enzyme activity is lacking in about 20% of Caucasians (Brockmöller et al., 1996). However, even within the Caucasian population, this frequency differs with respect to ethnicity (Nelson et al., 1995). A nonfunctional GSTT1 allele (GSTT1*0) is the result of a partial or complete deletion of the gene, the enzyme is completely absent in homozygots (GSTT1*0/0) (Pemble et al., 1994). Many chemicals, such as halogenated alkanes and epoxides whose use is widely spread in industry, are substrates for GSTT1 and thus their toxicity can be modulated by GSTT1. Interestingly, glutathione conjugation may cause detoxification as well as toxification. For instance, the conjugation of dichloromethane yields the toxic metabolite formaldehyde (Hallier et al., 1994) and the mutagenicity of several halogenated alkanes was enhanced in a GSTT1-expressing model system (Their et al., 1996). Thus, GSTT1 polymorphism may determine individual susceptibility towards toxic compounds. For example, of two workers that were accidentally exposed to methyl bromide, the GSTT1 conjugator suffered severe poisoning while the deficient developed only mild neurotoxic symptoms (Garnier et al., 1996). Since glutathione conjugation may provide a step in elimination of substances which are toxic per se, GSTT1 activity can also act protective (Ketterer et al., 1993). This explains that GSTT1 protected human lymphocytes from DNA and chromosomal damage after exposure to several halomethanes (Wiencke et al., 1995; Hallier et al., 1993). Consequently, GSTT1 has been investigated as risk factor in epidemiological studies. The deletion conferred an increased risk in myelodysplastic syndrome (Chen et al., 1996) and some studies have suggested a correlation with susceptibility of the skin to UV-irradiation (Kerb et al., 1997). Although substantial data on epidemiological associations between GSTT1 deficiency and cancer exist, the results are conflicting, which might be partly due to limitations of the currently used genotyping procedures for GSTT1. Using biochemical analyses, three groups, high-, intermediate-, and non-conjugators, can be discriminated (Hallier et al., 1990). This may suggest a Mendelian intermediary inheritance (Wiebel et al., 1999), but so far the genetic background of intermediate and high conjugators and a gene-dose effect could not be unambiguously established. The currently used genetic assay for GSTT1 deficiency is a gene-specific PCR fragment that is present in conjugators, and absent in GSTT1*0/0. The fragment is therefore diagnostic for the presence of at least one functional allele (GSTT1*A) and a differentiation between homo- and heterozygous carriers of GSTT1*A is not possible, according to the state of the art.

This invention shows the characterization of the GSTT1 deletion, probably the result of a recombination event between two highly homologous regions that flank the GSTT1 gene. Utilizing the sequence of the GSTT1*0 recombination region, a PCR assay was devised that permits not only the unequivocal determination of homozygously deleted (*0/0) but also the discrimination of the heterozygously (*A/0) from the homozygously active (*A/A) individuals. The three GSTT1 genotypes detected by this procedure correlated highly significant with enzyme activity in erythrocytes. The trimodular distribution of phenotypes with high-, intermediate-, and null activity in homo- and heterozygotes for the *A allele and *0/0 homozygotes, respectively, indicates a gene-dose effect.

For initial determination and characterization of the GSTT1 deletion, samples of Caucasian volunteers from the Dr. Margarete Fischer-Bosch-Institute of Clinical Pharmacology in Stuttgart, and from the Institute of Clinical Pharmacology at the University Medical Center, Charité in Berlin have been used. Samples were obtained under consideration of all ethical and legal requirements. Genomic DNA was prepared from blood using the Qiagen (QiaAmp) kits on a Qiagen 9604 robot. For geno-phenotype correlations, phenotyped subjects have been used (n=130, male, mean age 30.7 years, ranging from 22 to 49 years) which were part of a previous study (Bruhn et al. 1998), DNA was obtained from these samples using phenol/chloroform extraction.

Determination of formaldehyde production rate (pmol HCHO/min/µl) from 31, 62, and 124 mM dichloromethane in hemolysate was used as a measure for GSTT1 activity (Bruhn et al., 1998).

NCBI database entries Z84718.1 and AP000351.2 (Genbank) contain GSTT1 sequences in annotated form (Z84718.1) or as raw data files, respectively. DNA sequence comparisons, alignments and the construction of composite files from raw data sequence files were performed using the programs FASTA and BLAST at the NCBI server.

Specific oligonucleotide primers for PCR of GSTT1 gene fragments from genomic DNA were derived (Table 1). Sequences of purified PCR fragments were obtained by automated DNA sequencing on ABI 377 (gel) or ABI 3700 (capillary) sequencers using BigDye Terminator cycle sequencing reactions (PE Biosystems). Amplification of fragments less than 2 kb was performed in 25 µl volume: 100 ng DNA template added to buffer containing 1.5 mM $MgCl_2$, 200 µM dNTPs, 0.2 mM each primer and 1 U HotStarTaq polymerase (all reagents Qiagen, Hilden, Germany). PCR was carried out in a Perkin Elmer GeneAmp System 9700 with an initial denaturation of 15 min at 95° C. followed by 30 cycles of 94° C. for 30 s, 30 s annealing and 60 s of extension at 72° C. Final extension was carried out for 7 min at 72° C. For longer amplicons 50 µl PCR reactions contain 200 ng of genomic DNA, reaction buffer 3, 500 µM dNTPs, 2.6 U Expand Taq-System (Roche, Basel, Switzerland) and 0.3 mM primers (Metabion, Munich, Germany). Samples were incubated at 92° C. for 2 min, followed by 35 cycles at 92° C. for 10 s, 45 s annealing at 68° C. for each kb per min extension time. The extension time of each cycle was increased by 20 s for the last cycles. 10 min final extension at 68° C. were applied.

The human GSTT1 gene is located on chromosome 22q11.2 which has recently been completely sequenced in the course of the human genome sequencing project (Dunham et al., 1999); prior to that, partial chromosome sequences were available in public databases from the Sanger Center. A 76799 bp DNA sequence of a BAC clone (gb: Z84718.1) contains the GSTT1 and the GSTT2 gene. Homology searches in unnotated raw sequences revealed one additional GSTT1-containing clone, AP000351.2 (118999 bp) consisting only of preliminary BAC sequences which are not assembled to a defined linear gene. A defined sequence file that contains GSTT1 and the flanking regions, which extends the annotated GSTT1 gene region of clone Z84718.1 was constructed by homology alignments using FASTA and BLAST at the NCBI server. Due to the high homology of parts of the sequences, the stringency of the alignments was set higher than default and the correctness of the assembled sequence was confirmed by visual inspection. The composition and prominent features of the GSTT1 gene region are shown in FIG. 1: GSTT1 and the homologous GSTT2 gene (55% protein homology, Tan et al., 1995) are separated by 49741 bp. In addition to many repetitive elements, GSTT1 is flanked by 18-kb regions which are more than 90% homologous (defined in the *A i.e. non-deleted allele, as homology region HA5 upstream and HA3 downstream of GSTT1).

Figure 2:
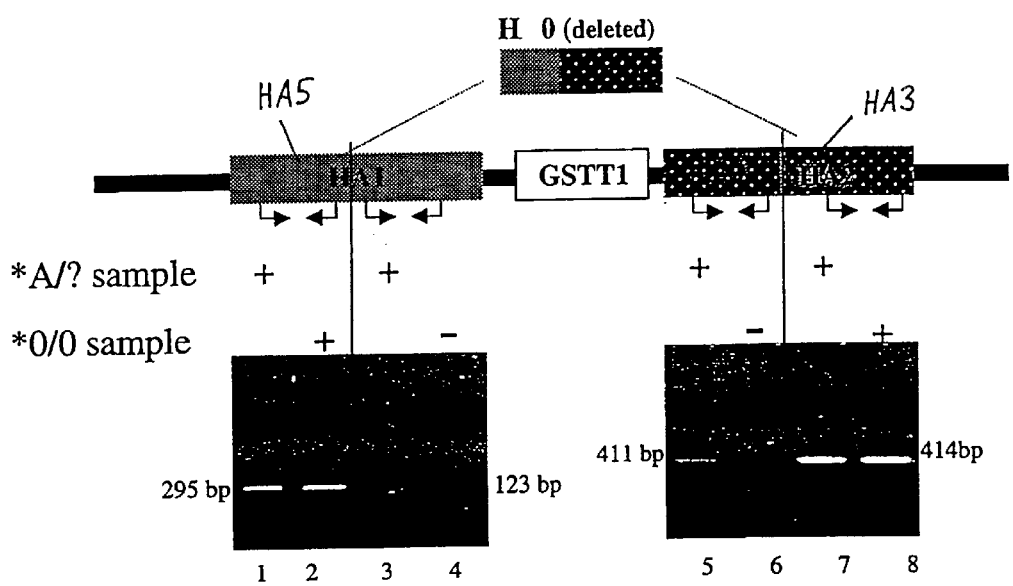

Although the detailed site of the GSTT1 deletion was unknown, the homozygous null allele could be diagnosed by the absence of a PCR fragment that is specifically amplified from the GSTT1 coding region (Pemble et al., 1994). The deletion removes GSTT1 but not GSTT2 (Tan et al., 1995). Therefore, one breakpoint of the deletion is positioned between GSTT1 and GSTT2 and the other must be downstream of GSTT1 (FIG. 1). To map the GSTT1 deletion we determined the presence or absence of specific sequences upstream and downstream of GSTT1 by PCR. Ten samples of the genotype GSTT1*0/0, and ten samples with at least one GSTT1*A allele were preselected (see FIG. 3a). Primer sets for specific amplification of fragments up- and downstream of GSTT1 were generated. This required extensive optimization considering the highly homologous flanking regions of GSTT1. Fragments that could be amplified from both, GSTT1*0/0 and samples containing at least one *A allele (*A) were regarded to be outside the deletion, whereas fragments that could exclusively be amplified from *A samples, but not from *0/0 contain the region which is deleted. FIG. 2 shows results of this mapping procedure. Primer combinations that bind upstream from position 50191, and downstream from position 110007 of the sequence file can be obtained from all samples. Fragments closer to GSTT1, downstream position 53494 and upstream position 105675 cannot be amplified from *0/0 samples. Therefore, the boundaries of the deletion must be localized within a region between position 50192 to 53493 upstream and 105676 to 110006 downstream of GSTT1.

Figure 3:
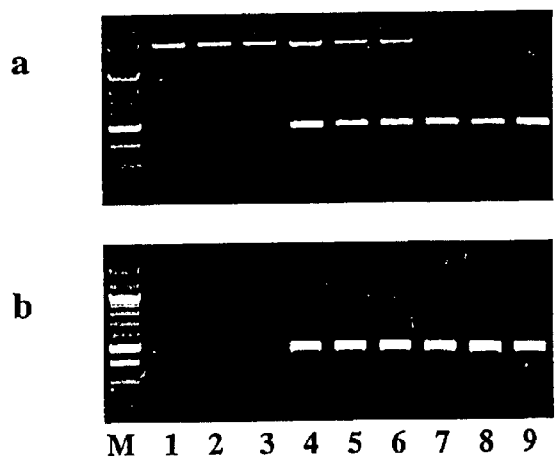
Figure 4:
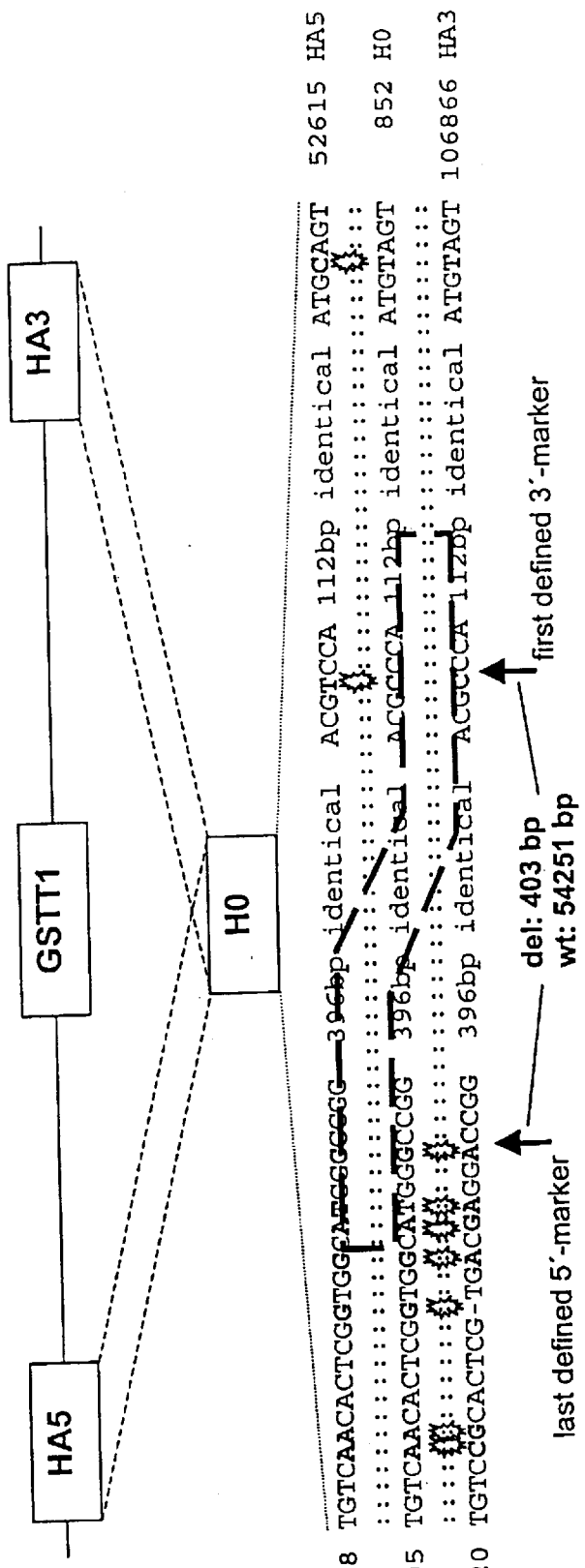

To home in on the exact positions of the deletion, we applied long range PCR has been applied to span the deletion in *0/0 samples. Various sets of PCR primers were selected close to the deletion boundaries as defined by PCR-mapping. In GSTT1*A samples, the 5' and 3' primers were separated by more than 60 kb, in *0/0 samples the distance between these primers was reduced by the size of the deletion. Utilizing different primer combinations, reproducibly deletion-spanning PCR fragments of 10065 bp, 3187 bp and of 1460 bp have been generated (FIG. 3, Table 3 for primer positions). The 10 kb fragment was sequenced to characterize the deletion region. The comparison of this null allele sequence with the GSTT1*A allele revealed the boundaries of the deletion (FIG. 4): it is flanked upstream and downstream by sequences that are part of the highly homologous HA5 and HA3 regions. In the *A allele, these regions flank GSTT1. In *0, the deletion generates a fusion sequence (H0) which differs from HA5 and HA3 by only a few nucleotide deviations as shown in FIG. 4. Using these deviations as "markers", for identification of the HA5 or HA3 portions of H0, the region where the deletion had happened could be narrowed down to a 403 bp sequence stretch. This sequence is identical in HA5 and HA3. These data support the assumption that the mechanism which generated the deletion is homologous recombination between the regions HA5 and HA3, which removes GSTT1 and generates H0.

The method according to the state of the art to analyze GSTT1 includes a critical negative test output: lack of a PCR signal defines *0/0 samples, whereas generation of the fragment detects the presence of at least one GSTT1*A allele (*A/A or *A/0). In addition to problems associated with negative test readouts (e.g. false results due to test failure may be misinterpreted as *0/0), another drawback of that method is that homozygous (*A/A) and heterozygous (*A/0) samples cannot be distinguished. Utilizing the molecular composition of the deletion, the invention devises a new genotyping protocol that allows not only a positive detection of the deletion allele, but also permits the unambiguous discrimination of all GSTT1 genotypes (*A/A, *A/0, and *0/0). The procedure generates deletion-spanning PCR fragments, which are combined with fragments that indicate the presence of GSTT1. Various PCR assays were evaluated using GSTT1 fragments in combination with deletion spanning fragments of sizes between 10065 and 1460 bp (table 3). Among these, one assay that had been established was found to be "robust" and allowed a reproducible simultaneous discrimination of all genotypes. The 1460 bp deletion-specific PCR fragment was combined with a 466 bp fragment that detected GSTT1*A. FIG. 3 shows the results of this assay applied to known *0/0 samples and *A/? samples: all samples that had previously been genotyped homozygous for the deletion by the standard method confirmed the *0/0 genotype with a positive readout of 1460 bp. The genotype GSTT1*A/A is diagnosed by the single 466 bp fragment and can be differentiated from heterozygous individuals who are characterized by the presence of both fragments. Testing more than 50 GSTT1*0/0 samples, no discrepancies were detected between the methods according to the state of the art and according to the invention.

Figure 5:
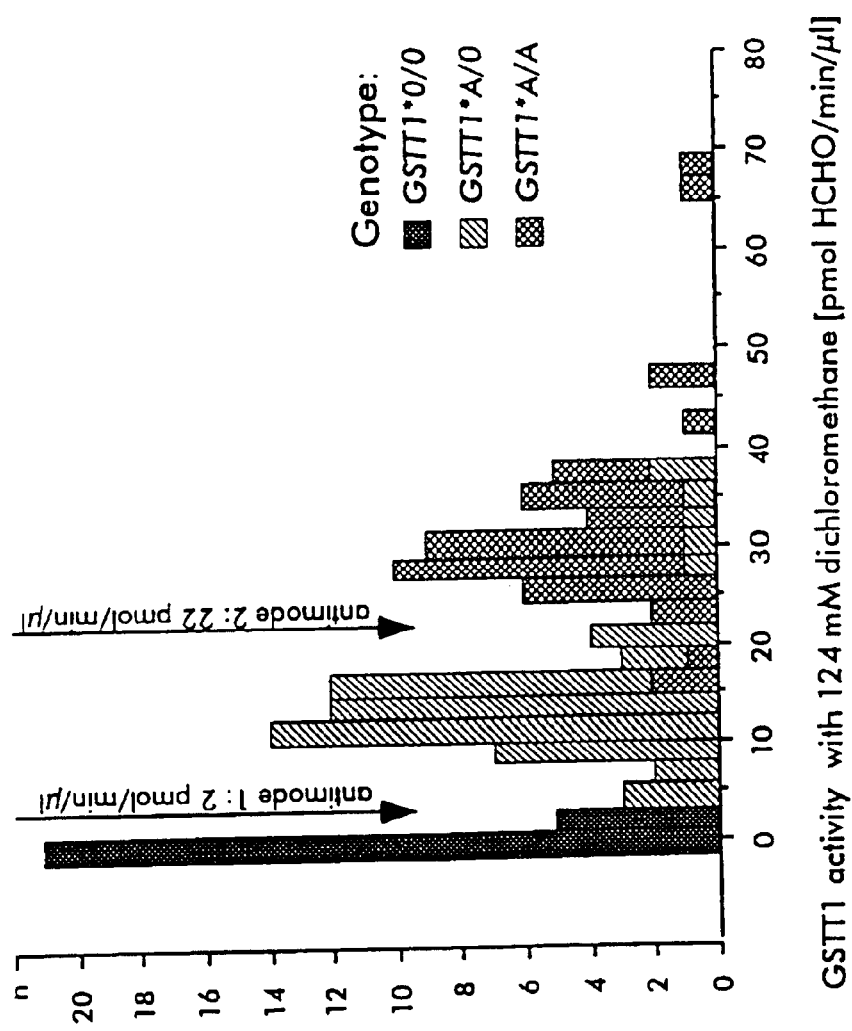
FIG. 5 shows the frequency distribution of GSTT1 conjugation activity in 130 samples.

The GSTT1*0/0 genotype correlates with the non conjugator phenotype. To evaluate whether intermediate and high conjugators are caused by *A/0 and *A/A genotypes, 130 samples whose GSTT1 activity in blood had been determined have been genotyped. FIG. 5 shows that the three GSTT1 genotypes could be assigned to distinct phenotypes: enzyme deficiency in GSTT1*0/0 samples, intermediate activity in *A/0 samples, and high activity in *A/A samples has been observed. The correlation of genotype and phenotype is statistically highly significant, $p<0.0001$ for all group comparisons (ANOVA with Bonferroni/Dunn correction for multiple testing). The allelic frequencies were in agreement with Hardy-Weinberg's law, the difference between observed and expected results (calculation based on the frequency of *0/0) was not significant (Table 2).

Characterization and Mechanism of the GSTT1 Deletion:

The invention allows to characterize the structure and mechanism of the GSTT1 deletion and identify two 18 kb homology regions flanking GSTT1 which are involved in the deletion (most likely crossing over) event that produced the *0 allele. Extensive sequence identity between both repeat regions in the *A allele, and between these repeats and the corresponding region in the deletion allele allowed to define the deletion boundaries within a 403 bp region. Gene deletion by homologous unequal crossing over has been described in other detoxification enzymes, in cytochrome P450 2D6 and glutathione S-transferase M1 (Steen et al., 1995; Xu et al., 1998; Kerb et al., 1999). Like in GSTM1, the GSTT1 deletion has a high frequency in the Caucasian population. Does this deletion consist of one defined null allele or are there various deletions with the loss of GSTT1 as the common denominator ? Since the assay showed the deletion allele as "measurable" PCR fragment, any variations in the size of the deletion indicative of multiple deletion alleles would have been detectable. In more than 150 *0 allele harboring samples that have been analyzed, the "deletion fragment" showed the same size of 1460 bp, suggesting that all GSTT1 deficiencies are caused by one allele.

Improved genotyping assay and allele distribution in Caucasians: So far, genotyping could detect the absence of GSTT1, but provided neither information about the boundaries of the deletion nor about the precise genotype. In spite of the extreme homology, a few single nucleotide variations specific for the recombinant region allow to create an assay for the detection of the inactive allele by presence of a PCR-fragment. A single PCR assay that detects this deletion-spanning PCR-fragment, combined with a fragment that indicates the presence of GSTT1, allows the unambiguous discrimination of all genotypes. Using the assay, the allele distribution was analyzed in Caucasian individuals and found to be 34% homozygous *A/A, 46% heterozygous, and 20% *0/0. This frequency fits to the distribution that would be expected on the basis of Hardy-Weinberg equilibrium (Table 2).

GSTT1 as risk factor in cancer: A number of epidemiological studies have been published on the medical importance of GSTT1 (Strange and Fryer, 1999). GSTT1*0/0 was found to be associated with brain cancer (Kelsey et al., 1997, Elexpuru Camiruaga et al., 1995), head- and neck cancer (Cheng et al., 1999), lung cancer in Hispanic- and African Americans (Kelsey et al., 1997). However, results were often ambiguous (Duncan et al., 1995, Heagerty et al., 1996) or gave conflicting results in bladder cancer (Kempkes et al., 1996, Brockmöller et al., 1996) and colorectal cancer (Clapper and Szarka, 1998; Zhang et al., 1999, Chenevix-Trench et al., 1995; Katoh et al., 1995; Gertig et al., 1998). In all these studies only a comparison of the null genotype with an active genotype was done. The difference between heterozygous and homozygous active individuals has not yet been elucidated, but determining both, could improve the statistical power in epidemiological studies.

Genotype-phenotype Correlation:

Phenotypic data have indicated the presence of intermediate conjugators displaying only half the activity of high conjugators (Warholm et al., 1995). These observations, and a family study that analyzed GSTT1 by semiquantitative PCR (Wiebel et al., 1999), suggest a gene-dosage effect on GSTT1 activity. In this, it has unambiguously been proven the intermediate Mendelian type of inheritance of GSTT1 for the first time. The enzyme activity of GSTT1 correlated highly significant with the number of functional alleles and phenotypically classified intermediate- and high conjugators were genotypically detected hetero (GSTT*A/0) and homozygous (*A/A), respectively. In only 9 among a total of 130 samples the genotype did not correlate well with the phenotype. Three intermediate conjugators had two active alleles and 6 samples with high enzyme activity displayed unexpectedly only one active allele. Since the enzymatic activity of all discrepant individuals was close to the antimode and the enzyme assay had a CV of 7%, differences are most likely the result of biological variability. With codominant inheritance, each allele confers a measurable, yet variable component to the phenotype resulting in a wide range of enzymatic activities from a distinct genotype and overlapping activities between homo- and heterozygotes. Furthermore, GSTT1 genotype-phenotype discrepancies can be modulated by exposure to inducers or inhibitors, whereas the genotype remains constant. Two other subjects attracted our attention because their extraordinary high conjugation activity was 2-fold higher than the mean of homozygous conjugators (68 pmol/min/$\mu$l versus 32 pmol/min/$\mu$l, FIG. 5). These subjects displayed the *A/A genotype in our assay. One possible explanation could be a gene duplication or amplification of GSTT1. Members of the GST multigene family have been evolutionary derived from a Theta-class gene duplication (Pemble and Taylor, 1992), and a duplicated class M1 gene that causes ultrarapid enzyme activity has already been described (McLellan et al., 1997). Thus, it is feasible that rare (2 of 130) ultrahigh GSTT1 activity may be caused by additionally amplified gene copies.

The identification of GSTT1 genotypes with a procedure that unambiguously discriminates *0/0, *A/0 and *A/A alleles predicts highly significant the phenotype and will allow an accurate assessment of health risk from halogenated alkanes or pesticides (Bruning et al., 1997; Au et al., 1999; El-Masri et al., 1999). It also provides a useful approach for the evaluation of the importance of GSTT1 as risk factor for various diseases.

This invention is especially suitable to check whether an individual has a genetic risk for UV mediated skin damage and/or skin cancer and/or cancers that are associated with oxidative stress and/or damage.

Figure 6:
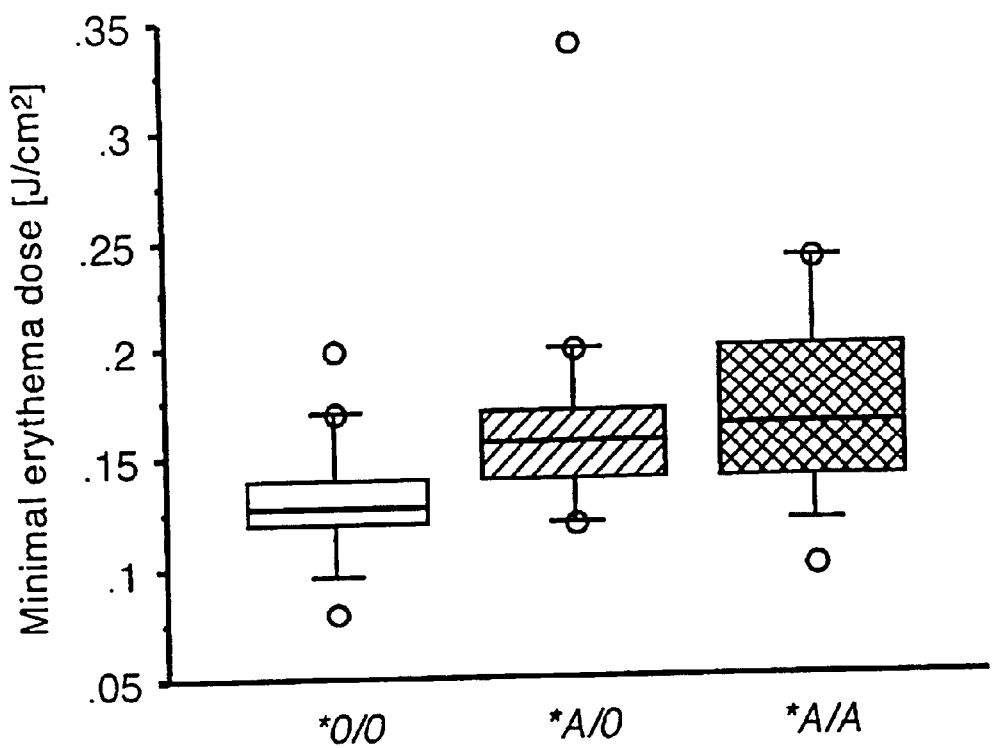
FIG. 6 shows the mean UV skin sensivity by minimal erythema dose according to GSTT1 genotype in 60 healthy volunteers.

Ultraviolet (UV) irradiation by sun exposure and family history are risk factors for the development of cutaneous melanoma. Inherited susceptibility to this type of skin cancer could therefore result from genetic factors that affect the capacity of cells to prevent UV-induced DNA lesions. UV light mediates the formation of radical oxygen species (ROS) such as hydroxyl and superoxide radicals, hydrogen peroxide, and single oxygens. These molecules comprise "oxidative stress" and damage cellular proteins, lipids, and DNA. Oxidative stress can cause inflammation, mutations, and genotoxicity. The skin is equipped with a defense system against oxidative stress (Vessey, 1993). Glutathione S-transferases (GSTs) contribute to this protection either by direct inactivation of peroxidized lipids and DNA (Berhane et al., 1994; Ketterer and Meyer, 1989; Tan et al., 1988), or by detoxification of xenobiotics, which can serve as cofactors of radical formation. Our improved assay system to detect GSTT1 deficiencies and heterozygotes shows that GST genotypes affect the susceptibility of individuals to oxidative or chemical stress. FIG. 6 shows the results of a panel comparison of two groups of genotypically characterized GSTT1 deficient, homozygous and heterozygous active subjects in respect to sunlight (UV) sensitivity. The GSTT1 genotyping was performed with the assay according to the invention that is described above. Healthy subjects (54 male, 6 female, 18 to 48 (mean 27.6) years old and of German Caucasian origin were selected for the panel comparison study. The constitutional skin types were assigned from tanning and burning histories using the Fitzpatrick's Classification (Fitzpatrick et al., 1987) and the study was performed during the winter months. Reactivity to UV light was determined in eight skin fields (1×0.6 cm) on non-UV exposed buttock skin by increasing doses of simulated sunlight with 20% dose increments (Wucherpfennig, 1931). Before each irradiation, UV intensity of the radiation source (dermalight 2001% equipped with an h2 filter, Dr. Höhnle, Munich, Germany) was calibrated to 1.33 mW/cm$^2$ at 280–315 nm, by use of a UVA/B Meter (Dr. Höhnle). UV dose [J/cm2] was calculated by intensity [mW/cm$^2$]×time [sec]/1000. Dose variations, from 0.07 J/cm$^2$ to 0.34 J/cm$^2$, were achieved by irradiation time. Erythema reactions were scored visually 20 hours post-exposure, independently by two examiners. All skin reactions were photographically documented. The irradiation dose of the first field with a barely perceptible erythema determined the minimal erythema dose (MED). The software package for statistical analyses SPSS 10.0 was applied to evaluate genotype-phenotype correlation and statistical significance (SPSS Inc., Chicago, USA). The dependency of UV sensitivity from genotype was tested with ANCOVA to control for constitutional skin type as confounding variable. Adjustment for multiple testing was done according to Bonferroni/Dunn.

The results of the panel comparison study showed a clear correlation of GSTT1-genotype and UV sensitivity of the skin: The GSTT1-deficient group has a higher inflammatory response after exposure to UV irradiation compared to the group with GSTT1 activity. Subjects homozygous for the GSTT1 deletion mutation required a statistically significant lower UV dose to barely perceptible erythema than those with one (GSTT1*A/0; p=0.067) or two (GSTT1*A/A; p=0.032) functionally active alleles. The erythema reaction did not decrease with the number of functional alleles and was equal in both GSTT1*A/0 and *A/A subjects. Among the 5 most UV-sensitive subjects (MED$\leq$0.10 J/cm$^2$) were 4 GSTT1 deficient and the two subjects with the lowest inflammatory response (MED$\geq$0.29) were both of enzyme-expressing genotype.

GSTT1 and GSTM1 are expressed in the skin and deficiencies in these enzymes by gene deletions impairs the capacity of cells to detoxify specific substrates, which include molecules that are generated by oxidative damage. The modification of molecules with reactive oxygens as substrate of GSTs provides one link between GSTs enzyme activity and protection against UV radiation-induced cutaneous damage. GST deficiencies result in increased susceptibility of cells to the consequences of ROS attack, such as inflammation or cancerogenesis (Fahey and Sundquist, 1991). UV irradiation by sun exposure and family history are risk factors for the development of skin cancer, particularly cutaneous melanoma. The fact that the GSTT1 and, to a lesser degree the GSTM1 genotype identifies individuals with increased UVsunlight-sensitivity, suggests GSTT1 and -M1 genotype variations to be among the genetic components that result in the inherited susceptibility or predisposition to skin cancer.

This invention further relates to a method for detecting the number of active alleles of the GSTT1 gene using the ABI TaqMan® technology and to a method for calibrating assays to detect the number of active GSTT1 alleles using quantitative techniques (e.g. TaqMan, Light Cyler, MALDI-TOF). Based on the molecular stucture of the GSTT1 gene a realtime quantitative TaqMan® PCR assay was developed, that amplifies a fragment within the coding sequence, and that coamplifies another fragment outside the GSTT1 gene as internal standard, so that the ratio between the yields of the both fragments (meassured by fluorescence signals) in a certain PCR cycle is independent from factors like template concentraion or DNA quality. Provided that the genomic seuquence of the internal standard is non-polymorphic, the number of active GSTT1 alleles is proportional to the described ratio. The internal standard to be used here is based on a fragment within the coding sequence of the CCR5 gene. Different polymorphic sites according to CCR5 are known (32 bp Del, NT794, 1 bp Del, Arg223Gln, Ala335Val, Cys303Ter), but none of them affect amplification of the internal standard fragment. The quantitative GSTT1 Taqman Method, described in this example, permits automized high throughput analyses of individual GSTT1 genotype. Furthermore, genomic DNA of lower quality than required for long range PCR (e.g. degraded DNA as yielded from paraffin-embedded or formalin-fixatated tissue samples) can be used as template. The prerequisite for developing the Taqman assay for GSTT1 genotyping is the knowledge of the exact numbers of individual GSTT1 alleles as described in the previous examples. Without knowing the exact number of the active GSTT1 alleles a calibration of the new assay is impossible. Therefore, this method can be considered as a variation, or a direct consequence, respectively, of the GSTT1 genotyping methods described above.

The ABI TaqMan® technology bases on molecular probes labelled by two fluorescence dyes: one is used as reporter and the other is used as quencher. The probe is placed within the fragment to be amplified. The 5'-3'-exonuclease activity of the Taq polymerase hydrolyses the probe, so that the reporter dye is no longer closed to the quencher dye and a fluorescence signal can be measured after excitation at $\lambda=488$ nm. The detected reporter signal ist directly proportional to the amplified PCR fragment. For coamplifying two fragments, two different reporter dyes must be used.

An example for the successful application of quantitative PCR (Taqman) to determine GSTT1 genotypes is shown below. The reaction conditions for the assay, in which the CCR5 gene was used as internal standard, were:

GSTT1

| | | |
|---|---|---|
| forward primer | GTG CCC TTC CCT TAC CCA TC<br>88589–88570 | (SEQ ID NO: 23) |
| reverse primer | GGG TAC CAG TAG TCA GGG ACC TTA<br>88494–88517 | (SEQ ID NO: 24) |
| probe | FAM-ACA GTG TGG CCA TCC TGC TCT ACC TGA-TAMRA<br>88554–88528<br>positions according to GI: 9937243 | (SEQ ID NO: 25) |

CCR5

| | | |
|---|---|---|
| forward primer | TGG CCT GAA TAA TTG CAG TAG CT<br>804–826 | (SEQ ID NO: 26) |
| reverse primer | GTG CGT CAT CCC AAG AGT CTC T<br>879–858 | (SEQ ID NO: 27) |
| probe | VIC-TAA GAG GTT GGA CCA AGC TAT GCA GGT GA-TAMRA<br>828–856<br>positions according to GI: 2347111 | (SEQ ID NO: 28) |

| component | | amount |
|---|---|---|
| template | | about 10 ng |
| GSTT1 | forward primer | 0.4 μM |
| | reverse primer | 0.4 μM |
| | probe | 0.2 μM |
| CCR5 | forward primer | 0.2 μM |
| | reverse primer | 0.2 μM |
| | probe | |
| TaqMan Universal PCR Master Mix (ABI) | | 1 × |
| water | | ad 25 μL |

| cycler | ABI Prism 7700 | |
|---|---|---|
| reaction's volume | 25 μL | |
| initial steps | 50° C. | 2 min |
| | 95° C. | 10 min |
| denaturation | 95° C. | 15 s |
| annealing and extension | 60° C. | 90 s |
| cycle number | 35 | |

PCR data were exported as "clipped data" to be analyzed, so that for each well and each cycle one fluorescence signal value was available. The ratios were built between the GSTT1 values and the CCR5 values for each sample and each cycle and then were diagrammed in dependance on the number of PCR cycles (FIG. 7).

Figure 7:
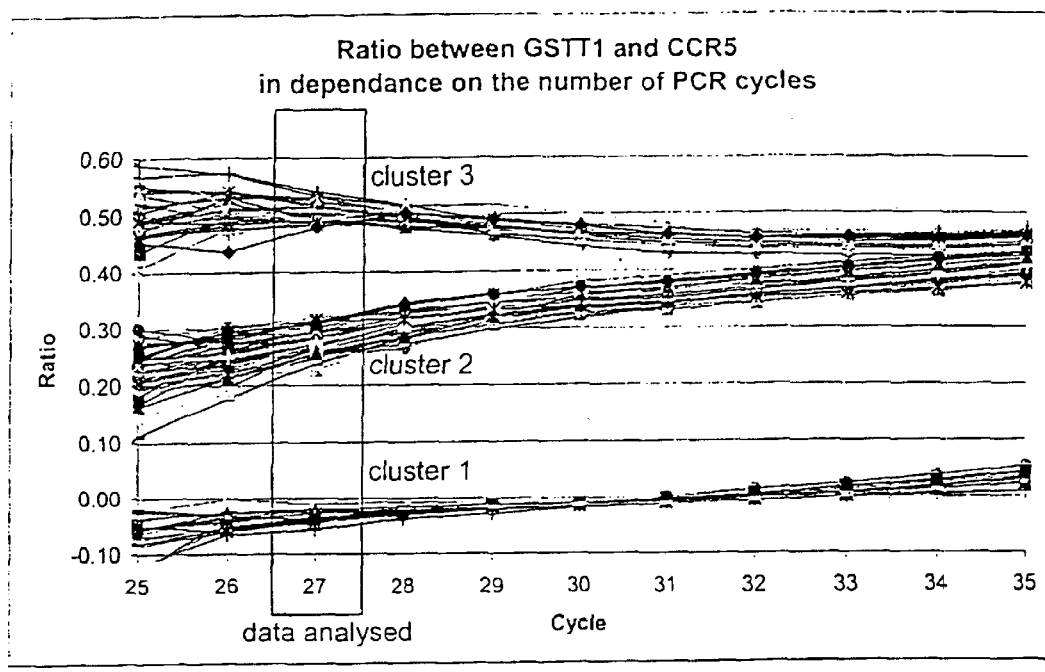
FIG. 7 shows the ratio between GSTT1 and CCR 5 in dependance on the number of PCR cycles.
Figure 8:
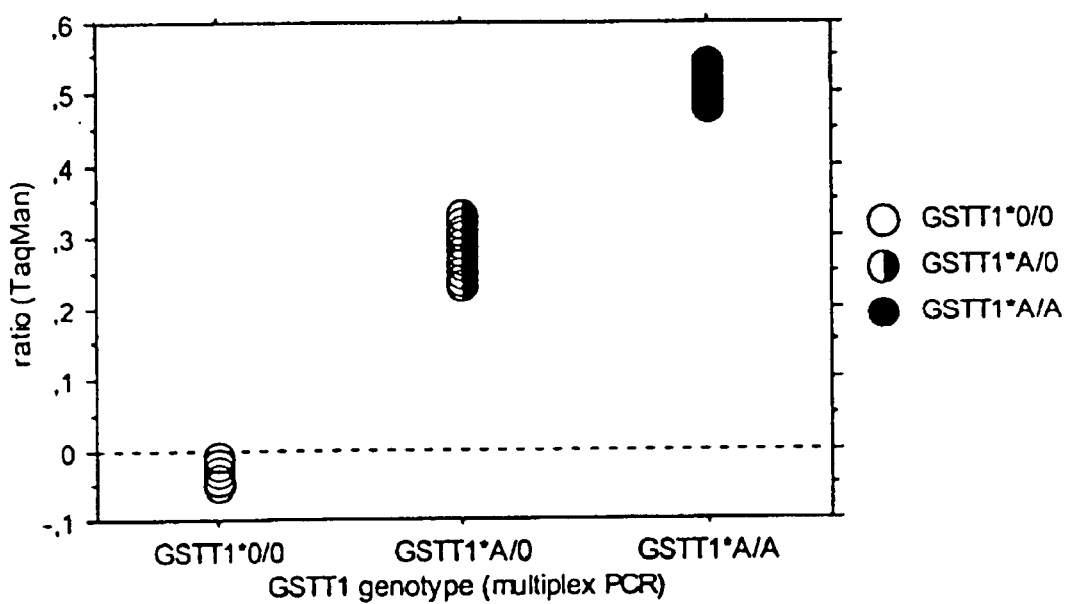
FIG. 8 shows the clusters with low, intermediate and high flurescense ratios corresponding to the genotypes GSTT1*0/0, GSTT1*A/0 and GSTT1*A/A respectively.

The computerized determination of the GSTT1 copy numbers from the output described in FIG. 7 was performed on data that were obtained at cycle counts>cycle 25. The calculation of fluorescence ratios from data obtained at cycles earlier than cycle 25 is not sensible, because the initial amplification's efficiency is not the same for both fragments. Between cycles 25 and 30, the amplicon yield is suifficiently high to calculate the ratio. In later cycles the reaction kinetics of the PCR leads to a plateau with no further increase of fluorescence signals, levelling differences between the clusters and therefore making the differentiation between homo- and heterozygous carriers of the null allele impossible. Assay evaluation was performed from data generated at 27 PCR cycles. Cluster analysis from the data output of the quantitative PCR resulted in three distinctive clusters of mean (min to max) signal ratios of −0.03 (−0.05−−0.01), 0.28 (0.23–0.33), and 0.58 (0.48–0.54) (table 5). The three clusters did not overlap and differed statistically highly significant from each other ($p<0.00001$, ANOVA with Bonferroni-Dunn adjustment for multiple testing) and the assignment to clusters was clear without ambiguity. Calibrating this new Taqman assay by comparing the results with those generated by the "method for detecting the presence of at least one single allele of a deletion mutant" revealed that the three clusters correlated completly with the number of active GSTT1 alleles as indicated by a Spearman-Rho of 1.0 ($p<0.001$). FIG. 8 illustrates the clusters with low, intermediate, and high fluorescence ratios corresponding to the genotypes GSTT1*0/0, GSTT1*A/O, and GSTT1*A/A, respectively.

The results of this analysis, performed on multiple samples of known GSTT1 genotype demonstrate the capability of the new method to unambiguously determine the copy number of the GSTT1 allele in individual samples.

TABLE 1

Primers for the characterization of the GSTT1 deletion locus and diagnostic PCR

| Name | Primer sequences [5'- . . . -3'] | SEQ ID Nos | Annealing [° C.] | Primer positions 5' | 3' |
|---|---|---|---|---|---|
| | Current Standard Method | | | | |
| GST-TF | TTC CTT ACT GGT CCT CAC ATC TC | 003 | 66 | 85920* | 85898* |
| GST-TR | TCA CCG GAT CAT GGC CAG CA | 004 | | 85462* | 85481* |
| | PCR mapping primers | | | | |
| GST-TF13 | CCC TCA CTC AGG GTT AGT GG | 005 | 63 | 110007* | 110026* |
| GST-TRF13 | GAT GCC ACG CGG CTT GTA GG | 006 | | 110301* | 110282* |
| GST-TF12 | GAT TGG TGG AAG GTG CCG GG | 007 | 63 | 105553* | 105576* |
| GST-TRF12 | CGT GTC TCT ACT TCA AAT TCC ATG | 008 | | 105675* | 105652* |
| GST-TFR11 | TAA GAT ACC TCA TAA AAT TAA CAG | 009 | 59 | 53904* | 53881* |
| GST-TR11 | GGG AGA ATG GAT AGT GGG GAG | 010 | | 53494* | 53514* |
| GST-TFR13 | GCA AGA AGA CCA GTG ACT GAG G | 011 | 63 | 50191* | 50170* |
| GST-TR13 | CTG CTC TTC TTC AGC AAC TCA G | 012 | | 49778* | 49800* |
| | 10065 bp *0 fragment primers | | | | |
| GST-TRF13 | GAT GCC ACG CGG CTT GTA GG | 013 | 65 | 110301* | 110282* |
| GST-TR12 | CTT TTT CTG CAG CAA ACG CAT TG | 014 | | 45986* | 46008* |
| | 3187 bp *0 fragment primers | | | | |
| GST-TRF13.2 | GAG CCA AGA AGT TCT GAG TCT TG | 015 | 65 | 108037* | 108015* |
| GST-TR9n | ATA TCA GCC AGA GAT CTC TGG G | 016 | | 50600* | 50621* |
| | Sequencing primers | | | | |
| GST-TRF13.3 | GCA TCC CAA TTC AAC ACG TGT TG | 017 | 62 | 107075* | 107053* |
| GSTT-F.1000 | CTT CTC AGC TGA AAC TTC CTC | 018 | | 51440* | 51460* |
| | GSTT1 deletion assay primers | | | | |
| GT*Af | CCA GCT CAC CGG ATC ATG GCC AG | 019 | 70 | 85457* | 85479* |
| GT*Ar | CCT TCC TTA CTG GTC CTC ACA TCT C | 020 | | 85922* | 85898* |
| GT*0f | GAG TTG TGA GCC ACG GTA CCC | 021 | | 52069*/6084** | 52089*/6114** |
| GT*0r | CGA TAG TTG CTG GCC CCC TC | 022 | | 107779*/7543** | 107760*/7524** |

*according to AP000351.2
**according to GSTT1*0

TABLE 2

GSTT1 allele distribution and phenotype correlation

| Genotype | *A/A | *A/0 | *0/0 |
|---|---|---|---|
| N | 44 | 60 | 26 |
| % observed | 33.8 | 46.2 | 20.0 |
| % expected[a] | 30.6[b] | 49.4[b] | 20.0[b] |
| Mean (SD) enzyme activity | 32.1(10.2)[c] | 15.0(7.4)[c] | 3.3(0.9)[c] |

[a]based on *0/0, according to Hardy-Weinberg
[b]$\chi^2 = 0.23$
[c]p < 0.0001, ANOVA with Bonferroni/Dunn correction for multiple testing

TABLE 3

PCR-fragments for GSTT1 genotyping.

| Sequence | SEQ ID Nos | Position | Size [bp] | Specificity | Comment |
|---|---|---|---|---|---|
| GATGCCACGCGGCTTGTAGG | 006 | 45986–46008 | 10065 | GSTT*0 | Long range PCR |
| CTTTTTCTGCACCAAACGCATTG | 014 | 110301–110282 | | | |
| ATATCAGCCAGAGATCTCTGGG | 016 | 50600–50621 | 3187 | GSTT1*0 | Long range PCR |
| CAGCCAAGAAGTTCTGAGTCTTG | 015 | 108015–108037 | | | |
| CAGTTGTGAGCCACCGTACCC | 021 | 52069–52089 | 1460 | GSTT1*0 | Standard PCR |
| CGATAGTTGCTGGCCCCCTC | 022 | 107779–107760 | | | |

TABLE 3-continued

PCR-fragments for GSTT1 genotyping.

| Sequence | SEQ ID Nos | Position | Size [bp] | Specificity | Comment |
|---|---|---|---|---|---|
| CCAGCTCACCGGATCATGGCCAG | 019 | 85457–85479 | 466 | GSTT1*A | Standard PCR |
| CCTTCCTTACTGGTCCTCACATCTC | 020 | 85922–85898 | | | |

TABLE 4

| | GST-Enzyme Activity | n | MED (J/cm$^2$)$^a$ Mean | Range | SD |
|---|---|---|---|---|---|
| GSTT1*A/A | High | 15 | 0.164 | 0.10–0.24 | 0.043 |
| GSTT1*A/0 | Intermediate | 22 | 0.157 | 0.12–0.29 | 0.048 |
| GSTT1*0/0 | Deficient | 23 | 0.129 | 0.08–0.20 | 0.027 |
| Total | | 60 | 0.145 | 0.08–0.29 | 0.037 |

$^a$Inflammatory reaction was detected as minimal erythema dose (MED) at 20 h after irradiation with UV

TABLE 5

Cluster analyses and statistical significance of the genotype correlation

| Number | Cluster | Distance from cluster center |
|---|---|---|
| 1 | 3 | 0.00 |
| 2 | 3 | 0.01 |
| 3 | 3 | 0.05 |
| 4 | 3 | 0.00 |
| 5 | 2 | 0.01 |
| 6 | 2 | 0.01 |
| 7 | 3 | 0.00 |
| 8 | 3 | 0.04 |
| 9 | 3 | 0.01 |
| 10 | 1 | 0.02 |
| 11 | 1 | 0.01 |
| 12 | 2 | 0.01 |
| 13 | 2 | 0.00 |
| 14 | 1 | 0.02 |
| 15 | 3 | 0.01 |
| 16 | 1 | 0.01 |
| 17 | 3 | 0.03 |
| 18 | 3 | 0.01 |
| 19 | 1 | 0.00 |
| 20 | 3 | 0.01 |
| 21 | 3 | 0.01 |
| 22 | 2 | 0.00 |
| 23 | 3 | 0.00 |
| 24 | 2 | 0.02 |
| 26 | 1 | 0.01 |
| 27 | 1 | 0.02 |
| 28 | 3 | 0.01 |
| 29 | 1 | 0.01 |
| 30 | 3 | 0.00 |
| 31 | 3 | 0.02 |
| 32 | 1 | 0.02 |
| 33 | 1 | 0.01 |
| 34 | 1 | 0.01 |
| 35 | 3 | 0.02 |
| 36 | 1 | 0.02 |
| 37 | 3 | 0.00 |
| 38 | 3 | 0.02 |
| 39 | 1 | 0.00 |
| 40 | 1 | 0.03 |
| 41 | 1 | 0.01 |
| 42 | 3 | 0.03 |
| 43 | 2 | 0.01 |
| 44 | 1 | 0.00 |
| 45 | 3 | 0.01 |
| 46 | 3 | 0.04 |
| 47 | 3 | 0.03 |
| 48 | 1 | 0.01 |
| 49 | 1 | 0.02 |
| 50 | 3 | 0.05 |
| 51 | 3 | 0.02 |
| 52 | 1 | 0.03 |
| 53 | 3 | 0.00 |
| 54 | 1 | 0.01 |
| 55 | 3 | 0.01 |
| 56 | 3 | 0.01 |
| 57 | 3 | 0.03 |
| 58 | 3 | 0.01 |
| 59 | 3 | 0.01 |
| 61 | 1 | 0.04 |
| 62 | 3 | 0.02 |
| 63 | 2 | 0.00 |
| 64 | 1 | 0.02 |
| 65 | 2 | 0.00 |
| 66 | 1 | 0.01 |
| 67 | 3 | 0.01 |
| 68 | 3 | 0.02 |
| 69 | 3 | 0.03 |
| 70 | 1 | 0.01 |
| 71 | 2 | 0.02 |
| 72 | 3 | 0.00 |
| 73 | 1 | 0.02 |
| 74 | 3 | 0.01 |
| 75 | 1 | 0.01 |
| 76 | 3 | 0.00 |
| 77 | 3 | 0.01 |
| 78 | 3 | 0.01 |
| 79 | 3 | 0.00 |
| 80 | 1 | 0.01 |
| 81 | 2 | 0.01 |
| 82 | 1 | 0.03 |
| 83 | 2 | 0.01 |
| 84 | 2 | 0.01 |
| 85 | 2 | 0.00 |
| 86 | 2 | 0.01 |
| 87 | 3 | 0.01 |
| 88 | 3 | 0.01 |
| 89 | 2 | 0.01 |
| 90 | 2 | 0.01 |
| 91 | 3 | 0.03 |
| 92 | 3 | 0.02 |
| 93 | 3 | 0.02 |
| 94 | 3 | 0.01 |
| 95 | 3 | 0.03 |
| 96 | 3 | 0.03 |

What is claimed is:

1. A method for determining whether a subject exhibits a GSTT1*0/0 genotype, a GSTT1*A/A genotype, or a GSTT1*A/0 genotype, comprising the steps of:

isolating genomic DNA from a subject;

performing a PCR on the isolated genomic DNA using a primer pair selected from the group of primer pairs consisting of CAG CCA AGA AGT TCT GAG TCT TG (SEQ ID NO: 15) and ATA TCA GCC AGA GAT CTC TGG G (SEQ ID NO: 16), CCA GCT CAC CCG ATC ATG GCC AG (SEQ ID NO: 19) and CCT TCC TTA CTG GTC CTC ACA TCT C (SEQ ID NO: 20), CAG TTG TGA GCC ACC GTA CCC (SEQ ID NO: 21) and CGA TAG TTG CTG GCC CCC TC (SEQ ID NO: 22), and GTG CCC TTC CCT TAC CCA TC (SEQ ID NO: 23) and GGG TAC CAG TAG TCA GGG ACC TTA (SEQ ID NO: 24); and analyzing results of the PCR for the absence or presence of specific DNA fragments, the absence of specific DNA fragments indicating the subject exhibits the GSTT1*0/0 genotype and the presence of specific DNA fragments indicating the subject exhibits the GSTT1*A/A genotype or the GSTT1*A/0 genotype.

* * * * *